United States Patent
Sharifi et al.

(10) Patent No.: US 12,121,630 B2
(45) Date of Patent: Oct. 22, 2024

(54) LIGHT ACTIVATED ADHESIVE SCAFFOLD

(71) Applicant: Massachusetts Eye and Ear Infirmary, Boston, MA (US)

(72) Inventors: Roholah Sharifi, Boston, MA (US); Miguel Gonzalez Andrades, Boston, MA (US); James Chodosh, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 654 days.

(21) Appl. No.: 17/271,817

(22) PCT Filed: Sep. 3, 2019

(86) PCT No.: PCT/US2019/049330
§ 371 (c)(1),
(2) Date: Feb. 26, 2021

(87) PCT Pub. No.: WO2020/051133
PCT Pub. Date: Mar. 12, 2020

(65) Prior Publication Data
US 2021/0322645 A1   Oct. 21, 2021

Related U.S. Application Data

(60) Provisional application No. 62/726,548, filed on Sep. 4, 2018.

(51) Int. Cl.
| | |
|---|---|
| *A61L 27/50* | (2006.01) |
| *A61L 24/00* | (2006.01) |
| *A61L 24/10* | (2006.01) |
| *A61L 27/22* | (2006.01) |
| *B29C 35/08* | (2006.01) |
| *B29L 31/00* | (2006.01) |

(52) U.S. Cl.
CPC .............. *A61L 27/50* (2013.01); *A61L 24/001* (2013.01); *A61L 24/104* (2013.01); *A61L 27/222* (2013.01); *A61L 2400/06* (2013.01); *A61L 2430/16* (2013.01); *B29C 35/0805* (2013.01); *B29K 2089/00* (2013.01); *B29K 2907/00* (2013.01); *B29L 2031/753* (2013.01)

(58) Field of Classification Search
None
See application file for complete search history.

(56) References Cited

U.S. PATENT DOCUMENTS

| | | |
|---|---|---|
| 5,064,430 A | 11/1991 | Urry |
| 5,674,623 A | 10/1997 | Haddon et al. |
| 6,458,386 B1 | 10/2002 | Schacht et al. |
| 6,585,873 B1 | 7/2003 | Solomon et al. |
| 6,608,040 B1 | 8/2003 | Lin et al. |
| 7,435,425 B2 | 10/2008 | Qian et al. |
| 7,547,446 B2 | 6/2009 | Qian et al. |
| 7,854,923 B2 | 12/2010 | Chen et al. |
| 7,871,637 B2 | 1/2011 | Qian et al. |
| 7,871,639 B2 | 1/2011 | Schankereli et al. |
| 8,092,820 B2 | 1/2012 | Qian et al. |
| 8,314,211 B2 | 11/2012 | Fallus et al. |
| 8,383,141 B2 | 2/2013 | Qian et al. |
| 8,513,217 B2 | 8/2013 | Chen et al. |
| 9,066,991 B2 | 6/2015 | Preiss-Bloom et al. |
| 9,084,728 B2 | 7/2015 | Goessl et al. |
| 11,058,800 B2 | 7/2021 | Khademhosseini et al. |
| 2004/0110439 A1 | 6/2004 | Chaikof et al. |
| 2005/0112182 A1 | 5/2005 | Minami et al. |
| 2008/0070029 A1 | 3/2008 | Hessing et al. |
| 2008/0287565 A1 | 11/2008 | Liska et al. |
| 2008/0312156 A1 | 12/2008 | Setton et al. |
| 2009/0175946 A1 | 7/2009 | Gaissmaier et al. |
| 2011/0008442 A1 | 1/2011 | Zawko et al. |
| 2012/0128653 A1 | 5/2012 | Goessl et al. |
| 2013/0172985 A1 | 7/2013 | Prestwich et al. |
| 2014/0107065 A1 | 4/2014 | Chen et al. |
| 2014/0154212 A1 | 6/2014 | Tanzi et al. |
| 2014/0377326 A1 | 12/2014 | Niu et al. |
| 2015/0037314 A1 | 2/2015 | Larsen |
| 2015/0209109 A1 | 7/2015 | Rege et al. |
| 2015/0291939 A1 | 10/2015 | Tomer et al. |
| 2017/0232138 A1 | 8/2017 | Khademhosseini et al. |
| 2017/0281828 A1 | 10/2017 | Zhang et al. |
| 2019/0022280 A1 | 1/2019 | Khademhosseini et al. |

(Continued)

FOREIGN PATENT DOCUMENTS

| | | |
|---|---|---|
| CN | 107551326 | 1/2018 |
| JP | 2002-506431 A | 2/2002 |
| JP | 2009-522001 A | 6/2009 |

(Continued)

OTHER PUBLICATIONS

Yang et al. (CN103739862B Machine Translation) (Year: 2015).*
Alaminos et al., "Construction of a complete rabbit cornea substitute using a fibrin-agarose scaffold," Invest Ophthalmol Vis Sci., 2006, 47(8):3311-3317.
Alaminos et al., "Volumetric and ionic regulation during the in vitro development of a corneal endothelial barrier," Exp Eye Res, 2008, 86(5):758-769.
Allen et al., "Prospective Randomized Study Evaluating a Biodegradable Polymeric Sealant for Sealing Intraoperative Air Leaks That Occur During Pulmonary Resection," The Annals of Thoracic Surgery, 2004, 77:1792-1801.

(Continued)

*Primary Examiner* — Robert A Wax
*Assistant Examiner* — Quanglong N Truong
(74) *Attorney, Agent, or Firm* — Fish & Richardson P.C.

(57) ABSTRACT

The present invention discloses compositions and methods for repair and reconstruction of defects and injuries to soft tissues. Some aspects of the disclosure provide methods for corneal reconstruction by applying an engineered bioadhesive, glycidyl methacrylate-substituted gelatin and a visible light activated photoinitiator in presence of visible light to the corneal defect.

18 Claims, 53 Drawing Sheets

(56) References Cited

U.S. PATENT DOCUMENTS

2022/0001074 A1    1/2022    Dana et al.

FOREIGN PATENT DOCUMENTS

| KR | 10-1562366 | 10/2015 |
|---|---|---|
| WO | WO 1998/055161 | 12/1998 |
| WO | WO 2007/079053 | 7/2007 |
| WO | WO 2016/022807 | 2/2016 |
| WO | WO 2016/049345 | 3/2016 |
| WO | WO 2016/178586 | 11/2016 |
| WO | WO 2017/062429 | 4/2017 |
| WO | WO 2017/117467 | 7/2017 |
| WO | WO 2017/139318 | 8/2017 |
| WO | WO 2021/133457 | 7/2021 |

OTHER PUBLICATIONS

Alleyne et al., "Efficacy and biocompatibility of a photopolymerized, synthetic, absorbable hydrogel as a dural sealant in a canine craniotomy model," J Neurosurg., 1998, 88:308-313.

Andermann et al., "Application of iron(III)-hydroxamic acid complexes in the spectrophotometric determination of poly(vinyl alcohol) in pharmaceutical preparations," Analyst, 1980, 105:575-80.

Anegg et al., "Efficiency of fleece-bound sealing (TachoSil®) of air leaks in lung surgery: a prospective randomised trial," European Journal of Cardio-thoracic Surgery, 2007, 31:198-202.

Annabi et al., "25th Anniversary Article: Rational Design and Applications of Hydrogels in Regenerative Medicine," Advanced Materials, 2014, 26(1):85-124.

Annabi et al., "Cross-linked open-pore elastic hydrogels based on tropoelastin, elastin and high pressure CO2," Biomaterials, 2010, 31:1655-1665.

Annabi et al., "Engineered cell-laden human protein-based elastomer," Biomaterials, 2013, 34(22):5496-5505.

Annabi et al., "Engineering a highly elastic human protein-based sealant for surgical applications," Science Translational Medicine, 2017, 9(410):eaai7466, 16 pages.

Annabi et al., "Engineering a sprayable and elastic hydrogel adhesive with antimicrobial properties for wound healing," Biomaterials, 2017, 139:229-243.

Annabi et al., "Highly Elastic Micropatterned Hydrogel for Engineering Functional Cardiac Tissue," Advanced Functional Materials, 2013, 23:4950-4959.

Annabi et al., "Surgical Materials: Current Challenges and Nano-enabled Solutions," Nano Today, 2014, 9(5):574-589.

Annabi et al., "Synthesis of highly porous crosslinked elastin hydrogels and their interaction with fibroblasts in vitro," Biomaterials, 2009, 30:4550-4557.

Annabi et al., "The fabrication of elastin-based hydrogels using high pressure CO2," Biomaterials, 2009, 30:1-7.

Anselmo et al., "Platelet-like Nanoparticles: Mimicking Shape, Flexibility, and Surface Biology of Platelets to Target Vascular Injuries," ACS Nano, 2014, 8(11):11243-11253.

Appel et al., "Self-assembled hydrogels utilizing polymer-nanoparticle interactions," Nat Commun., 2015, 6:6295, 9 pages.

Assmann et al., "The degeneration of biological cardiovascular prostheses under pro-calcific metabolic conditions in a small animal model," Biomaterials, 2014, 35(26):7416-7428.

ASTM D638-14, Standard Test Method for Tensile Properties of Plastics, ASTM International, West Conshohocken, PA, 2014, 17 pages.

ASTM D695-15, Standard Test Method for Compressive Properties of Rigid Plastics, ASTM International, West Conshohocken, PA, 2015, 9 pages.

AU Office Action in Australian Application No. 2017217454, dated May 15, 2020, 5 pages.

Baldock et al., "Shape of tropoelastin, the highly extensible protein that controls human tissue elasticity," PNAS, 2011, 108(11):4322-4327.

Baranoski, "Choosing a wound dressing, part 1," Nursing, 2008, 38:60-61.

Benton et al., "Photocrosslinking of Gelatin Macromers to Synthesize Porous Hydrogels That Promote Valvular Interstitial Cell Function," Tissue Eng Pt A, 2009, 15(11):3221-3230.

Bernad et al., "Modification of the amino and hydroxyl groups of lysozyme with carboxylic acid anhydrides: a comparative study," Biochimica et Biophysica Acta (BBA)—Protein Structure and Molecular Enzymology, 1986, 873:350-5.

Bertassoni et al., "Hydrogel Bioprinted Microchannel Networks for Vascularization of Tissue Engineering Constructs," Lab Chip, 2014, 14(13):2202-2211.

Betre et al., "Chondrocytic differentiation of human adipose-derived adult stem cells in elastin-like polypeptide," Biomaterials, 2006, 27:91-99.

Bhatia, "Ocular surface sealants and adhesives," Ocul Surf., 2006, 4(3):146-154.

Bitton et al., "Phloroglucinol-based biomimetic adhesives for medical applications," Acta Biomaterialia, 2009, 5:1582-1587.

Bottcher-Haberzeth et al., "Tissue engineering of skin," Burns, 2010, 36:450-460.

Buckley et al., "Silver carbonate nanoparticles stabilised over alumina nanoneedles exhibiting potent antibacterial properties, " Chem. Commun., 2008, 4013-4015.

Buskens et al., "The use of a surgical sealant (CoSeal®) in cardiac and vascular reconstructive surgery: an economic analysis," The Journal of Cardiovascular Surgery, 2006, 47(2):161-170.

Camci-Unal et al., "Synthesis and Characterization of Hybrid Hyaluronic Acid-Gelatin Hydrogels," Biomacromolecules, 2013, 14(4):1085-1092.

Carlson et al., "Giant Papillary Conjunctivitis Associated With Cyanoacrylate Glue," Am J Ophthalmol., 1987, 104(4):437-438.

Carnahan et al., "Hybrid dendritic-linear polyester-ethers for in situ photopolymerization," J. Am. Chem. Soc., 2002, 124(19):5291-5293.

Carrico et al., "Lithographic Patterning of Photoreactive Cell-Adhesive Proteins," J. Am. Chem. Soc., 2007, 129(16):4874-4875.

Cavanaugh et al., "Infectious Keratitis and Cyanoacrylate Adhesive," Am. J. Ophthalmol., 1991, 111(4):466-472.

Cha et al., "Controlling Mechanical Properties of Cell-Laden Hydrogels by Covalent Incorporation of Graphene Oxide," Small, 2014, 10(3):514-523.

Cha et al., "Microfluidics-assisted fabrication of gelatin-silica core-shell microgels for injectable tissue constructs," Biomacromolecules, Jan. 2014, 15(1):283-90, 13 pages.

Charati et al., "Hydrophilic elastomeric biomaterials based on resilin-like polypeptides," Soft Matter, 2009, 5(18):3412-3416.

Chen et al., "Functional Human Vascular Network Generated in Photocrosslinkable Gelatin Methacrylate Hydrogels," Advanced Functional Materials, 2012, 22(10):2027-2039.

Chen et al., "Layer-by-Layer Bioprinting of Stem Cells for Retinal Tissue Regeneration," University of California, San Diego, 2016, 14 pages.

Chou et al., "Genetically encoding an aliphatic diazirine for protein photocrosslinking," Chemical Science, 2011, 2:480-483.

Colyer et al., "Perforating globe injuries during operation Iraqi Freedom," Ophthalmology, Nov. 2008, 115(11):2087-2093.e2.

Costa et al., "Stimuli-Responsive Thin Coatings Using Elastin-Like Polymers for Biomedical Applications," Advanced Functional Materials, 2009, 19:3210-3218.

Cushing et al., "Hydrogel Cell Cultures," Science, 2007, 316(5828):1133-1134.

Deacon et al., "Antimicrobial efficacy of tobramycin polymeric nanoparticles for Pseudomonas aeruginosa infections in cystic fibrosis: formulation, characterisation and functionalisation with dornase alfa (DNase)," Journal of Controlled Release, Jan. 2015, 198:55-61, 16 pages.

Debelle et al., "Elastin: molecular description and function," The International Journal of Biochemistry & Cell Biology, Feb. 1999, 31(2):261-272.

Di Zio et al., "Mechanical Properties of Artificial Protein Matrices Engineered for Control of Cell and Tissue Behavior," Macromolecules, 2003, 36(5):1553-1558.

(56) References Cited

OTHER PUBLICATIONS

Elisseeff et al., "Transdermal photopolymerization for minimally invasive implantation," Proc Natl Acad Sci U S A, Mar. 1999, 96(6):3104-3107.
Elvin et al., "A highly elastic tissue sealant based on photopolymerised gelatin," Biomaterials, Nov. 2010, 31(32):8323-8331.
Elzoghby, "Gelatin-based nanoparticles as drug and gene delivery systems: Reviewing three decades of research," Journal of Controlled Release, Dec. 2013, 172(3):1075-1091.
EP Extended European Search Report in European U.S. Appl. No. 17/750,660, dated Jun. 15, 2020, 10 pages.
Extended European Search Report in European Appln. No. 19858168.8, dated Apr. 25, 2022, 11 pages.
Extended European Search Report in European Appln. No. 19873530.0, dated Jun. 6, 2022, 8 pages.
Fantes et al., "Wound healing after excimer laser keratomileusis (photorefractive keratectomy) in monkeys," Archives of Ophthalmology, 1990, 108(5):665-675.
FDA.gov [online], "Device Approvals, Denials and Clearances," Mar. 26, 2018, retrieved on Jul. 7, 2022, retrieved from URL<www.fda.gov/MedicalDevices/ProductsandMedicalProcedures/DeviceApprovalsandClearances>, 1 page.
Feiner et al., "Engineered hybrid cardiac patches with multifunctional electronics for online monitoring and regulation of tissue function," Nat Mater., 2016, 15(6):679-685, 8 pages.
Fogle et al., "Tissue Adhesive Arrests Stromal Melting in the Human Cornea," American Journal of Ophthalmology, Jun. 1980, 89(6):795-802.
Foo et al., "Two-component protein-engineered physical hydrogels for cell encapsulation," Proceedings of the National Academy of Sciences, Dec. 2009, 106(52):22067-22072.
Gaharwar et al., "Shear-Thinning Nanocomposite Hydrogels for the Treatment of Hemorrhage," ACS Nano, 2014, 8(10):9833-9842.
Galler et al., "Self-assembling Multidomain Peptide Hydrogels: Designed Susceptibility to Enzymatic Cleavage Allows Enhanced Cell Migration and Spreading," J Am Chem Soc., Mar. 2010, 132(9):3217-3223.
Garoff et al., "Improvements of DNA sequencing gels," Anal Biochem., Aug. 1981, 115(2):450-457.
Garzon et al., "Generation of a biomimetic human artificial cornea model using Wharton's jelly mesenchymal stem cells," Invest Ophthalmol Vis Sci., 2014, 55(7):4073-4083.
Ghobril et al., "A Dendritic Thioester Hydrogel Based on Thiol-Thioester Exchange as a Dissolvable Sealant System for Wound Closure," Angewandte Chemie International Edition, 2013, 125(52):14320-14324.
Giannandrea et al., "Diverse functions of matrix metalloproteinases during fibrosis," Disease Models & Mechanisms, Feb. 2014, 7(2):193-203.
Glassman et al., "End block design modulates the Assembly and Mechanics of Thermoresponsive, Dual-Associative Protein Hydrogels," Macromolecules, Mar. 2015, 48(6):1832-1842.
Glickman et al., "A Polymeric Sealant Inhibits Anastomotic Suture Hole Bleeding More Rapidly Than Gelfoam/ Thrombin: Results of a Randomized Controlled Trial," Archives of Surgery, Mar. 2002, 137(3):326-331.
Gonzalez-Andrades et al., "Generation of bioengineered corneas with decellularized xenografts and human keratocytes," Invest Ophthalmol Vis Sci., 2011, 52(1):215-222.
Gorgieva et al., "Collagen-vs. Gelatine-Based Biomaterials and Their Biocompatibility: Review and Perspectives," Biomaterials Applications for Nanomedicine, In Tech, 2011, 38 pages.
Grinstaff, "Biodendrimers: New polymeric biomaterials for tissue engineering," Chemistry—A European Journal, Jul. 2002, 8(13):2838-2846.
Grinstaff, "Designing hydrogel adhesives for corneal wound repair," Biomaterials, Dec. 2007, 28(35):5205-5214.

Hariprasad et al., "Polyethylene glycol hydrogel polymer sealant for vitrectomy surgery: an in vitro study of sutureless vitrectomy incision closure," Archives of Ophthalmology, 2011, 129(3):322-325.
Hassan et al., "Smart copper oxide nanocrystals: Synthesis, characterization, electrochemical and potent antibacterial activity," Colloids Surfaces B: Biointerfaces, Apr. 2012, 97:201-206.
Haugh et al., "The effect of dehydrothermal treatment on the mechanical and structural properties of collagen-GAG scaffolds," J Biomed Mater Res A, 2009, 89(2):363-369.
He et al., "Polymorphisms in the Human Tropoelastin Gene Modify In Vitro Self-Assembly and Mechanical Properties of Elastin-Like Polypeptides," PLOS ONE, Sep. 2012, 7(9):e46130, 12 pages.
Hida et al., "Retinal Toxicity of Cyanoacrylate Tissue Adhesive in the Rabbit," Retina, 1988, 8(2):148-153, 10 pages.
Hjortnaes et al., "Directing Valvular Interstitial Cell Myofibroblast-Like Differentiation in a Hybrid Hydrogel Platform," Advanced Healthcare Materials, 2015, 4:121-130.
Hrabchak et al., "Assessment of biocompatibility and initial evaluation of genipin cross-linked elastin-like polypeptides in the treatment of an osteochondral knee defect in rabbits," Acta Biomaterialia, Jun. 2010, 6:2108-2115.
Huang et al., "A novel hydrogel with high mechanical strength: Amacromolecularmicrosphere composite hydrogel," Adv Mater., 2007, 19(12):1622-1626.
Huang et al., "Generation of Synthetic Elastin-Mimetic Small Diameter Fibers and Fiber Networks," Macromolecules, 2000, 33(8):2989-2997.
Hutson et al., "Synthesis and Characterization of Tunable Poly(Ethylene Glycol): Gelatin Methacrylate Composite Hydrogels," Tissue Engineering: Part A, 2011, 17(13 &14):1713-1723.
Ifkovits et al., "Review: Photopolymerizable and Degradable Biomaterials for Tissue Engineering Applications," Tissue Engineering, Oct. 2007, 13(10):2369-2385.
ImageScience.org [online], NeuronJ: An ImageJ Plugin for Neurite Tracing and Analysis, May 2022, retrieved on Jul. 7, 2022, retrieved from URL<www.imagescience.org/meijering/software/neuronj/>, 2 pages.
International Preliminary Report on Patentability in International Appln. No. PCT/US/2020/054838, dated Apr. 21, 2022, 6 pages.
International Search Report and Written Opinion in International Appln. No. PCT/US/2020/054838, dated Jul. 1, 2021, 8 pages.
Islam et al., "Self-assembled collagen-like-peptide implants as alternatives to human donor corneal transplantation," RSC Advances, 2016, 6(61):55745-55749.
Itano, "The optimal technique for combined application of fibrin sealant and bioabsorbable felt against alveolar air leakage," European Journal of Cardio-thoracic Surgery, Mar. 2008, 33:457-460.
Jeon et al., "Shape-Morphing Materials from Stimuli-Responsive Hydrogel Hybrids," Ace Chem Res., 2017, 50(2):161-169, 9 pages.
Jhanji et al., "Management of Corneal Perforation," Surv Ophthalmol, 2011, 56(6):522-538.
Jun et al., "Comparison of Bursting Pressure after Scleral Tunnel Incision Sealed with Sutures or an Adherent Ocular Bandage in Human Globes," The Journal of International Medical Research, Apr. 2012, 40:756-760.
Katagiri et al., "All Six Modules of the Gelatin-binding Domain of Fibronectin Are Required for Full Affinity," The Journal of Biological Chemistry, Apr. 2003, 278(14):11897-11902.
Kessler et al., "Methacrylated gelatin/hyaluronan-based hydrogels for soft tissue," Journal of Tissue Engineering, Dec. 2017, 8: 14 pages.
Kharaziha et al., "Tough and Flexible CNT-Polymeric Hybrid Scaffolds for Engineering Cardiac Constructs," Biomaterials, Aug. 2014, 35(26):7346-7354.
Kheirkhah et al., "Comparison of Standard Versus Wide-Field Composite Images of the Corneal Subbasal Layer by In Vivo Confocal Microscopy," Investigative Ophthalmology & Visual Science, Sep. 2015, 56(10):5801-5807.
Kheirkhah et al., "Corneal Epithelial Immune Dendritic Cell Alterations in Subtypes of Dry Eye Disease: a Pilot In Vivo Confocal Microscopic Study," Investigative Ophthalmology & Visual Science, Nov. 2015, 56(12):7179-7185.

(56) References Cited

OTHER PUBLICATIONS

Kheirkhah et al., "Effects of corneal nerve density on the response to treatment in dry eye disease," Ophthalmology, Apr. 2015, 122(4):662-668, 7 pages.

Kheirkhah et al., "Overestimation of Corneal Endothelial Cell Density in Smaller Frame Sizes in In Vivo Confocal Microscopy," Cornea, Dec. 2015, 35(3):363-369.

Kheirkhah et al., "Reduced Corneal Endothelial Cell Density in Patients With Dry Eye Disease," American Journal of Ophthalmology, Jun. 2015, 159(6):1022-1026e.2, 7 pages.

Kim et al., "Biomimetic Scaffolds for Tissue Engineering," Advanced Functional Materials, Mar. 2012, 22(12):2446-2468.

Kim et al., "Self-Assembly of Thermally Responsive Amphiphilic Diblock Copolypeptides into Spherical Micellar Nanoparticles," Angewandte Chemie International Edition, Jun. 2010, 49(25):4257-4260.

Kobayashi et al., "In Vivo Evaluation of a New Sealant Material on a Rat Lung Air Leak Model," Journal of Biomedical Materials Research (Applied Biomaterials), 2001, 58(6):658-665.

Kretlow et al., "Injectable matrices and scaffolds for drug delivery in tissue engineering," Adv Drug Deliv Rev., 2007, 59(4-5):263-273.

Lai and Li, "Functional Assessment of Cross-Linked Porous Gelatin Hydrogels for Bioengineered Cell Sheet Carriers," Biomacromolecules, Mar. 2010, 11(5):1387-1397.

Lai et al., "Gelatin methacrylate/carboxybetaine methacrylate hydrogels with tunable crosslinking for controlled drug release," Journal of Materials Chemistry B, 2016, 4(13):2304-2313.

Lai et al., "Nanoscale modification of porous gelatin scaffolds with chondroitin sulfate for corneal stromal tissue engineering," Int J Nanomed, 2012, 2012(7):1101-1114.

Lang et al., "A blood-resistant surgical glue for minimally invasive repair of vessels and heart defects," Sci Transl Med, Jan. 2014, 6(218):218ra216, 11 pages.

Leahey et al., "Clinical Experience with N-butyl Cyanoacryiate (Nexacryl) Tissue Adhesive," Ophthalmology, Feb. 1993, 100(2):173-180.

Lee et al., "Hydrogels for Tissue Engineering," Chemical Reviews, Jul. 2001, 101(7):1869-1879.

Lee et al., "Synthesis and characteristics of interpenetrating polymer network hydrogel composed of chitosan and poly(acrylic acid)," Journal of Applied Polymer Science, Jul. 1999, 73(1):113-120.

Leggat et al., "Surgical applications of cyanoacrylate adhesives: a review of toxicity," ANZ Journal of Surgery, Apr. 2007, 77(4):209-213.

Leijten et al., "Spatially and temporally controlled hydrogels for tissue engineering," Mat Sci Eng R, Sep. 2017, 119:1-35.

Li et al., "Novel visible-light-induced photocurable tissue adhesive composed of multiply styrene-derivatized gelatin and poly(ethylene glycol) diacrylate," Journal of Biomedical Materials Research, 2003, 66B(1):439-446.

Li et al., "Tough adhesives for diverse wet surfaces," Science, Jul. 2017, 357(6349):378-381, 4 pages.

Li et al., "Toward a Stretchable, Elastic, and Electrically Conductive Nanocomposite: Morphology and Properties of Poly[styrene-b-(ethylene-co-butylene)-b-styrene]/Multiwalled Carbon Nanotube Composites Fabricated by High-Shear Processing," Macromolecules, Apr. 2009, 42(7):2587-2593.

Lim et al., "Rapid Crosslinking of Elastin-like Polypeptides with Hydroxymethylphosphines in Aqueous Solution," Biomacromolecules, 2007, 8(5):1463-1470.

Lynn et al., "Antigenicity and Immunogenicity of Collagen," Journal of Biomedical Materials Research Part B: Applied Biomaterials, Nov. 2004, 71(2):343-354.

MacEwan et al., "Applications of elastin-like polypeptides in drug delivery," Journal of Controlled Release, Sep. 2014, 190:314-330.

MacEwan et al., "Elastin-Like Polypeptides: Biomedical Applications of Tunable Biopolymers," Peptide Science, 2010, 94(1):60-77.

Mandal et al., "Silk fibroin/polyacrylamide Semi-interpenetrating network hydrogels for controlled drug release," Biomaterials, May 2009, 30(14):2826-2836.

Mayumi and Ito, "Structure and dynamics of polyrotaxane and slide-ring materials," Polymer, Feb. 2010, 51(20):4461-4461.

McHale et al., "Synthesis and in Vitro Evaluation of Enzymatically Cross-Linked Elastin-Like Polypeptide Gels for Cartilaginous Tissue Repair", Tissue Engineering, 2005, 11(11/12):1768-1779.

Mehdizadeh et al., "Injectable citrate-based mussel-inspired tissue bioadhesives with high wet strength for sutureless wound closure," Biomaterials, Nov. 2012, 33(32):7972-7983.

Meyer et al., "Purification of recombinant proteins by fusion with thermally-responsive polypeptides," Nature Biotechnology, 1999, 17:1112-1115.

Mimura et al., "Tissue engineering of corneal stroma with rabbit fibroblast precursors and gelatin hydrogels," Mol Vis, 2008, 14:1819-1828.

Montanaro et al., "Cytotoxicity, blood compatibility and antimicrobial activity of two cyanoacrylate glues for surgical use," Biomaterials, Jan. 2001, 22(1):59-66.

Monzyk and Crumbliss, "Mechanism of ligand substitution on high-spin iron(III) by hydroxamic acid chelators. Thermodynamic and kinetic studies on the formation and dissociation of a series of monohydroxamatoiron(III) complexes," Journal of the American Chemical Society, 1979, 101(21):6203-13.

Mũnoz et al., "Gelatin hydrogels formed by orthogonal thiol-norbornene photochemistry for cell encapsulation," Biomaterials Science, 2014, 2:1063-1072, 10 pages.

Myung et al., "Glucose permeability of human, bovine, and porcine corneas in vitro," Ophthalmic Res, 2006, 38(3):158-163.

Myung et al., "Progress in the development of interpenetrating polymer network hydrogels," Polym Adv Technol, Apr. 2008, 19(6):647-657.

Nagapudi et al., "Photomediated Solid-State Cross-Linking of an Elastin-Mimetic Recombinant Protein Polymer," Macromolecules, 2002, 35(5):1730-1737.

Nakayama et al., "Enhancement of visible light-induced gelation of photocurable gelatin by addition of polymeric amine," Journal of Photochemistry and Photobiology A: Chemistry, 2006, 177:205-211.

Nan et al., "Nosocomial Infection After Lung Surgery: Incidence and Risk Factors," Chest, Oct. 2005, 128(4):2647-2652.

Nettles et al., "Applications of Elastin-like Polypeptides in Tissue Engineering," Advanced Drug Delivery Reviews, Dec. 2010, 62(15):1479-1485.

Nettles et al., "*In Situ* Crosslinking Elastin-Like Polypeptide Gels for Application to Articular Cartilage Repair in a Goat Osteochondral Defect Model," Tissue Engineering Part A, May 2008, 14(7):1133-1140.

Ní Annaidh et al., "Characterization of the anisotropic mechanical properties of excised human skin," J Mech Behav Biomed Mater, Jan. 2012, 5(1):139-148.

Nichol et al., "Cell-laden microengineered gelatin methacrylate hydrogels," Biomaterials, Jul. 2010, 31(21):5536-5544.

Nikkhah et al., "Directed endothelial cell morphogenesis in micropatterned gelatin methacrylate hydrogels," Biomaterials, Dec. 2012, 33(35):9009-9018.

Office Action in European Appln. No. EP17750660.7, dated Jun. 20, 2022, 9 pages.

Office Action in Japanese Application No. 2018-541314, dated Oct. 21, 2020, 31 pages (with English translation).

Office Action in Japanese Appln. No. 2021-083614, dated Jun. 8, 2022, 12 pages (with English translation).

Okajima et al., "Kinetics of vol. phase transition in poly(N-isopropylacrylamide) gels," Journal of Chemical Physics, May 2002, 116(20):9068-9077.

Omidian et al., "Elastic, Superporous Hydrogel Hybrids of Polyacrylamide and Sodium Alginate," Macromolecular Bioscience, Sep. 2006, 6(9):703-710.

Orban et al., "Cytomimetic Biomaterials. 4. In-Situ Photopolymerization of Phospholipids on an Alkylated Surface," Macromolecules, 2000, 33(11):4205-4212.

(56) References Cited

OTHER PUBLICATIONS

Papatheofanis, "Prothrombotic Cytotoxicity of Cyanoacrylate Tissue Adhesive," Journal of Surgical Research, Oct. 1989, 47(4):309-312.
Pardo et al., "Mechanisms of nucleophilic addition to activated double bonds: 1,2- and 1,4-Michael addition of ammonia," J Am Chem Soc, 1993, 115(18):8263-8269.
Park et al., "Delivery of TGF-β1 and chondrocytes via injectable, biodegradable hydrogels for cartilage tissue engineering applications," Biomaterials, Dec. 2005, 26(34):7095-7103.
Park et al., "Evaluation of polyethylene glycol based hydrogel for tissue sealing after laparoscopic partial nephrectomy in a porcine model," The Journal of Urology, Dec. 2004, 172:2446-2450.
Pascolini and Mariotti, "Global estimates of visual impairment: 2010," Br J Ophthalmol, May 2012, 96(5):614-618.
Patel and McGhee, "Quantitative analysis of in vivo confocal microscopy images: a review," Survey of Ophthalmology, Sep. 2013, 58:466-475, 10 pages.
Paul et al., "Injectable Graphene Oxide/Hydrogel-Based Angiogenic Gene Delivery System for Vasculogenesis and Cardiac Repair," ACS Nano, 2014, 8(8):8050-8062.
PCT International Search Report mailed Apr. 21, 2017, in correspondence to International Application No. PCT/US17/16917, 14 pages.
PCT International Preliminary Report on Patentability in International Application No. PCT/US2017/016917, dated Aug. 14, 2018, 10 pages.
PCT International Preliminary Report on Patentability in International Appln. No. PCT/US2019/056521, dated Apr. 29, 2021, 8 pages.
PCT International Search Report and Written Opinion in International Appln. No. PCT/US2019/056521, dated Jan. 10, 2020, 9 pages.
Petroll and Robertson, "In Vivo Confocal Microscopy of the Cornea: New Developments in Image Acquisition, Reconstruction, and Analysis Using the HRT-Rostock Corneal Module," The Ocular Surface, Jul. 2015, 13:187-203.
Prausnitz and Langer, "Transdermal drug delivery," Nat Biotechnol, Nov. 2008, 26(11):1261-1268.
Qerimi et al., "Collagen hemostat significantly reduces time to hemostasis compared with cellulose: COBBANA, a single-center, randomized trial," The American Journal of Surgery, Jun. 2013, 205(6):636-641, 6 pages.
Rana and Savant, "A brief review of techniques used to seal corneal perforation using cyanoacrylate tissue adhesive," Cont Lens Anterior Eye, Aug. 2013, 36(4):156-158.
Raphel et al., "Photoreactive elastin-like proteins for use as versatile bioactive materials and surface coatings," Journal of Materials Chemistry, 2012, 22(37):19429-19437.
Ravi et al., "Accepted Manuscript: 3D cell culture systems: advantages and applications," J Cell Physiol, Jan. 2015, 230(1):16-26, 32 pages.
Resnikoff et al., "Global data on visual impairment in the year," Bull. W.H.O., Nov. 2004, 82(11):844-851, 9 pages.
ReSure® Sealant, "Summary of Safety and Effectiveness Data," FDA label, Jan. 2014, 37 pages.
Rogers et al., "Materials and Mechanics for Stretchable Electronics," Science, Mar. 2010, 327(5973):1603-1607.
Sakai et al., "Design and fabrication of a high-strength hydrogel with ideally homogeneous network structure from tetrahedron-like macromonomers," Macromolecules, Jun. 2008, 41(14):5379-5384.
Sani et al., "An Antimicrobial Dental Light Curable Bioadhesive Hydrogel for Treatment of Peri-Implant Diseases," Matter, 2019, 1(4):926-944, 20 pages.
Sani et al., "Sutureless repair of corneal injuries using naturally derived bioadhesive hydrogels," Science Advances, 2019, 5(3):eaav1281, 14 pages.
Sharma et al., "Human cartilage repair with a photoreactive adhesive-hydrogel composite," Sci Transl Med, Jan. 2013, 5(167):167ra6, 10 pages.
Shazly et al., "Viscoelastic adhesive mechanics of aldehyde-mediated soft tissue sealants," Biomaterials, Dec. 2008, 29(35):4584-4591.
Shi et al., "Accepted Manuscript: Highly stretchable and super tough nanocomposite physical hydrogels facilitated by the coupling of intermolecular hydrogen bonds and analogous chemical crosslinking of nanoparticles," J Mater Chem B, 2015, 3(7):1187-1192, 7 pages.
Shin et al., "Carbon Nanotube Reinforced Hybrid Microgels as Scaffold Materials for Cell Encapsulation," ACS Nano, Jan. 2012, 6(1):362-372.
Shin et al., "Carbon-Nanotube-Embedded Hydrogel Sheets for Engineering Cardiac Constructs and Bioactuators," ACS Nano, Mar. 2013, 7(3):2369-2380.
Siegal et al., "Surgical Removal of Cyanoacrylate Adhesive After Accidental Instillation in the Anterior Chamber," Ophthalmic Surgery, Mar. 1989, 20(3):179-181.
Sivakumar et al., "Grafting of glycidyl methacrylate onto gelatin," Journal of Applied Polymer Science, 1991, 43(10):1789-1794.
Sk et al., "Synthesis and characterization of site selective photo-crosslinkable glycidyl methacrylate functionalized gelatin-based 3D hydrogel scaffold for liver tissue engineering," Mater Sci Eng C Mater Biol Appl., Apr. 2021, 123:111694.
Spotnitz et al., "Hemostats, sealants, and adhesives III: a new update as well as cost and regulatory considerations for components of the surgical toolbox," Transfusion, Oct. 2012, 52(10):2243-2255, 13 pages.
Sun et al., "Highly stretchable and tough hydrogels," Nature, Sep. 2012, 489(7414):133-136.
Tang et al., "Oxidatively Responsive Chain Extension to Entangle Engineered Protein Hydrogels," Macromolecules, Jan. 2014, 47(2):791-799.
Teng et al., "Morphological analysis of leucocyte transmigration in the pleural cavity," Journal of Anatomy, Oct. 2003, 203(4):391-404.
Tessmar et al., "Customized PEG-Derived Copolymers for Tissue-Engineering Applications," Macromolecular Bioscience, Jan. 2007, 7(1):23-39.
Thach et al., "Intraocular foreign body injuries during operation Iraqi freedom," Ophthalmology, Oct. 2005, 112(10):1829-1833.
Than et al., "Polyethylene glycol hydrogel dural sealant may reduce incisional cerebrospinal fluid leak after posterior fossa surgery," Operative Neurosurgery, Jul. 2008, 63(ONS Suppl 1):ONS182-ONS187.
Trabbic-Carlson et al., "Swelling and Mechanical Behaviors of Chemically Cross-Linked Hydrogels of Elastin-like Polypeptides," Biomacromolecules, 2003, 4(3):572-580.
Tuncaboylu et al., "Tough and Self-Healing Hydrogels Formed via Hydrophobic Interactions," Macromolecules, 2011, 44(12):4997-5005.
Urry et al., "Biocompatibility of the Bioelastic Materials, Poly(GVGVP) and Its y-Irradiation Cross-Linked Matrix: Summary of Generic Biological Test Results," Journal of Bioactive and Compatible Polymers, 1991, 6:263-282.
Vakalopoulos et al., "Mechanical Strength and Rheological Properties of Tissue Adhesives With Regard to Colorectal Anastomosis an Ex Vivo Study," Ann Surg, 2015, 261(2):323-331.
Visser et al., "Endochondral bone formation in gelatin methacrylamide hydrogel with embedded cartilage-derived matrix particles," Biomaterials, Jan. 2015, 37:174-182, 9 pages.
Wang et al., "A simple and high-resolution stereolithography-based 3D bioprinting system using visible light crosslinkable biolinks," Biofabrication, Dec. 2015, 7(4):045009, 11 pages.
Wang et al., "A tough biodegradable elastomer," Nature Biotechnology, Jun. 2002, 20:602-606.
Wang et al., "Development of a photo-crosslinking, biodegradable GelMA-PEGDA hydrogel for guided bone regeneration materials," Materials, Jan. 2018, 11(1345):12 pages.
Wang et al., "Paper: Visible light-based stereolithography bioprinting of cell-adhesive gelatin hydrogels," Paper, Presented at Proceedings of the IEEE Annual International Conference of the IEEE Engineering in Medicine and Biology Society (EMBC), Jeju, South Korea, Jul. 11-15, 2017, 1599-1602.

(56) References Cited

OTHER PUBLICATIONS

Weiss et al., "The Use of Tissue Adhesive in Corneal Perforations," Ophthalmology, 1983, 90(6):610-615.
Welsh et al., "Engineering the Extracellular Matrix: a Novel Approach to Polymeric Biomaterials. I. Control of the Physical Properties of Artificial Protein Matrices Designed to Support Adhesion of Vascular Endothelial Cells," Biomacromolecules, Feb. 2000, 1(1):23-30.
Whitcher et al., "Corneal blindness: a global perspective," Bull. W.H.O., 2001, 79(3):214-221.
Wissink et al., "Immobilization of heparin to EDC/NHS-crosslinked collagen. Characterization and in vitro evaluation," Biomaterials, 2001, 22(2):151-163.
Wolbank et al., "Non-invasive in vivo tracking of fibrin degradation by fluorescence imaging," Journal of Tissue Engineering and Regenerative Medicine, Aug. 2015, 9(8):973-976, 4 pages.
Xia et al., "Author Manuscript: Tunable Self-Assembly of Genetically Engineered Silk-Elastin-Like Protein Polymers," Biomacromolecules, Nov. 2011, 12(11):3844-3850, 16 pages.
Xia et al., "Nano-structured smart hydrogels with rapid response and high elasticity," Nature Communications, Jul. 2013, 4:2226, 11 pages.
Xu et al., "Rheological Properties of Cysteine-Containing Elastin-Like Polypeptide Solutions and Hydrogels," Biomacromolecules, 2012, 13(8):2315-2321.
Yue et al. "Synthesis, properties, and biomedical applications of gelatin methacryloyl (GelMA) hydrogels," Biomaterials, Dec. 2015, 73:254-71.
Zhang et al., "A Highly Elastic and Rapidly Crosslinkable Elastin-Like Polypeptide-Based Hydrogel for Biomedical Applications," Advanced Functional Material, Aug. 2015, 25(30):4814-4826.
Zhang et al., "Artificial Polypeptide Scaffold for Protein Immobilization," Journal of the American Chemical Society, Jul. 2005, 127(29):10136-10137.
Zhao et al. "Photocrosslinkable Gelatin Hydrogel for Epidermal Tissue Engineering," Advanced Healthcare Materials, Jan. 2016, 6(1):108-118, 11 pages.
Zhou et al., "Biomimetic mineralization of anionic gelatin hydrogels: effect of degree of methacrylation," RSC Advances, 2014, 4:21997-22008.
Zhu and Marchant, "Design properties of hydrogel tissue-engineering scaffolds," Expert Review of Medical Devices, Sep. 2011, 8(5):607-626.
Camci-Unal et al., "Surface-modified hyaluronic acid hydrogels to capture endothelial progenitor cells," Soft Matter, Aug. 2010, 6(20):5120-6.
EP Office Action in European Appln. No. 20906625.7, mailed on Oct. 20, 2023, 11 pages.
Trujillo-de Santiago et al., "Ocular adhesives: Design, chemistry, crosslinking mechanisms, and applications," Biomaterials, Mar. 2019, 197:345, 76 pages.
Löwenberg et al., "Influence of glycidylmethacrylate functional groups attached to gelatin on the formation and properties of hydrogels," Mater. Res. Soc. Symp. Proc., 2015, 1718:103-108.
Office Action in European Appln. No. 19858168.8, dated Oct. 5, 2023, 8 pages.
Office Action in Australian Appln. No. 2019336666, dated Apr. 10, 2024, 6 pages.
International Preliminary Report on Patentability in International Appln. No. PCT/US2019/049330, mailed Mar. 18, 2021, 9 pages.
International Search Report and Written Opinion in International Appln. No. PCT/US2019/049330, mailed Nov. 18, 2019, 10 pages.
Li et al., "Fabrication of Highly Crosslinked Gelatin Hydrogel and Its Influence on Chondrocyte Proliferation and Phenotype," Polymers, Jul. 2017, 9(8):309, 14 pages.
Teramoto et al., "Preparation and Mechanical Properties of Photo-Crosslinked Fish Gelatin/Imogolite Nanofiber Composite Hydrogel," Materials, Dec. 2012, 5(12):2573-2585.

\* cited by examiner

M0397_SINA-6m-A_040
M0397_SINA-6m-A
SS, grid 10A, 2.5%GTH + Pb stain
Print Mag: 4630x @ 7.0 in
6:00:31 PM 12/11/2017

10 µm
MV=80.0kV
Direct Mag: 2900x
X: -347.51496  Y: -122.571984

M0397_SINA-6m-A_042
M0397_SINA-6m-A
SS, grid 10A, 2.5%GTH + Pb stain
Print Mag: 7660x @ 7.0 in
6:02:19 PM 12/11/2017

2 µm
MV=80.0kV
Direct Mag: 4800x
X: -343.24368 Y: -113.237448

M0397_SINA-6m-A_043
M0397_SINA-6m-A
SS, grid 10A, 2.5%GTH + Pb stain
Print Mag: 10800x @ 7.0 in
6:03:18 PM 12/11/2017

2 µm
MV=80.0kV
Direct Mag: 6800x
X: -342.05496  Y: -133.396744

M0397_SINA-6m-A_045
M0397_SINA-6m-A
SS, grid 10A, 2.5%GTH + Pb stain
Print Mag:20700x @ 7.0 in
5:05:38 PM 12/11/2017

500 nm
MV=80.0kV
Direct Mag: 13000x
X: -343.00968 Y: -114.11148

M0397_SINA-6m-B_043
M0397_SINA-6m-B LM
SS, grid 9A, 2.5%GTH + POb stain
Print Mag: 14800x @ 7.0 in
6:01:25 PM 12/11/2017

2 μm
MV=80.0kV
Direct Mag: 9300x
X: -58.62324  Y: 591.303608

M0397_SINA-6m-B_041
M0397_SINA-6m-B LM
SS, grid 9A, 2.5%GTH + POb stain
Print Mag: 20700x @ 7.0 in
4:02:25 PM 12/11/2017

500 nm
M=80.0kV
Direct Mag: 13000x
X: -56.52036 Y: 592.579024

M0397_SINA-6m-B_070
M0397_SINA-6m-B LM
SS, grid 9A, 2.5%GTH + POb stain
Print Mag: 14800x @ 7.0 in
4:27:58 PM 12/11/2017

2 μm
MV=80.0kV
Direct Mag: 9300x
X: 83.67684  Y: 566.217616

M0397_SINA-6m-B_060
M0397_SINA-6m-B LM
SS, grid 9A, 2.5%GTH + POb stain
Print Mag: 14800x @ 7.0 in
4:19:00 PM 12/11/2017

2 μm
M=80.0kV
Direct Mag: 9300x
X: -6.11832  Y: 566.341296

M0397_SINA-6m-A_113
M0397_SINA-6m-A
SS, grid 10 A, 2.5%GTH + Pb stain
Print Mag: 29500x @ 7.0 in
10:27:35 PM 12/12/2017

500 µm
MV=80.0kV
Direct Mag: 18500x
X: -285.57204 Y: 729.745456

M0397_SINA-6m-A_085
M0397_SINA-6m-A
SS, grid 10A, 2.5%GTH + Pb stain
Print Mag: 17500x @ 7.0 in
10:02:32 PM 12/12/2017

2 µm
M=80.0kV
Direct Mag: 11000x
X: -267.2982 Y: 596.10764

LIGHT ACTIVATED ADHESIVE SCAFFOLD

CROSS-REFERENCE TO RELATED APPLICATIONS

This application is the U.S. national stage entry of PCT Application No. PCT/US2019/049330, filed on Sep. 3, 2019, which claims benefit under 35 U.S.C. § 119(e) of U.S. Provisional Application No. 62/726,548, filed Sep. 4, 2018 The entire contents of the foregoing are hereby incorporated by reference.

FIELD OF THE DISCLOSURE

The invention relates to biocompatible, light-crosslinkable bioadhesives for use in repairing soft tissue injuries and defects.

BACKGROUND

Corneal diseases are emerging as one of the main causes of blindness (Whitcher, J. P.; Srinivasan, M.; Upadhyay, M. P., Corneal blindness: a global perspective. Bull. W.H.O. 2001, 79, 214-221) including various infectious and noninfectious diseases such as progressive corneal thinning, microbial keratitis, trauma, and immune disorders. Unilateral corneal blindness is estimated to occur in 23 million people worldwide, with 4.9 million people suffering from bilateral corneal blindness (Resnikoff, S.; Pascolini, D.; Etya'ale, D.; Kocur, I.; Pararajasegaram, R.; Pokharel, G. P.; Mariotti, S. P., Global data on visual impairment in the year 2002. Bull. W.H.O. 2004, 82, 844-851, Pascolini, D.; Mariotti, S. P., Global estimates of visual impairment: 2010. Br. J. Ophthalmol. 2012, 96 (5), 614).

Moreover, it is estimated that there are about 5 million visually disabled children in the world with a half of a million new cases each year. Therefore, the burden of corneal blindness on the societies arise not only from its high prevalence, but also from the young age, which can severely result in loss of productive years. This begs the scientific community attentions to explore new modalities to substitute the damaged cornea, through transplantation of engineered corneas to restore the vision.

The ideal biomaterial for restoration and regeneration of corneal defects would 1) be transparent to permit vision; 2) be biocompatible, promoting migration, growth and optimal phenotype of corneal cells; 3) have biomimetic mechanical properties similar to the human cornea, such as strength and elasticity, to adequately react to the intraocular pressure fluctuations while preserving refractive status; 4) have a strong adhesion to adjacent corneal tissue with long-term retention and biointegration, allowing chemical bonding between the adhesive and the cornea; 5) have a swelling ratio of <20% to preserve its shape and optical properties; 6) have biodegradative properties that match the time of tissue remodeling and regeneration; 7) possess appropriate porosity and diffusion for cell nutrients, while serve as a microbial barrier; and 8) have a cost-effective manufacturing process and 9) be easy to apply to the patient's eye (Grinstaff, M. W., Designing hydrogel adhesives for corneal wound repair. Biomaterials 2007, 28 (35), 5205-5214).

Various synthetic and natural based biomaterials such as cyanoacrylates (Leggat, P. A.; Smith, D. R.; Kedjarune, U., Surgical applications of cyanoacrylate adhesives: a review of toxicity. ANZ Journal of Surgery 2007, 77 (4), 209-213), polyethylene glycol (PEG) based materials (Grinstaff, M. W., Biodendrimers: New polymeric biomaterials for tissue engineering. Chemistry—A European Journal 2002, 8 (13), 2838-2846; Carnahan, M. A.; Middleton, C.; Kim, J.; Kim, T.; Grinstaff, M. W., Hybrid dendritic-linear polyester-ethers for in situ photopolymerization. Journal of the American Chemical Society 2002, 124 (19), 5291-5293) and fibrin glue (Alaminos, M.; Del Carmen Sanchez-Quevedo, M.; Munoz-Avila, J. I.; Serrano, D.; Medialdea, S.; Carreras, I.; Campos, A., Construction of a complete rabbit cornea substitute using a fibrin-agarose scaffold. Invest Ophthalmol Vis Sci 2006, 47 (8), 3311-7), have been recently used in ophthalmic surgery for filling corneal stromal defects and as substitutes for sutures to avoid suture's disadvantages, i.e prolonged surgery time, potential infections, inflammation, neovascularization, and possible astigmatism (Bhatia, S. S., Ocular surface sealants and adhesives. Ocul Surf 2006, 4 (3), 146-54).

However, while synthetic biomaterials fall short in terms of biocompatibility, cell adhesion and biointegration, the biological counterparts lack mechanical and adhesion properties. PEG-based adhesive can seal corneal incisions in cataract surgery; however, it is incapable of filling stromal defects, lacks cell adhesion and falls off within 3 days of application (Food and Drug Administration, ReSure® Sealant—P130004. 2014). Fibrin glue, on the other hand, lacks required mechanical properties and degrades quickly, and its application could be associated with viral infections, and immunological reactions (Jhanji, V.; Young, A. L.; Mehta, J. S.; Sharma, N.; Agarwal, T.; Vajpayee, R. B., Management of Corneal Perforation. Surv. Ophthalmol. 56 (6), 522-538). Cyanoacrylate is the adhesive used "off-label" in clinics for treating small corneal perforations (less than 3 mm in diameter) and some corneal melting processes; nevertheless, it also has several major shortcomings including low biocompatibility, lack of transparency, inability to degrade during the healing process and difficulties in handling (Rana, M.; Savant, V., A brief review of techniques used to seal corneal perforation using cyanoacrylate tissue adhesive. Cont Lens Anterior Eye 2013, 36 (4), 156-8).

In some aspects of the invention, the inventors have reported a synthesis of super elastic protein-based hydrogels with a strong adhesion to the surfaces of biological tissues, formed from grafting a functional crosslinkable moieties onto gelatin backbone. Gelatin is polydisperse protein produced from irreversible hydrolysis of collagen fibrils into smaller molecular weight polypeptides. Although the chemical composition of gelatin is similar to those of the parent collagen, it possesses better solubility and lesser antigenicity, compared to collagen, rendering it as an ideal scaffold for cellular attachment, proliferation, and matrix metalloproteinase targeted degradation. Despite development of various crosslinking strategies to generate hydrogel network, satisfactory mechanical and adhesion characteristics have yet to be realized. For instance, gelatin methacryloyl (GelMA), the most studied derivative of gelatin, demonstrated maximum elastic modulus and ultimate tensile strength of 180±34, 53±17 KPa, respectively, which are virtually 3 orders of magnitude lower than those of human tissues (i.e. 112.47±36.49 and 28.64±9.03 MPa, respectively). Lysine and hydroxyllysine constitute 5.1% of gelatin chemical structure, and are capable of functionalization through methacrylation approach. This confines the functionalization degree (FD) of the gelatin to 5.1%, and confines the crosslinking degree of hydrogel and its structural properties. Therefore, scaffolds made of GelMA show poor mechanical properties due to low degree of functionalization, which limits their biomedical application (Nichol, J. W.; Koshy, S. T.; Bae, H.; Hwang, C. M.; Yamanlar, S.;

Khademhosseini, A., Cell-laden microengineered gelatin methacrylate hydrogels. Biomaterials 2010, 31 (21), 5536-5544).

Thus, there remains a need in the art for compositions and methods for repairing soft tissue injuries and wounds. The present disclosure addresses some of these needs.

SUMMARY

The inventors have developed, inter alia, a novel biocompatible, easy-to-handle, light-crosslinkable, bioadhesive, that integrates within the collagen matrix of the cornea and sclera. The engineered scaffold is formed through covalent functionalization of gelatin with glycidyl methacrylate (hereafter referred as GELGYM) through an epoxide ring opening reaction, that leads to extension of the graft and installment of more functional groups in a highly-controlled manner that enables mechanically robust scaffolds under lower energy and intensity of light, in the safe and acceptable range of light wavelength and intensity for ocular applications.

Certain aspects of the present invention are directed to methods for treating a soft tissue injury or wound, comprising the steps of applying glycidyl methacrylate-substituted gelatin and a visible light activated photoinitiator to the injury; and applying visible light to activate the photoinitiator and cross-linking the glycidyl methacrylate-substituted gelatin.

Some embodiments of the present invention are directed to methods for treating a corneal defect, comprising the steps of: applying glycidyl methacrylate-substituted gelatin and a visible light activated photoinitiator to the defect; and applying visible light to activate the photoinitiator and cross-linking the glycidyl methacrylate-substituted gelatin.

The glycidyl methacrylate-substituted gelatin can be cross-linked prior to applying to the injury or wound. Accordingly, certain aspects of the present invention are directed to method for treating a soft tissue injury or wound, comprising applying a cross-linked glycidyl methacrylate-substituted gelatin to the soft tissue injury or wound. In some embodiments, the cross-linked glycidyl methacrylate substituted gelatin can be in form of a hydrogel.

As used herein, "glycidyl methacrylate-substituted gelatin" is gelatin having free amine and/or hydroxyl groups that have been substituted with at least one glycidyl methacrylate group. Gelatin comprises amino acids, some of which have side chains that terminate in amines (e.g., lysine, arginine, asparagine, glutamine) or hydroxyls (e.g., serine, threonine, aspartic acid, glutamic acid). One or more of these terminal amines and/or hydroxyls can be substituted with glycidyl methacrylate groups to produce glycidyl methacrylate-substituted gelatin. In some embodiments, with exposure to visible light in the presence of a photoinitiator, the glycidyl methacrylate groups on one gelatin molecule can react with the glycidyl methacrylate groups on another gelatin molecule to crosslink the gelatin and produce a hydrogel. In some embodiments, the gelatin is functionalized with glycidyl methacrylate groups by reacting gelatin with suitable reagents including, but not limited to, glycidyl methacrylate.

In some embodiments, the glycidyl methacrylate-substituted gelatin has a glycidyl methacrylate to amine ratio of between 0.2 and 35.

In some embodiments, the glycidyl methacrylate-substituted gelatin has a degree of functionalization of gelatin with glycidyl methacrylate between 5% and 180% with respect to amine groups of gelatin.

In some embodiments, the glycidyl methacrylate-substituted gelatin is applied in a composition having a glycidyl methacrylate-substituted gelatin concentration between 5% and 25% (w/v). For example, concentration of glycidyl methacrylate-substituted gelatin can be between 17% and 25% (w/v). In some embodiments, concentration of glycidyl methacrylate-substituted gelatin between 17% and 23% (w/v), between 5% and 15% (w/v), or between 8% and 12% (w/v). In some embodiments, concentration of glycidyl methacrylate-substituted gelatin is about 20% (w/v) or of about 10% (w/v).

Without limitations, one or a mixture of two or more different photoinitiators can be used. Further, for application to the injury or wound, the photoinitiator can be comprised in the composition comprising the glycidyl methacrylate-substituted gelatin or in a composition separate from the composition comprising the glycidyl methacrylate-substituted gelatin. Regardless of in which composition the photoinitiator is comprised in, concentration of the photoinitiator can range from 0.01 to 20% (w/v) or 0.01 mM to 20 mM. In some embodiments, the visible light is applied for a period between 30 seconds to 15 minutes.

In some embodiments, the cross-linked glycidyl methacrylate-substituted gelatin has a tensile strength of 0.05 to 2.5 MPa.

In some embodiments, the cross-linked glycidyl methacrylate-substituted gelatin has a compressive modulus of 0.01-0.75 MP.

In some embodiments, the cross-linked glycidyl methacrylate-substituted gelatin has a swelling ratio of less than 20%. In certain embodiments, the cross-linked glycidyl methacrylate-substituted gelatin has a swelling ratio of at least 20%.

In some embodiments, the cross-linked glycidyl methacrylate-substituted gelatin is permeable to gas and small molecules.

Some embodiments of various aspects of the invention comprise further administering a therapeutic agent. Exemplary therapeutic agents for inclusion in the compositions include, but are not limited to, an antibacterial, an antifungal, an anti-viral, an anti-acanthamoebal, an anti-inflammatory, an immunosuppressive, an anti-glaucoma, an anti-VEGF, a growth factor, or any combination thereof.

Some aspects of the present invention are directed to methods further comprising cross-linking a glycidyl methacrylate-substituted gelatin to form the cross-linked glycidyl methacrylate-substituted gelatin prior to applying to the soft tissue injury or wound.

In some embodiments, the cross-linked glycidyl methacrylate-substituted gelatin is substantially transparent. In some embodiments, the cross-linked glycidyl methacrylate-substituted gelatin further comprises corneal cells. Preferred corneal cells include endothelial cells, keratocytes, or a combination thereof. In some embodiments, the method does not comprise suturing the cornea.

BRIEF DESCRIPTION OF THE DRAWINGS

FIGS. 3a and 3b show H-NMR characterization of the GELGYM before and after crosslinking. FIG. 3c is a graph showing percentage of functionalization degree with respect to amine groups and pH of reaction. FIG. 3d is a graph showing percentage of functionalization degree with respect to amine groups and ratio of glycidyl methacrylate and amine.

FIG. 5a is a bar graph showing tensile modulus with respect to glycidyl methacrylate/amine ratio. FIG. 5b is a bar graph showing ultimate tensile with respect to glycidyl methacrylate/amine ratio. FIG. 5c is a bar graph showing energy at break with respect to glycidyl methacrylate/amine ratio. FIG. 5d is a bar graph showing elongation at break with respect to glycidyl methacrylate/amine ratio.

FIG. 6a is a line graph showing tensile modulus with respect to crosslinking time. FIG. 6b is a line graph showing ultimate tensile with respect to crosslinking time. FIG. 6c is a line graph showing energy at break with respect to crosslinking time. FIG. 6d is a line graph showing elongation at break with respect to crosslinking time.

FIG. 7a is a line graph showing tensile modulus with respect to GELGYM concentration. FIG. 7b is a line graph showing ultimate tensile with respect to GELGYM concentration. FIG. 7c is a line graph showing energy at break with respect to GELGYM concentration. FIG. 7d is a line graph showing elongation at break with respect to GELGYM concentration.

FIG. 8a is a line graph showing compressive modulus with respect to GELGYM concentration. FIG. 8b is a line graph showing compressive modulus with respect to glycidyl methacrylate/amine ratio.

FIG. 9a shows the application of 6 mm pre-crosslinked polymerized disc of GelGYM into 6 mm perforation acting as a corneal substitute. GELGYM has been also used as a bioadhesive to glue the polymerized disc of GelGYM to the host trephined cornea in a porcine ex vivo model.

FIG. 12a shows swelling behavior of GELGYM after varying light exposure (1-10 min), showing swelling ratio can be tuned from 10-90%. FIG. 12b shows degradation profile of GELGYM crosslinked with varying exposure of light (30 sec-5 min) after incubation in collagenase solution, including collagen crosslinked with EDC/NHS as control (scaffold previously used as a corneal substitute in human patients). The highly functionalized GELGYM with the concentration of 22.5% was used for this study.

FIG. 13a shows transmittance spectra (250-850 nm) of GELGYM discs (diameter of 5 mm and thickness of 1 mm) crosslinked with varying light exposure (1-10 min) followed by 30 min soaking in PBS. FIG. 13b shows glucose concentration changes as a function of time (h) in Franz Flow Cells with upper chamber filled with PBS and lower chamber filled with 2000 mg/dl glucose solution separated by crosslinked membranes of GELGYM with varying light exposure, compared to porcine cornea. The highly functionalized GELGYM with the concentration of 22.5% was used for these studies.

FIG. 14a-14d show representative Live/Dead images from keratocytes after 6 days in culture (Green [calcein AM]: lived cells, Red [ethidium homodimer-1]: dead cells). Scale bar: 200 μm. FIG. 14e are bar graphs showing quantification of metabolic activity using a PrestoBlue assay of keratocytes over 6 days of culture on top of different discs of GELGYM that have been polymerized using 3, 5 and 10 minutes of crosslinking-time, compared to cells growing on the tissue culture plate (TCP).

FIG. 15a-15d show representative Live/Dead images from epithelial cells after 6 days in culture (Green [calcein AM]: lived cells, Red [ethidium homodimer-1]: dead cells). Scale bar: 200 μm. FIG. 15e are bar graphs showing quantification of metabolic activity using a PrestoBlue assay of epithelial cells over 6 days of culture on top of different discs of GELGYM that have been polymerized using 3, 5 and 10 minutes of crosslinking-time, compared to cells growing on the tissue culture plate (TCP).

FIG. 16a-16d show representative Live/Dead images from progenitor cells after 6 days in culture (Green [calcein AM]: lived cells, Red [ethidium homodimer-1]: dead cells). Scale bar: 200 μm. FIG. 16e are bar graphs showing quantification of metabolic activity using a PrestoBlue assay of progenitor cells over 6 days of culture on top of different discs of GELGYM that have been polymerized using 3, 5 and 10 minutes of crosslinking-time, compared to cells growing on the tissue culture plate (TCP).

FIG. 20a are images showing retention evaluation of GEL-GYM after gluing two pieces of human corneoscleral limbus (n=6, using 6 different human donors), induced by 3 min light exposure. The two limbal pieces remained glued to each other after 6 months under culture conditions for all the donors used, represented by a survival curve. After that time, part of the glue has been degraded and human corneal keratocytes have migrated and repopulated the area, synthetizing and remodeling the extracellular matrix. FIG. 20b-20f are representative transmission electron microscopic images of the cross-sectional interface of tissue-glue after 6-month incubation in culture media.

FIG. 22a-22c show phase contrast microscopy images of limbal explants (*) glued and surrounded by GELGYM () after 1, 2 and 4 days in culture. Epithelium (*, white dashed line) rapidly proliferates and migrates onto GELGYM, leading to a complete confluent epithelium at day 4. FIG. 22d shows representative H&E histopathology and FIG. 22e-22f show TEM images of human corneoscleral limbal pieces glued with GELGYM, after 3 months under culture. Epithelial cells (1) migrate from the native tissue (2) and stratify onto GELGYM (3). Fibroblasts (4) migrate into GELGYM from the corneal stroma, promoting a regenerative response inside the scaffold.

FIG. 23a is an image showing applications of GELGYM in ophthalmology such as DALK, PK, and DMEK. FIG. 23b shows histological analysis of the GEL-GYM after in vivo application in deep anterior lamellar keratectomy in the rabbit model, demonstrating full epithelialization, migration of FB into GELGYM and biointegration. FIG. 23c shows lap shear set-up and FIG. 23d shows the adhesion strength of the GELGYM with different organs compared to the traditional suture.

FIG. 25a is a schematic showing chemical synthesis of GELGYM via grafting glycidyl methacrylate on the nucleophile moieties. FIG. 25b is a schematic showing its photo-induced crosslinking through the presence of eosin Y (E) (0.05 mM), triethanolamin (TEA) (0.04%) and vinyl caprolactam (VC) (0.04%) through radical reaction that forms 3-D network of hydrogel with strong interactions to the biological tissue surfaces. FIG. 25c shows H-NMR characterization of the GELGYM before (appearance of the olefinic ($\delta$=5.8-6.2 ppm) and methyl ($\delta$=1.9 ppm) hydrogens) and after crosslinking (disappearance of the olefinic hydrogens ($\delta$=5.8-6.2 ppm) and shift of the methyl hydrogens from ($\delta$=1.9 to 1.4 ppm). FIG. 25d is a line graph showing functionalization tuneability of GELGYM through varying the concentration of glycidyl methacrylate in the reaction. FIG. 25e is a line graph showing crosslinking reaction progress dependence on the crosslinking time, characterized by H-NMR.

FIG. 26a shows representative tensile stress/strain curves for GELGYM (22.5% w/v and crosslinked for 5 min) with varying functionalization degree (FD) and their corresponding mean tensile modulus (The inset demonstrates the unique elasticity of the GELGYM).

FIG. 27a are representative live-dead images of the corneal fibroblasts (HCF), corneal epithelial cells (HCEp), and corneal endothelial cells (HCEn) along with hybrid neuroblastoma cells (NPC) cultured onto GELGYM hydrogels (FD of 171% and 22.5% w/v) with varying CT from 3-10 min after 6-day incubation. FIG. 27b are bar graphs showing their corresponding cellular metabolic activity as a function of incubation time, indicated by the AlamarBlue assay. FIG. 27c are fluorescent immunostaining images of the cross-sectional interface of tissue-glue after 6-month incubation in culture media [Analysis of expression of CK 3/12 in HCEp (top), ALDH3A1 in HCF (middle), and $\alpha$-SMA in HCF (bottom) by immunohistochemistry. Positive signals are shown in green, and all cell nuclei are stained blue]. FIG. 27d is representative fluorescent immunostaining image of HCEn cells cultured on GELGYM after 6 days, indicating the expression of ZO-1 [Positive signals are shown in pink, and all cell nuclei are stained blue].

DETAILED DESCRIPTION

Figure 1:
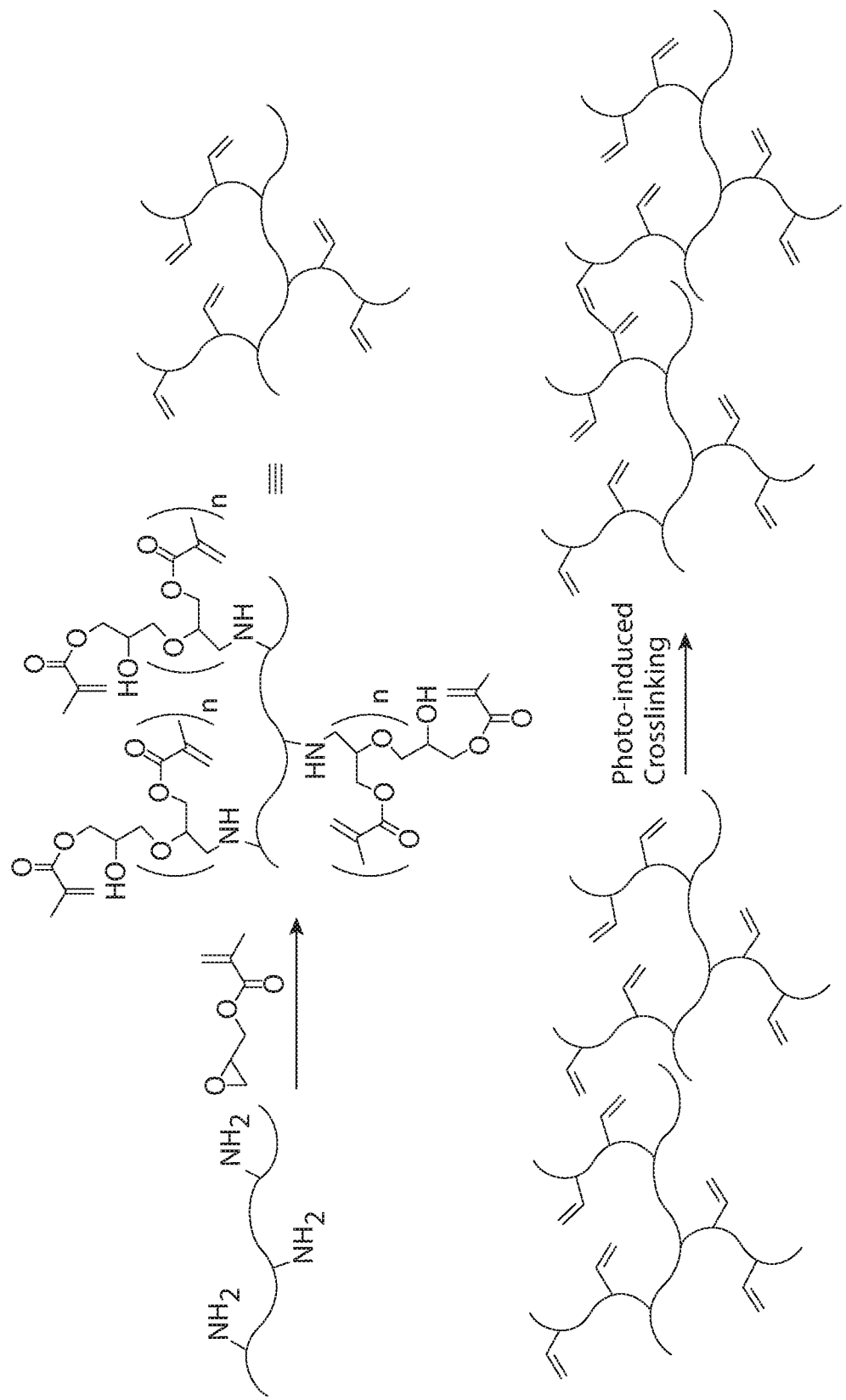
FIG. 1 is a schematic diagram showing synthesis of gelatin-based scaffold with varying degree of functionalization and characterization.

The inventors have developed a novel biocompatible, easy-to-handle, light-crosslinkable, bioadhesive, that integrates within the collagen matrix of the cornea and sclera. The engineered scaffold is formed through covalent functionalization of gelatin with glycidyl methacrylate through an epoxide ring opening reaction, that leads to extension of the graft and installment of more functional groups in a highly-controlled manner. The in vitro and ex vivo data showed that glycidyl methacrylate-substituted gelatin acts 1) as an adhesive sealant for corneal or corneoscleral lacerations facilitating an instant primary closure, and 2) as a corneal substitute to generate an immediate sutureless keratoplasty, without the need of a donor cornea.

The formulations developed by the inventors can act as bioadhesives for treating soft tissue injury or wound. To form these hydrogels, Gelatin was chemically functionalized with glycidyl methacrylate to form a light activated and adhesive hydrogel, with tunable physical properties. This hydrogel can be applied to the cornea and photopolymerized with visible light to form a highly adhesive hydrogel. Specific formulations were developed with desired flexibility, bioactivity and degradation profiles suitable for corneal applications.

The inventors have used graft polymerization to engineer a super-elastic, photo-induced crosslinkable, protein-based hydrogel with unique biomimetic properties, approaching those of the native tissue. While programmable, the hydrogel can be stretched up to 4 times of its initial length and withstand high tensile stresses up to 1.95 MPa and compressive strains as high as 80% without breaking. The hydrogel is also highly biocompatible, and supports the cellular adhesion, proliferation and migration in 2 and 3-dimensional cell-cultures. These characteristics along with its superb adhesion to the surface of biological tissues such as cornea, aorta, heart, muscle, kidney, liver and spleen suggests widespread applications of this hydrogel in many biomedical areas such transplantation, tissue adhesive, bioprinting, lab-on-a chip, drug and cell delivery.

Although widespread in biomedical applications, UV light crosslinking has potential biosafety concerns as it may lead to undesired DNA damage and ocular toxicity. With glycidyl methacrylate-substituted gelatin, the prepolymer solution can be crosslinked with appropriate initiation system upon exposure of the irradiation, where the irradiation wavelength matches the absorption of initiator. Moreover, glycidyl methacrylate-substituted gelatin intimately mimics some fundamental properties of native extracellular matrix (ECM) due to the presence of cell binding sites such as Arg-Gly-Asp, and matrix metalloproteinase responsive peptide motifs, allowing not only enhanced cell-hydrogel interaction, but also the greater cellular proliferation.

Therefore, the glycidyl methacrylate-substituted gelatin can be applied in two main forms of adhesive and scaffold, with and without incorporated cells for multiple applications. Natural extracellular matrix components may include gelatin derived from animals including, but not limited to, pig, cow, dog, horse, chicken, fish, etc. Advantageously, the gelatin can be harvested under sterile conditions from animals in pathogen-free barrier facilities to eliminate the risk of transmission of disease (e.g, hepatitis C, human immunodeficiency virus, etc.)

Certain aspects of the present invention are directed to methods for treating a soft tissue injury or wound, comprising the steps of applying a glycidyl methacrylate-substituted gelatin (GELGYM) and a visible light activated photoinitiator to the injury; and applying visible light to activate the photoinitiator and cross-linking the glycidyl methacrylate-substituted gelatin.

Generally, soft tissue includes all tissue of the body except bone. Examples of soft tissue include, but are not limited to, muscles, tendons, fibrous tissues, fat, blood vessels, nerves, and synovial tissues. As used herein, the term "wound" is used to describe skin wounds as well as tissue wounds. A skin wound is defined herein as a break in the continuity of skin tissue that is caused by direct injury to the skin. Several classes including punctures, incisions, excisions, lacerations, abrasions, atrophic skin, or necrotic wounds and burns generally characterize skin wounds. In some embodiments, the compositions and methods of the invention are useful for enhancing the healing of wounds of the skin, cornea, heart, liver, cartilage, bones, vascular system, spleen, kidney, stomach and intestinal wounds.

In some preferred embodiments, the wound is a cornea, heart, liver, spleen, kidney, stomach and intestinal wound. In yet another preferred embodiment, the soft tissue injury or wound is a corneal defect.

Some embodiments of the present invention are directed to methods for treating a corneal defect, comprising the steps of: applying glycidyl methacrylate-substituted gelatin and a visible light activated photoinitiator to the defect; and applying visible light to activate the photoinitiator and cross-linking the glycidyl methacrylate-substituted gelatin.

In some embodiments, the glycidyl methacrylate-substituted gelatin has a glycidyl methacrylate to amine ratio of between 0.2 and 35, between 2 and 32, or between 5 and 32. In some preferred embodiments, the glycidyl methacrylate-substituted gelatin has a glycidyl methacrylate to amine ratio of 32. In some embodiments of certain aspects of the invention, the glycidyl methacrylate-substituted gelatin has a degree of functionalization of gelatin with glycidyl methacrylate between 2.5% and 180%, between 20% and 170%, between 20% and 160%, between 50% and 180% with respect to amine groups of gelatin.

Certain exemplary embodiments of the present invention comprise a photoinitiator. "Photoinitiator" as used herein refers to any chemical compound, or a mixture of compounds, that decomposes into free radicals when exposed to light. Preferably, the photoinitiator produces free radicals when exposed to visible light. Exemplary ranges of visible light useful for exciting a visible light photoinitiator include green, blue, indigo, and violet. Preferably, the visible light has a wavelength in the range of 450-550 nm. In some embodiments, the wavelength is in the range of 490-530 nm. In some preferred embodiments, the wavelength is in the range of 500-520 nm and intensity is 20 m W/cm$^2$.

Generally, a light of any suitable wavelength can be used in the method of the invention. For example, the composition can be exposed to visible light with a wavelength in the range of 450 to 550 nm. Further, exposure to light can be for any desired duration of time. For example, the composition can be exposed to visible light for a time period between 30 seconds and 15 minutes. In some embodiments, the composition can be exposed to visible light for a time period between 30 seconds and 10 minutes, or between 1 minute and 10 minutes. In some embodiments, the composition can be exposed to visible light for a time period between 3 minutes and 10 minutes. In some embodiments, the composition can be exposed to visible light for a time period of about 1 minute, about 2 minutes, about 3 minutes, 5 minutes or about 10 minutes. In some preferred embodiments, the composition can be exposed to visible light for a time period of about 5 minutes.

Examples of photoinitiators include, but are not limited to, Eosin Y, triethanolamine, vinyl caprolactam, dl-2,3-diketo-1,7,7-trimethylnorcamphane (CQ), 1-phenyl-1,2- propadione (PPD), 2,4,6-trimethylbenzoyl-diphenylphosphine oxide (TPO), bis(2,6-dichlorobenzoyl)-(4-propylphenyl)phosphine oxide (Ir819), 4,4'-bis(dimethylamino)benzophenone, 4,4'-bi s(diethylamino) benzophenone, 2-chlorothioxanthen-9-one, 4-(dimethylamino)benzophenone, phenanthrenequinone, ferrocene, diphenyl(2,4,6 trimethylbenzoyl)phosphine oxide/2-hydroxy-2-methylpropiophenone (50/50 blend), dibenzosuberenone, (benzene) tricarbonylchromium, resazurin, resorufin, benzoyltrimethylgermane (Ivocerin®), derivatives thereof, combinations thereof, etc.

In some embodiments, the visible light activated photoinitiator is a mixture of two or more different photoinitiators. In some embodiments, the photoinitiator is a mixture of Eosin Y, triethanolamine, and vinyl caprolactam. In some embodiments, the concentration of Eosin Y is between 0.0125 and 0.5 mM, and/or the concentration of triethanolamine is between 0.05 and 1.5% (w/v), and/or the concentration of vinyl caprolactam is between 0.05 and 1.5% (w/v). In some embodiments, the concentration of Eosin Y is between 0.025 and 0.15 mM, and/or the concentration of triethanolamine is between 0.2 and 1.6% (w/v), and/or and the concentration of vinyl caprolactam is between 0.09 and 0.8% (w/v). In some embodiments, the concentration of Eosin Y is between 0.025 and 0.15 mM, and/or the concentration of triethanolamine is between 0.2 and 1.6% w/v, and/or the concentration of vinyl caprolactam is between 0.09 and 0.8% (w/v). In some embodiments, the concentration of Eosin Y is about 0.05 mM, the concentration of triethanolamine is about 0.4% (w/v), and the concentration of vinyl caprolactam is about 0.4% (w/v).

As used herein, the concentration of glycidyl methacrylate-substituted gelatin is defined as the weight of glycidyl methacrylate-substituted gelatin divided by the volume of solvent (w/v), expressed as a percentage. The solvent may be a pharmaceutically acceptable carrier. In some embodiments, the glycidyl methacrylate-substituted gelatin is present at a concentration between 5% and 25% (w/v), between 7.5% and 22.5% (w/v), between 17% and 23% (w/v), or about 20% (w/v). In some embodiments, the glycidyl methacrylate-substituted gelatin is present at a concentration 22.5% (w/v). The prepolymer concentration is defined as the concentration of glycidyl methacrylate-substituted gelatin prior to cross-linking, i.e the concentration of glycidyl methacrylate-substituted gelatin.

In some embodiments, the glycidyl methacrylate-substituted gelatin has a combination of any of the above degrees of glycidyl methacrylate substitution, any of the above crosslinking time and any of the above concentrations, e.g., a degree of glycidyl methacrylate substitution between 0.2 and 35, cross linking time between 30 seconds and 10 minutes and a concentration between 5% and 25% (w/v); a degree of glycidyl methacrylate substitution between 2 and 32, cross linking time between 1 minute and 10 minutes and a concentration between 7.5% and 25% (w/v). In some preferred embodiments, the concentration of glycidyl methacrylate-substituted gelatin is 22.5% with 5 minutes crosslinking time. In some preferred embodiments, the concentration of glycidyl methacrylate-substituted gelatin is 22.5% and the degree of glycidyl methacrylate substitution is 32. In some embodiments, the degree of glycidyl methacrylate substitution is 32 when 5 minutes cross linking time was used.

In some embodiments, the glycidyl methacrylate-substituted gelatin has a combination of any of the above degrees of glycidyl methacrylate substitution and any of the above crosslinking time. In some embodiments of various aspects of the invention, the glycidyl methacrylate-substituted gelatin has a combination of any of the above degrees of glycidyl methacrylate substitution and any of the above concentrations. In some embodiments, the glycidyl methacrylate-substituted gelatin has a combination of any of the above concentrations and any of the above crosslinking time.

Some aspects of the invention provide formulations of glycidyl methacrylate-substituted gelatin and a visible light activated photoinitiator. In some embodiments, glycidyl methacrylate-substituted gelatin and the visible light activated photoinitiator are formulated in same formulation. For example, glycidyl methacrylate-substituted gelatin, Eosin Y, triethanolamine and vinyl caprolactam are formulated in same formulation. In various embodiments, the glycidyl methacrylate-substituted gelatin and the visible light activated photoinitiator are formulated in separate formulations.

In various embodiments, the glycidyl methacrylate-substituted gelatin and the visible light activated photoinitiator are applied at the same time. In some embodiments, the visible light activated photoinitiator is applied prior to applying the glycidyl methacrylate-substituted gelatin. In some embodiments, the visible light activated photoinitiator is applied after applying the glycidyl methacrylate-substituted gelatin.

Certain exemplary embodiments of the present invention comprise a pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation and is compatible with administration to a subject, for example a human. It must also be suitable for use in contact with any tissues or organs with which it may come in contact, meaning that it must not carry a risk of toxicity, irritation, allergic response, immunogenicity, or any other complication that excessively outweighs its therapeutic benefits. Examples of pharmaceutically acceptable carriers include, but are not limited to, a solvent or dispersing medium containing, for example, water, pH buffered solutions (e.g., phosphate buffered saline (PBS), HEPES, TES, MOPS, etc.), isotonic saline, Ringer's solution, polyol (for example, glycerol, propylene glycol, liquid polyethylene glycol, and the like), alginic acid, ethyl alcohol, and suitable mixtures thereof. In some embodiments, the pharmaceutically acceptable carrier can be a pH buffered solution (e.g. PBS) or water.

Corneal cells may be incorporated in or on the surface of the bioadhesive in order to promote corneal tissue formation and healing. Thus, in some embodiments, the glycidyl methacrylate substituted gelatin further comprises corneal cells, preferably epithelial cells, endothelial cells, keratocytes, or a combination thereof. Epithelial and/or endothelial cells are preferably seeded on the surface of the composition, while keratocytes are preferably mixed into the composition prior to photopolymerization.

In order to promote healing and regrowth of the cornea, to prevent or treat infections or immune response, to prevent or treat corneal vessel formation, to treat increased intraocular pressure, or to promote general eye health, the compositions of the present invention may further comprise a therapeutic agent. Non-limiting examples of therapeutic agents include an antibacterial, an anti-fungal, an anti-viral, an anti-acanthamoebal, an anti-inflammatory, an immunosuppressive, an anti-glaucoma, an anti-VEGF, a growth factor, or any combination thereof. Non-limiting examples of antibacterial agents include: penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim sulfamethoxazole, chitosan, ansamycins, daptomycin, nitrofurans, oxazolidinones, bacitracin, colistin, polymixin B, and clindamycin. Non-limiting examples of anti-fungal agents include: amphotericin B, natamycin, candicin, filipin, hamycin, nystatin, rimocidin, voriconazole, imidazoles, triazoles, thiazoles, allylamines, echinocandins, benzoic acid, ciclopirox, flucytosine, griseofulvin, haloprogin, tolnaftate, undecylenic acid, and povidone-iodine. Non-limiting examples of anti-viral agents include: acyclovir, valacyclovir, famciclovir, penciclovir, trifluridine, and vidarabine. Non-limiting examples of anti-acanthamoebal agents include: chlorohexidine, polyhexamethylen biguanide, propamidine, and hexamidine. Non-limiting examples of anti-inflammatory agents include: corticosteroids; non-steroidal anti-inflammatory drugs including salicylates, propionic acid derivatives, acetic acid derivatives, enolic acid derivatives, anthranilic acid derivatives, selective cox-2 inhibitors, and sulfonanilides; biologicals including antibodies (such as tumor necrosis factor-alpha inhibitors) and dominant negative ligands (such as interleukin-1 receptor antagonists). Non-limiting examples of immunosuppressive agents include: alkylating agents, antimetabolites, mycophenolate, cyclosporine, tacrolimus, and rapamycin. Non-limiting examples of anti-glaucoma agents include: prostaglandin analogs, beta blockers, adrenergic agonists, carbonic anhydrase inhibitors, parasympathomimetic (miotic) agents. Non-limiting examples of anti-vascular endothelial growth factor (anti-VEGF) agents include: bevacizumab, ranibizumab, and aflibercept. Non-limiting examples of growth factors include: epidermal growth factor, platelet-derived growth factor, vitamin A, fibronectin, annexin a5, albumin, alpha-2 macroglobulin, fibroblast growth factor b, insulin-like growth factor-I, nerve growth factor, and hepatocyte growth factor.

Certain aspects of the present invention are directed to a method for treating a soft tissue injury or wound, comprising, applying a cross-linked glycidyl methacrylate-substituted gelatin to the soft tissue injury or wound. A cross-linked glycidyl methacrylate-substituted gelatin is also known as glycidyl methacrylate-substituted gelatin hydrogel. As used herein, hydrogels are three-dimensional network of crosslinked-polymer, engineered to structurally and biologically support cellular proliferation, migration and tissue formation.

Some embodiments of the present invention are directed to methods further comprising cross-linking a glycidyl methacrylate-substituted gelatin to form the cross-linked glycidyl methacrylate-substituted gelatin prior to applying to the soft tissue injury or wound. For example, the glycidyl methacrylate-substituted gelatin hydrogel can be formed prior to applying to the corneal defect.

The mechanical properties of crosslinked glycidyl methacrylate-substituted gelatin can be tuned for various applications by changing the degree of glycidyl methacrylate substitution, concentration, amount of photoinitiators, and light exposure time. In some embodiments of certain aspects of the invention, the glycidyl methacrylate-substituted gelatin has a degree of functionalization of gelatin with glycidyl methacrylate between 2.5% and 180%, between 20% and 170%, between 20% and 160%, between 50% and 180% with respect to amine groups of gelatin.

The physical properties (degradation and mechanical properties, etc.) of glycidyl methacrylate-substituted gelatin hydrogel can be modified so that different compositions of the bioadhesive can be made for different purposes. The mechanical properties of glycidyl methacrylate-substituted gelatin hydrogel such as tensile strength, compressive modulus, swelling ratio and permeability, etc. can be tuned for various applications by changing the functionalization degree, visible light exposure time and prepolymer concentration. The following are desired physical properties, either alone or in combination, for bioadhesive compositions suitable for treating a soft tissue injury. In some embodiments, the soft tissue injury is corneal defect. In some embodiments, the composition has a tensile strength of 0.03-2.5 MPa, 0.075-2.4 MPa, or 0.1-2.3 MPa. In some embodiments, the composition has a compressive modulus of 0.001-0.75 MPa, 0.03-0.6 MPa or 0.05-0.5 MPa. In some embodiments, the composition has a swelling ratio of at least 5%, 10%, 20%, 30%, 40%, 50%, 60%, 70%, 80%, 100%, 120%, 150%, 175%, 190% or 200%. In some embodiments, the composition has a swelling ratio of less than 20%. In some embodiments, the swelling ratio is tunable from 20 to 190% of original size of the glycidyl methacrylate substituted gelatin hydrogel (longer crosslinking time leads to lower swelling ratio).

By varying crosslinking time and concentration of glycidyl methacrylate substituted gelatin, GELGYM hydrogels with a wide range of mechanical properties, with the tensile moduli of ranging from 0.03 to 2.5 MPa, ultimate tensile of 0.074 to 2.05 MPa, toughness of 0.076 to 1.71 MPa and elasticity of 210-410% were synthesized according to biomedical needs. In some embodiments, the hydrogel can be stretched up to 4 times of its initial length and withstand high tensile stress up to 1.95 MPa and compressive strains as high as 80% without breaking.

Selective permeability allows control of which molecules can pass through the pores of the membrane. Selective permeable membranes only allow small molecules such as glucose, amino acids to readily pass through, and inhibits larger molecules like protein, starch, from passing through it. In some embodiments, the cross-linked glycidyl methacrylate-substituted gelatin is permeable to gas and small molecules. In some embodiments, the cross-linked glycidyl methacrylate-substituted gelatin is permeable to glucose. In some embodiments, the cross-linked glycidyl methacrylate-substituted gelatin is substantially transparent.

Glycidyl methacrylate-substituted gelatin can have several uses in Ophthalmology. For example, it can be used as corneal substitute, avoiding the use of a donor cornea in any type of keratoplasty. It can also be used as a corneal filler in procedures such as corneal melting or corneal ulcers where there is a lack of corneal tissue. Glycidyl methacrylate-substituted gelatin can replace treatments applied in these conditions such as fibrin glue or amniotic membrane graft, which are usually in non-penetrating cases. Moreover, glycidyl methacrylate-substituted gelatin can be applied in penetrating cases where there is an open globe. In this condition, if the diameter of the penetrating lesion is less than 3 mm, cyanoacrylate-based glue can be applied to seal the defect, and if the lesion is bigger, usually a graft has to be applied. Glycidyl methacrylate-substituted gelatin can replace these treatments because it can directly solve any type of lesion, partial or full-thickness lesions, independently of the diameter.

Glycidyl methacrylate-substituted gelatin can also act as a glue or bioadhesive that seals any type of incision in the anterior segment of the eye, replacing the need of sutures in ocular surgery. Thus, glycidyl methacrylate-substituted gelatin would avoid suture's disadvantages: prolonged surgery time, potential infections, inflammation, neovascularization, and possible astigmatism. In this regard, the previous described uses of glycidyl methacrylate-substituted gelatin can be applied without performing sutures. In some embodiments, the method does not comprise suturing the cornea.

Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Other than in the operating examples, or where otherwise indicated, all numbers expressing quantities of ingredients or reaction conditions used herein should be understood as modified in all instances by the term "about." The term "about" when used to described the present invention, in connection with percentages means±1%, ±1.5%, ±2%, ±2.5%, ±3%, ±3.5%, ±4%, ±4.5%, or ±5%.

The singular terms "a," "an," and "the" include plural referents unless context clearly indicates otherwise. Similarly, the word "or" is intended to include "and" unless the context clearly indicates otherwise.

As used herein the terms "comprising" or "comprises" means "including" or "includes" and are used in reference to compositions, methods, systems, and respective component (s) thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment.

The abbreviation, "e.g." is derived from the Latin exempli gratia, and is used herein to indicate a non-limiting example. Thus, the abbreviation "e.g." is synonymous with the term "for example."

As used herein, the term "hydrogel" refers to a three-dimensional polymeric structure that is insoluble or minimally soluble in water or some other liquid but which is capable of absorbing and retaining large quantities of water or some other liquid to form a stable, often soft and pliable, structure.

As used herein, the term "biodegradable" describes a material which can decompose partially or fully under physiological conditions into breakdown products. The material under physiological conditions can undergo reactions or interactions such as hydrolysis (decomposition via hydrolytic cleavage), enzymatic catalysis (enzymatic degradation), and mechanical interactions. As used herein, the term "biodegradable" also encompasses the term "bioresorbable," which describes a substance that decomposes under physiological conditions, breaking down to products that undergo bioresorption into the host-organism, namely, become metabolites of the biochemical systems of the host organism. For example, a material is biodegradable if at least 10%, at least 20%, at least 30%, at least 40%, or more preferably, at least 50%, at least 60%, at least 70%, at least 80%, at least 90% of the material can decompose under physiological conditions within a desired period of time, such as on the order of minutes, hours, days, weeks, or months, depending on the exact material.

As used herein, the term "scaffold" refers to tissue patch for wide range of biomedical applications, including eye, skin, heart, liver, cartilage, tendon, intestine, bones, vascular system, spleen, kidney, stomach and intestine, and can be attached to the tissue through its prepolymer form, without the need for any adhesive or suture.

As used herein, the term "physiological conditions" refer to conditions of temperature, pH, osmotic pressure, osmolality, oxidation and electrolyte concentration in vivo in a human patient or mammalian subject at the site of administration, or the site of action. For example, physiological conditions generally mean pH at about 6 to 8 and temperature of about 37° C. in the presence of serum or other body fluids.

As used herein, the term "biocompatible" denotes being biologically compatible by not producing a toxic, injurious, or immunological response in living tissue.

As used herein, "bioadhesive" is natural polymeric material that can act as adhesive. Bioadhesives are generally useful for biomedical applications involving skin, cornea or other soft tissue. The bioadhesive described in the invention comprise gelatin functionalized with glycidyl methacrylate.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, rabbits, deer, bison, buffalo, goats, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "individual," "patient," "subject," and the like are used interchangeably herein. The terms do not denote a particular age, and thus encompass adults, children, and newborns. A subject can be a male or female.

As used herein, the term "administer" refers to the placement of a composition into a subject by a method or route which results in at least partial localization of the composition at a desired site such that desired effect is produced.

Preferably, the subject is a mammal. The mammal can be a human, non-human primate, mouse, rat, dog, cat, horse, or cow, but is not limited to these examples. Mammals other than humans can be advantageously used as subjects in animal models of human treatment or disease. In addition, the methods and compositions described herein can be used for treatment of domesticated animals and/or pets. A human subject can be of any age, gender, race or ethnic group. In some embodiments, the subject can be a patient or other subject in a clinical setting. In some embodiments, the subject can already be undergoing treatment.

As used herein, the terms "treat," "treatment," "treating," or "amelioration" are used herein to characterize a method or process that is aimed at (1) delaying or preventing the onset of a disease or condition; (2) slowing down or stopping the progression, aggravation, or deterioration of the symptoms of the disease or condition; or (3) bringing about ameliorations of the symptoms of the disease or condition. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also slowing of progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased morbidity or mortality. The term "treatment" of a disease also includes providing relief from the symptoms or side-effects of the disease (including palliative treatment). A treatment can be administered prior to the onset of the disease, for a prophylactic or preventive action. Alternatively or additionally, the treatment can be administered after initiation of the disease or condition, for a therapeutic action.

As used herein, the term "soft tissue" includes all tissue of the body except bone. Examples of soft tissue include, but are not limited to, muscles, tendons, fibrous tissues, fat, blood vessels, nerves, and synovial tissues.

As used herein, the term "wound" is used to describe skin wounds as well as tissue wounds. A skin wound is defined herein as a break in the continuity of skin tissue that is caused by direct injury to the skin. Several classes including punctures, incisions, excisions, lacerations, abrasions, atrophic skin, or necrotic wounds and burns generally characterize skin wounds. In some embodiments, the compositions and methods of the invention are useful for enhancing the healing of wounds of the skin, cornea, heart, liver, cartilage, bones, vascular system, spleen, kidney, stomach and intestinal wounds. The terms "injury", "wound" and "defect" have been used interchangeably herein.

The terms "bioactive agent" and "biologically active agent" are used herein interchangeably. They refer to compounds or entities that alter, inhibit, activate or otherwise affect biological events.

The term "cross-link" refers to a bond that links one polymer to another. These links can be covalent bond or ionic bonds and the polymers can be either synthetic polymers or natural polymers. When a synthetic polymer is cross-linked, the entire bulk of the polymer has been exposed to the cross-linking method.

The term "crosslinking" is process of forming covalent bonds or relatively short sequences of chemical bonds to join two polymer chains together.

It is noted that the invention provides an improved bioadhesive for repair and reconstruction of defects and injuries to the cornea. Advantageously, the bioadhesives of the present invention are low cost, easy to produce, and easy to use, making them a promising substance to be used for corneal repair, as well as an easily tunable platform to further optimize the adhesive characteristics.

Strong adhesion of glycidyl methacrylate-substituted gelatin to wet and dynamic biological surfaces, renders its application not only for the eye, but also for skin, heart, liver, cartilage, tendon, intestine, bones, vascular system and many other organs and tissues. Besides providing strong attachment and air/water-tight sealing, it offers regenerative properties that facilitate its biointegration. Moreover, it can replace sutures and eliminate their complications. Additionally, it can be applied in conjunction with suture to offer its superb sealing properties.

As a scaffold, it can be used as a tissue patch for wide range of biomedical applications, including all the organs previously mentioned, and can be attached to the tissue through its prepolymer form, without the need for any adhesive or suture. The biocompatibility, high glucose diffusion and controllable porosity and mechanical properties allows to incorporate cells into the scaffold. This allows to deliver cells to the damaged area using glycidyl methacrylate-substituted gelatin as a bioengineered patch loaded with cells of interest.

Light crosslinking capability also allows to generate microfabricated constructs using various approaches comprising micromolding, photomasking, bioprinting, selfassembly, and microfluidic techniques to constitute structures with controlled architectures. This enables to extent the functions of this hydrogel for targeted and programmable drug delivery, cell deliver, lab on a chip, and biosensing and many other applications where contemporary scaffolds fall short.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

The present invention can further be described in the following numbered paragraphs:

1. A method for treating a soft tissue injury or wound, comprising:
   a. applying a glycidyl methacrylate-substituted gelatin and a visible light activated photoinitiator to the injury; and
   b. applying visible light to activate the photoinitiator and cross-linking the glycidyl methacrylate-substituted gelatin.

2. The method of paragraph 1, wherein the soft tissue injury or wound is selected from the group consisting of muscles, tendons, ligaments, fascia, nerves, fibrous tissues, fat, blood vessels, synovial membranes, skin, cornea, heart, liver, cartilage, bones, vascular system, spleen, kidney, stomach and intestinal wounds.

3. The method of any of the preceding paragraphs, wherein the soft tissue injury or wound is a corneal defect.

4. The method of any of the preceding paragraphs, wherein the glycidyl methacrylate-substituted gelatin and the visible light activated photoinitiator are formulated in same formulation.

5. The method of any of the preceding paragraphs, wherein the glycidyl methacrylate-substituted gelatin and the visible light activated photoinitiator are formulated in separate formulations.

6. The method of any of the preceding paragraphs, wherein the glycidyl methacrylate-substituted gelatin and the visible light activated photoinitiator are applied at the same time.

7. The method of any of the preceding paragraphs, wherein the visible light activated photoinitiator is applied prior to or after applying the glycidyl methacrylate-substituted gelatin.

8. The method of any of the preceding paragraphs, wherein the glycidyl methacrylate-substituted gelatin has a glycidyl methacrylate to amine ratio of between 0.2 and 35.

9. The method of any of the preceding paragraphs, wherein the glycidyl methacrylate-substituted gelatin has a degree of functionalization of gelatin with glycidyl methacrylate between 5% and 180% with respect to amine groups of gelatin.

10. The method of any of the preceding paragraphs, wherein the glycidyl methacrylate-substituted gelatin is applied in a composition having a glycidyl methacrylate-substituted gelatin concentration between 5% and 25% (w/v).

11. The method of any of the preceding paragraphs, wherein the visible light activated photoinitiator is a mixture of two or more different photoinitiators.

12. The method of any of the preceding paragraphs, wherein the visible light is applied for a period between 30 seconds to 15 minutes.

13. The method of any of the preceding paragraphs, wherein the cross-linked glycidyl methacrylate-substituted gelatin has a tensile strength of 0.05 to 2.5 MPa.

14. The method of any of the preceding paragraphs, wherein the cross-linked glycidyl methacrylate-substituted gelatin has a compressive modulus of 0.01-0.75 MPa.

15. The method of any of the preceding paragraphs, wherein the cross-linked glycidyl methacrylate-substituted gelatin has a swelling ratio of less than 20%.

16. The method of any of the preceding paragraphs, wherein the cross-linked glycidyl methacrylate-substituted gelatin has a swelling ratio of at least 5%.

17. The method of any of the preceding paragraphs, wherein the wherein the cross-linked glycidyl methacrylate-substituted gelatin is permeable to gas or small molecules.

18. The method of any of the preceding paragraphs, wherein the cross-linked glycidyl methacrylate-substituted gelatin is substantially transparent.

19. The method of any of the preceding paragraphs, further comprising administering a therapeutic agent to the soft tissue injury or wound.

20. The method of any of the preceding paragraphs, wherein the method does not comprise a step of suturing.

21. A method for treating a soft tissue injury or wound, comprising:
applying a cross-linked glycidyl methacrylate-substituted gelatin to the soft tissue injury or wound.

22. The method of any of the preceding paragraphs, wherein the soft tissue injury or wound is selected from the group consisting of muscles, tendons, ligaments, fascia, nerves, fibrous tissues, fat, blood vessels, synovial membranes, skin, cornea, heart, liver, cartilage, bones, vascular system, spleen, kidney, stomach and intestinal wounds.

23. The method of any of the preceding paragraphs, wherein the soft tissue injury or wound is a corneal defect.

24. The method of any of the preceding paragraphs, wherein the cross-linked glycidyl methacrylate-substituted gelatin has a glycidyl methacrylate to amine ratio of between 0.2 and 35.

25. The method of any of the preceding paragraphs, wherein the cross-linked glycidyl methacrylate-substituted gelatin has a degree of functionalization of gelatin with glycidyl methacrylate is between 5% and 180% with respect to amine groups of gelatin.

26. The method of any of the preceding paragraphs, wherein the cross-linked glycidyl methacrylate-substituted gelatin is prepared from a solution comprising glycidyl methacrylate-substituted gelatin at a concentration between 5% and 25% (w/v).

27. The method of any of the preceding paragraphs, wherein the cross-linked glycidyl methacrylate-substituted gelatin has a tensile strength of 0.05 to 2.5 MPa.

28. The method of any of the preceding paragraphs, wherein the cross-linked glycidyl methacrylate-substituted gelatin has a compressive modulus of 0.01-0.75 MPa.

29. The method of any of the preceding paragraphs, wherein the cross-linked glycidyl methacrylate-substituted gelatin has a swelling ratio of less than 20%.

30. The method of any of the preceding paragraphs, wherein the cross-linked glycidyl methacrylate-substituted gelatin has a swelling ratio of at least 5%.

31. The method of any of the preceding paragraphs, wherein the wherein the cross-linked glycidyl methacrylate-substituted gelatin is permeable to gas and small molecules.

32. The method of any of the preceding paragraphs, wherein the cross-linked glycidyl methacrylate-substituted gelatin is substantially transparent.

33. The method of any of the preceding paragraphs, wherein the cross-linked glycidyl methacrylate-substituted gelatin further comprises a therapeutic agent.

34. The method of any of the preceding paragraphs, wherein the cross-linked glycidyl methacrylate-substituted gelatin further comprises a cell.

35. The method of any of the preceding paragraphs, wherein the method does not comprise a step of suturing.

36. The method of any of the preceding paragraphs, wherein the method further comprises cross-linking a glycidyl methacrylate-substituted gelatin to form the cross-linked glycidyl methacrylate-substituted gelatin prior to applying to the soft tissue injury or wound.

EXAMPLES

The disclosure is further illustrated by the following examples which should not be construed as limiting. The examples are illustrative only, and are not intended to limit, in any manner, any of the aspects described herein. The following examples do not in any way limit the invention.

Example 1: Mechanical Properties of GELGYM

Figure 2:
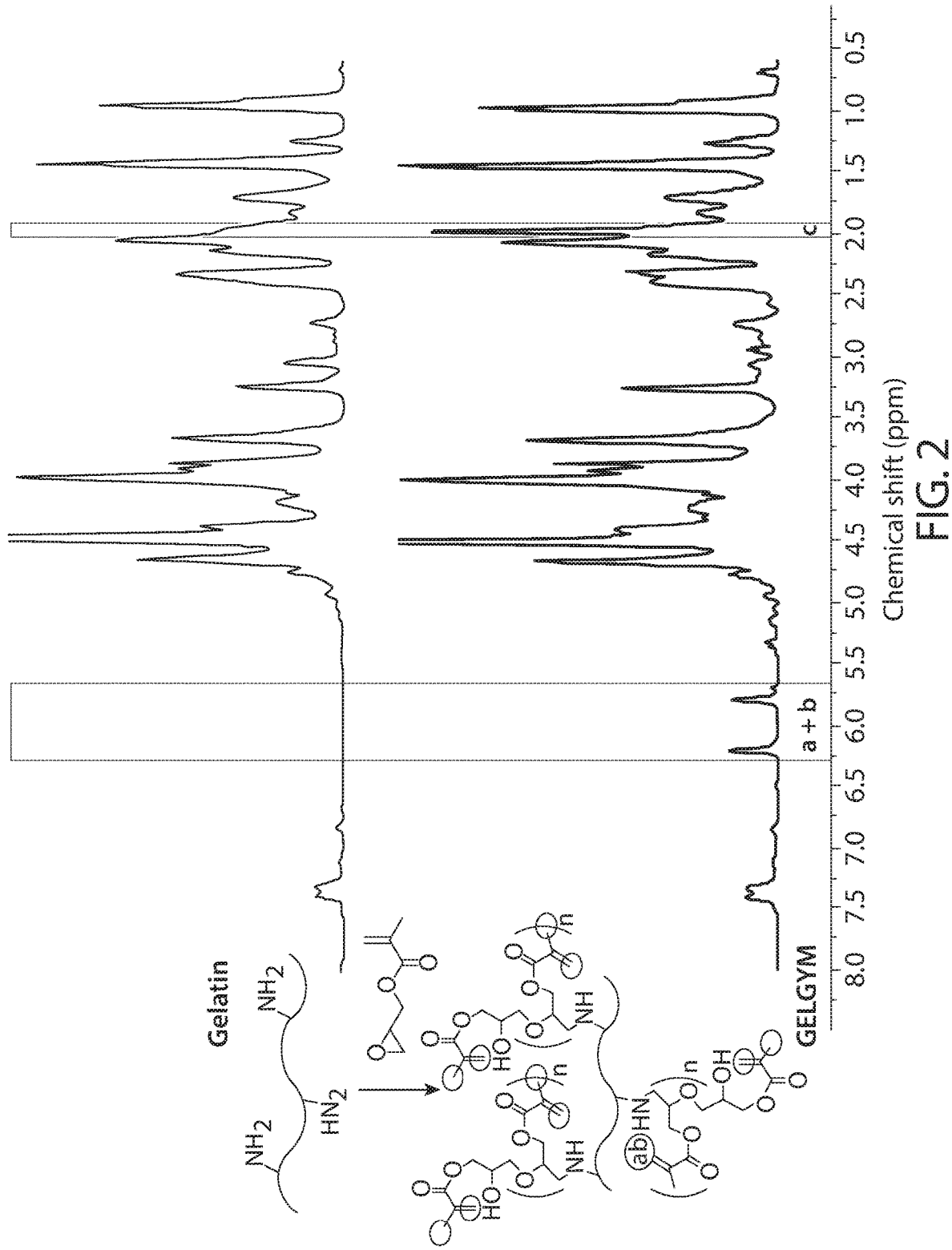
FIG. 2 is $^1$H-NMR spectra showing chemical characterization of GELGYM. The appearance of the a, b and c peaks in the olefinic and aliphatic regions confirms the synthesis of gelatin glycidyl methacrylate. Comparing a+b integral with the aromatic hydrogens (7.3-7.5 ppm) allows to assess the functionalization degree of gelatin.
Figure 3A:
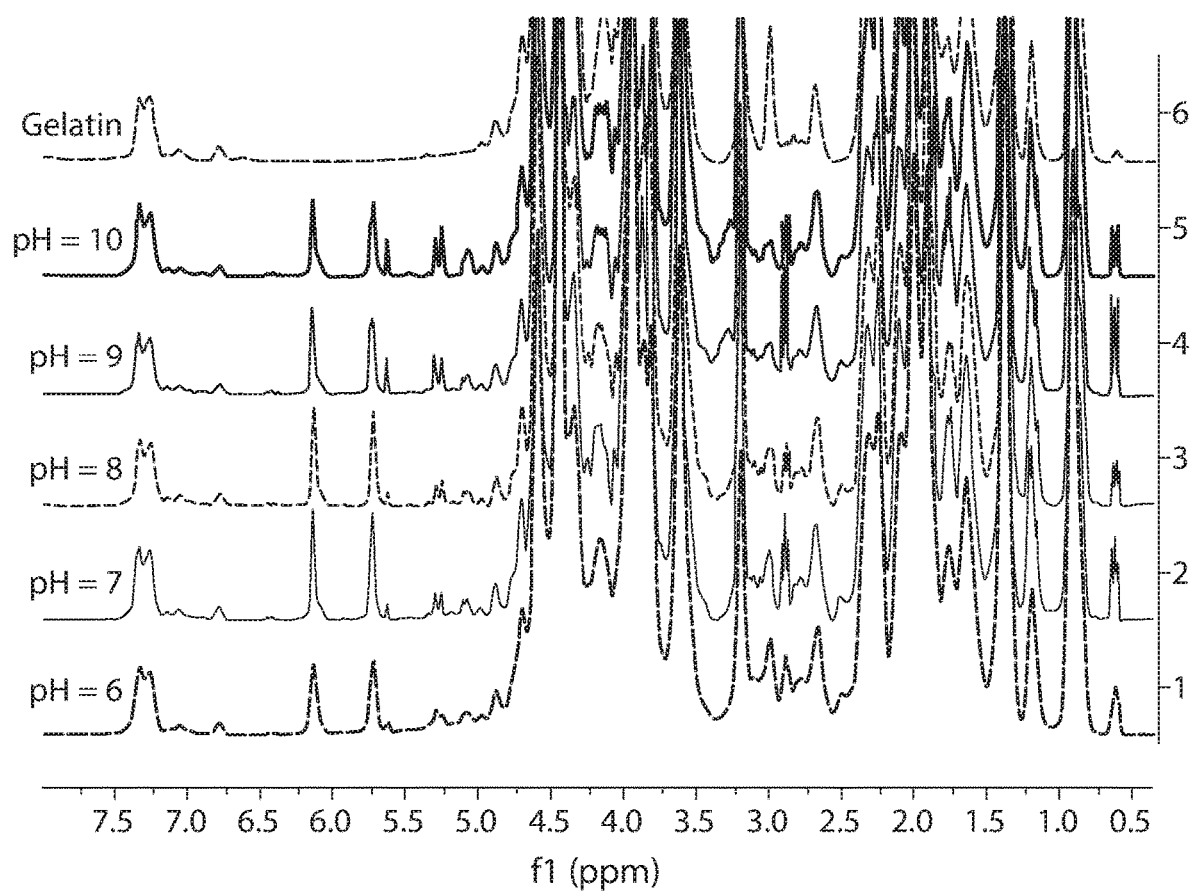
FIG. 3a-3d show chemical characterization of GELGYM.
Figure 3B:
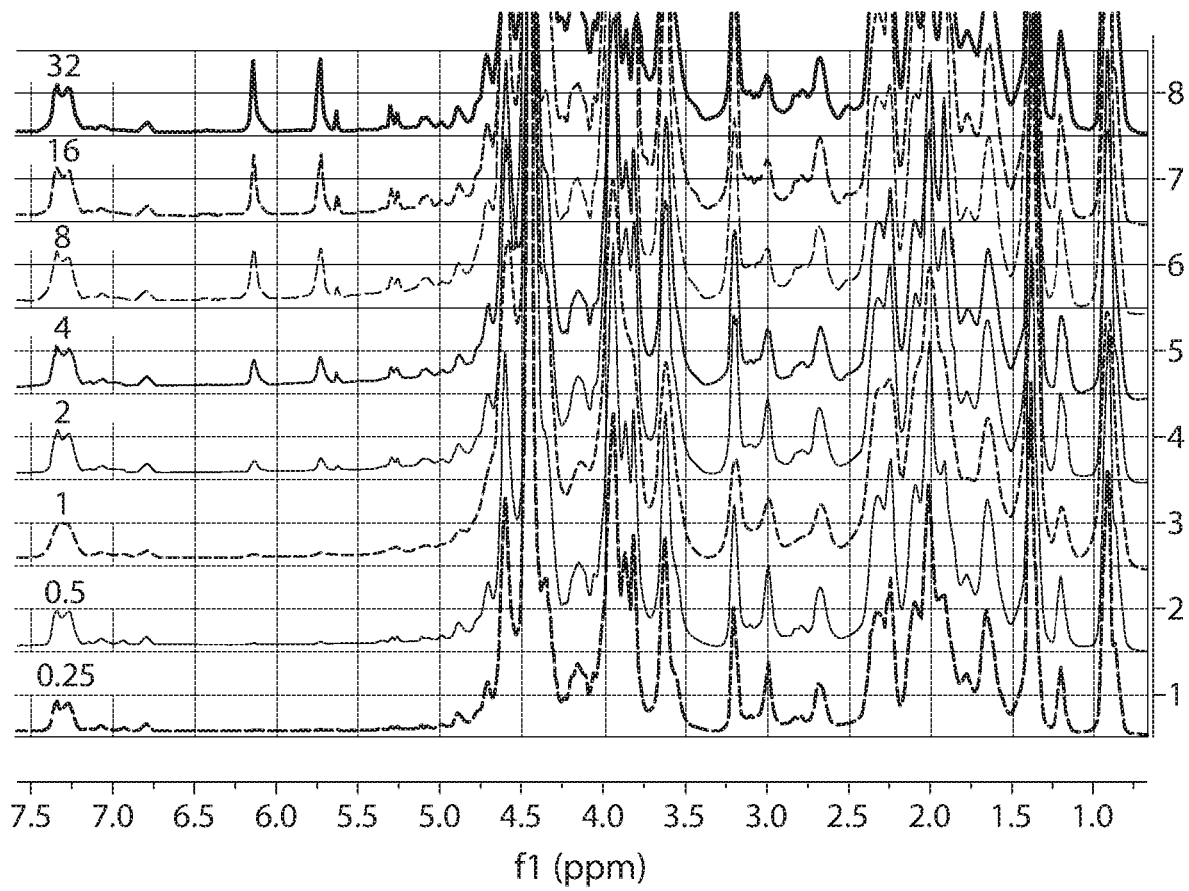
Figure 3C:
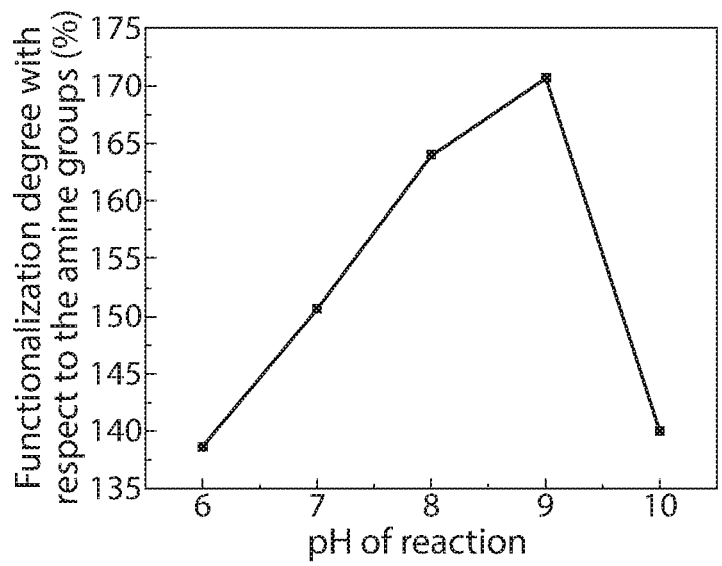
Figure 3D:
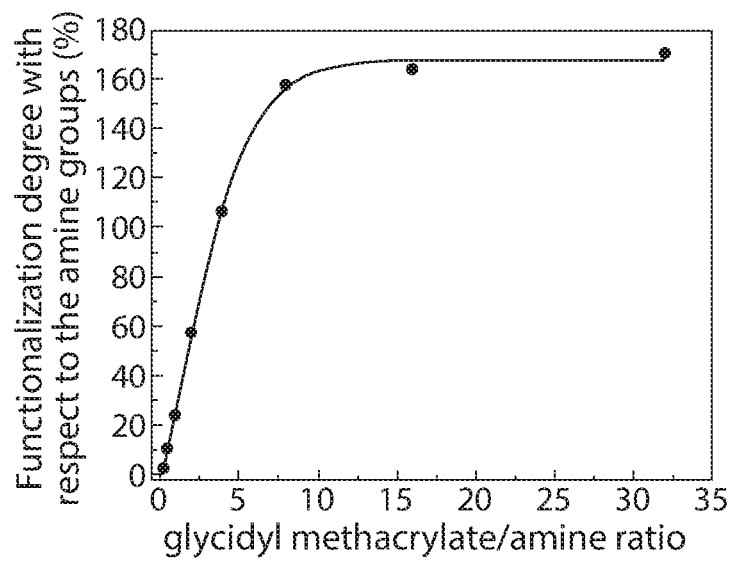
Figure 4A:
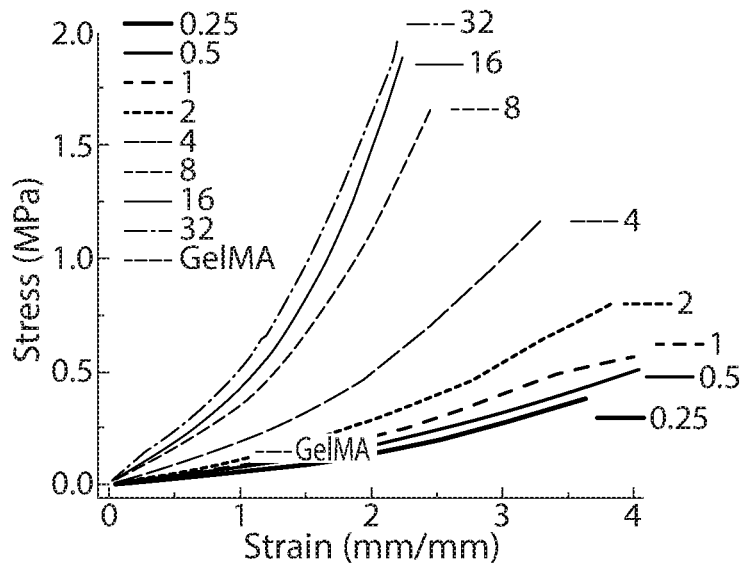
FIG. 4a-4f are graphs showing mechanical properties of GELGYM. Stress-strain curves (FIG. 4a-4c) and compressive modulus (FIG. 4d-4e) of GELGYM for varying functionalization degree (0.25 to 32), crosslinking time (1-10 min) and prepolymer concentration (7.5-22.5%). The tensile strength and modulus can be tuned from 0.1-2.3 MPa and 0.15-1.3 MPa respectively, with an excellent elongation up to 4 times. The concentration of GELGYM was 22.5% with 5 min crosslinking time in (FIG. 4a) and (FIG. 4d). Highest degree of functionalization (32) with the concentration of 22.5% were used for (FIG. 4b) and (FIG. 4e). Highest degree of functionalization (32) and 5 min crosslinking were used for (FIG. 4c) and (FIG. 4f).
Figure 4B:
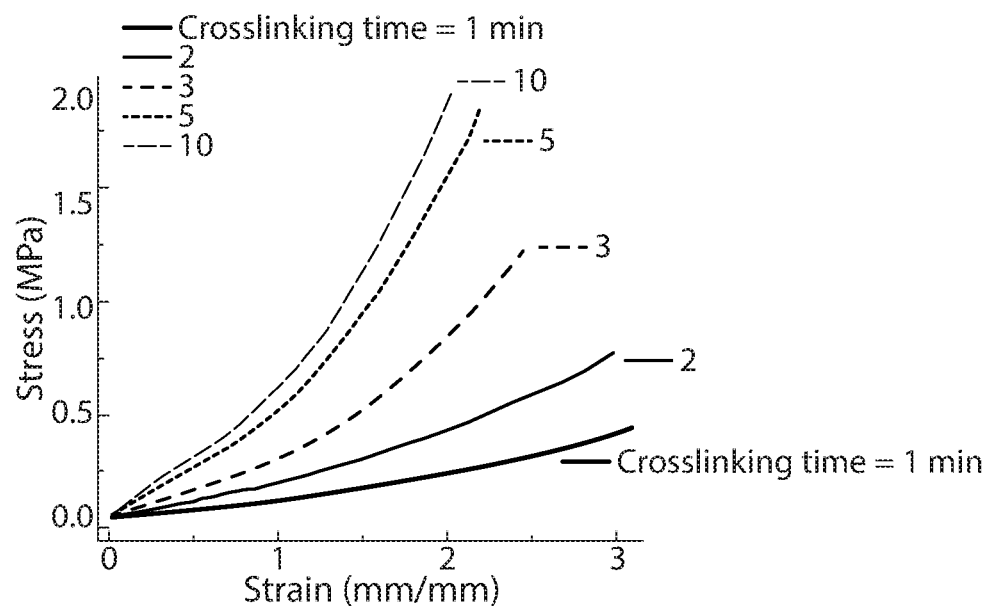
Figure 4C:
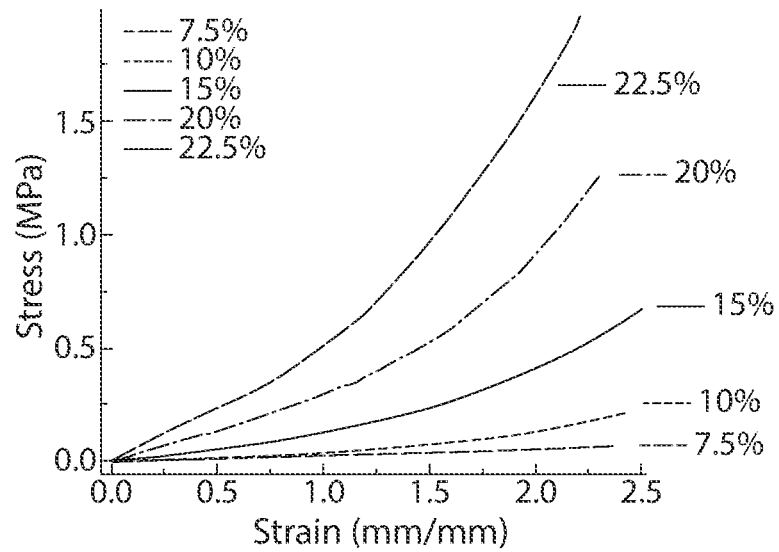
Figure 4D:
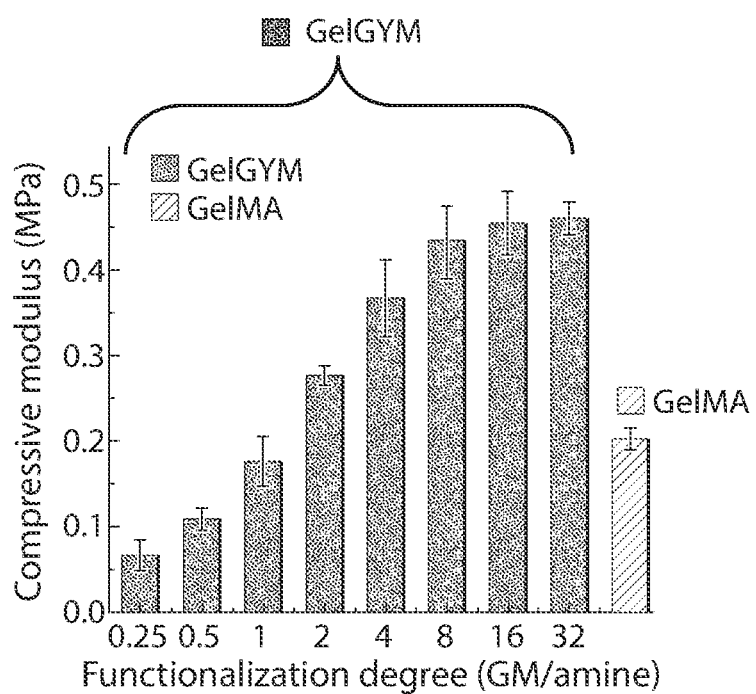
Figure 4E:
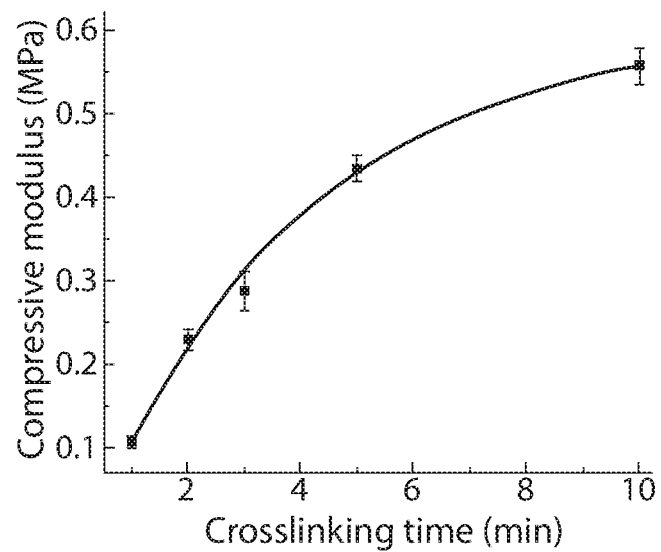
Figure 4F:
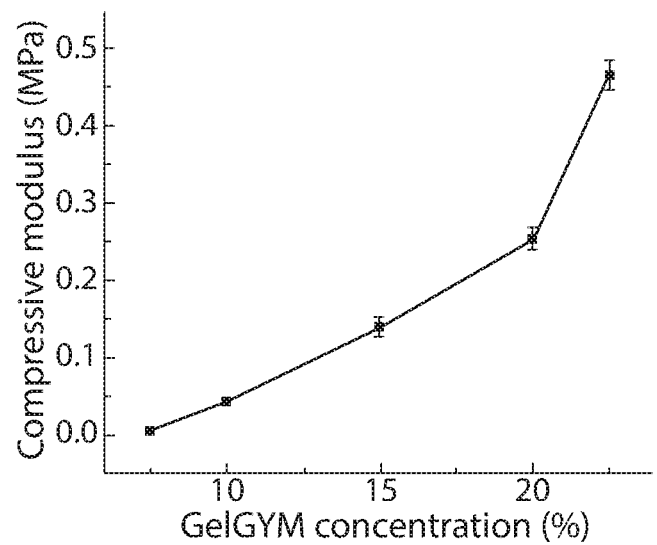
Figure 5A:
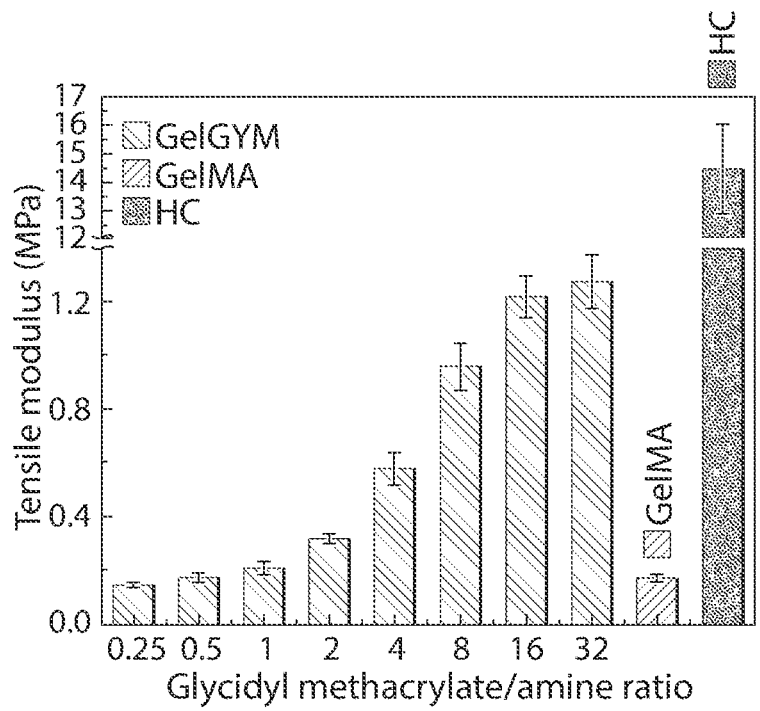
FIG. 5a-5d are bar graphs showing mechanical properties of GELGYM in comparison with GelMA and human cornea.
Figure 5B:
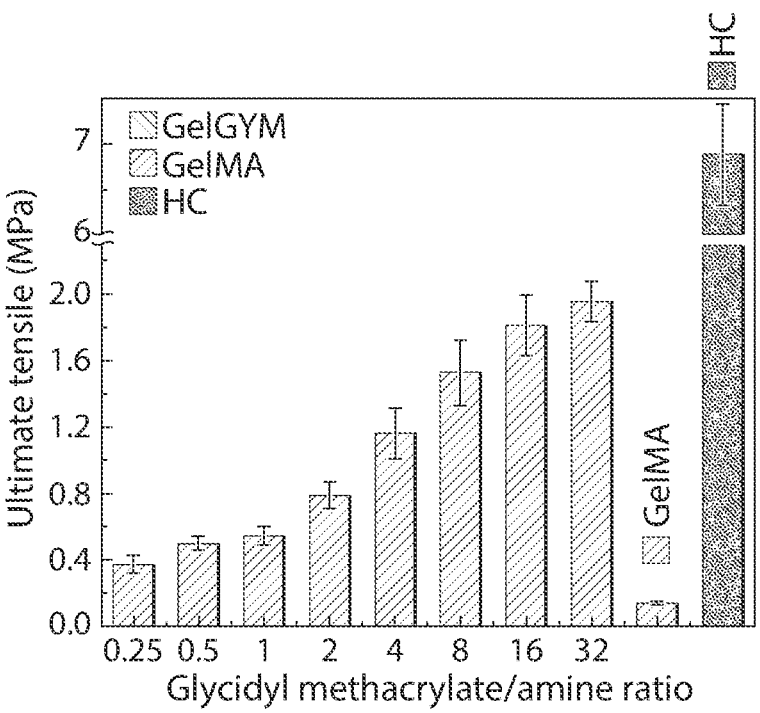
Figure 5C:
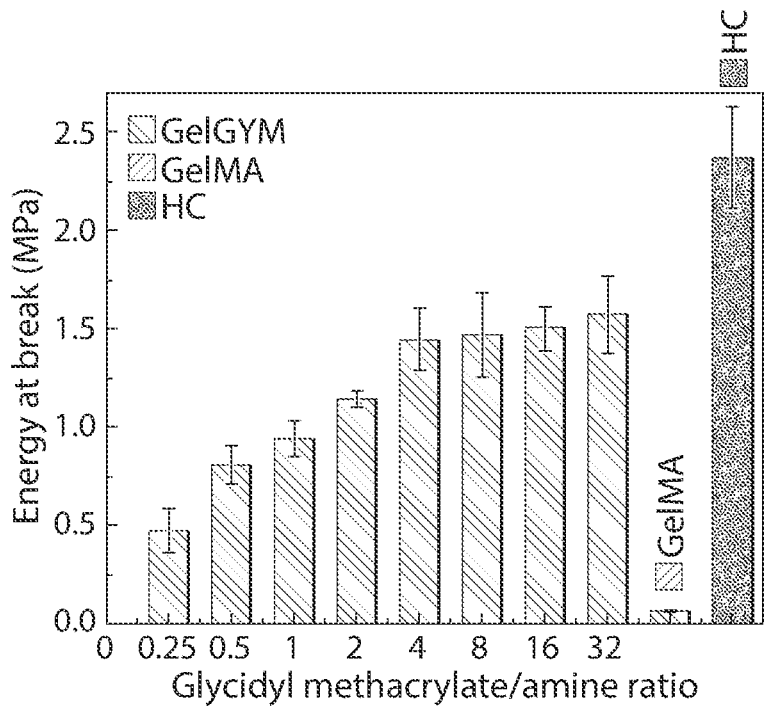
Figure 5D:
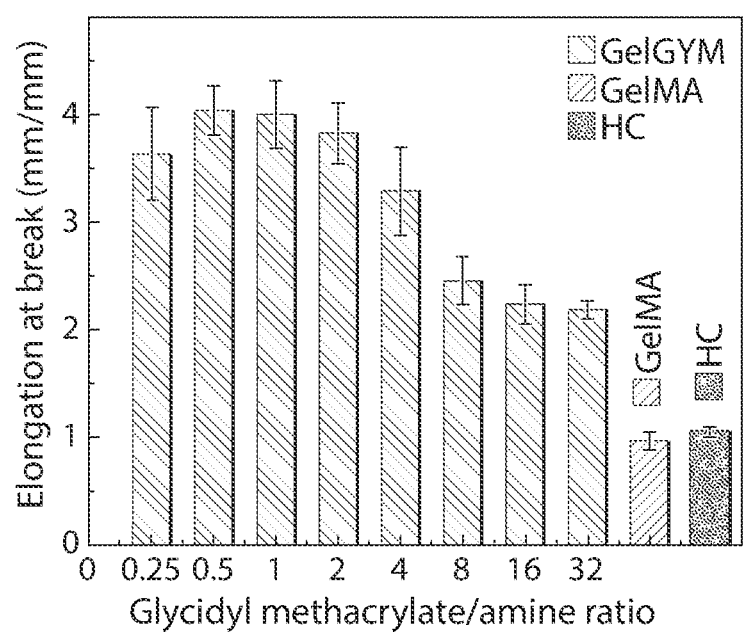
Figure 6A:
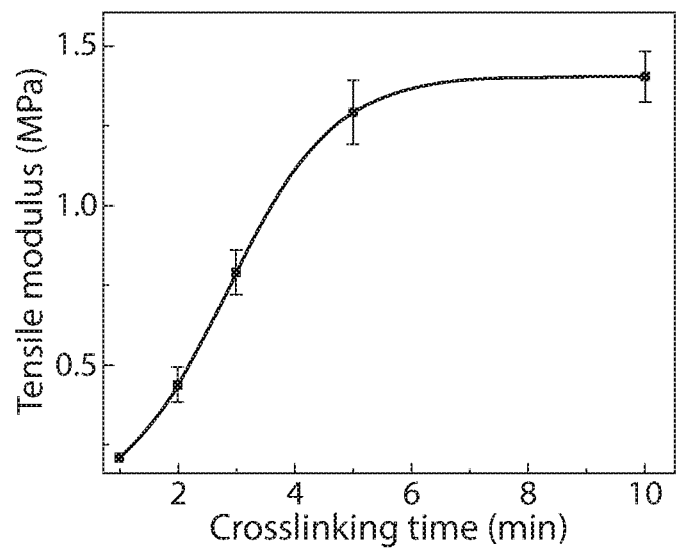
FIG. 6a-6d are line graphs showing mechanical properties of GELGYM.
Figure 6B:
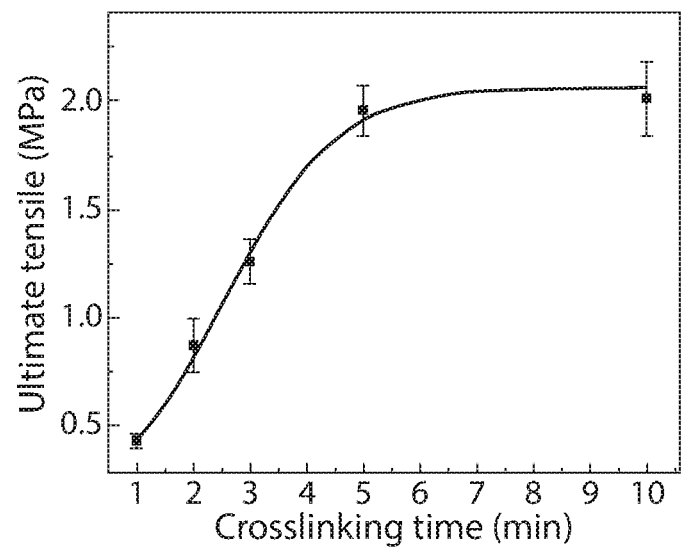
Figure 6C:
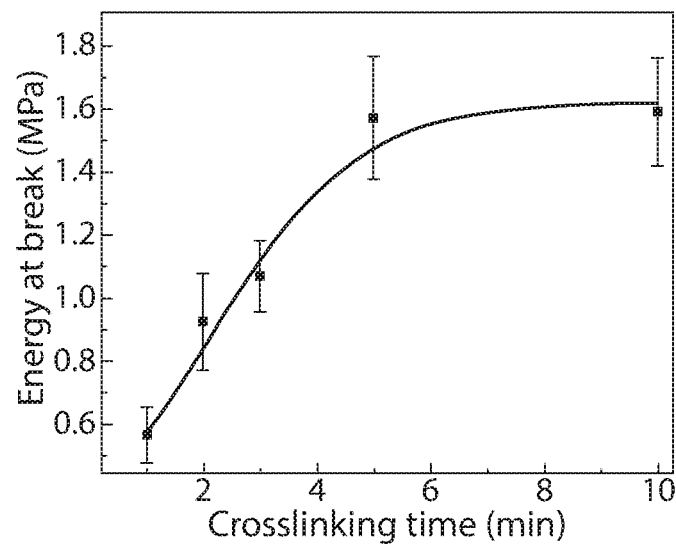
Figure 6D:
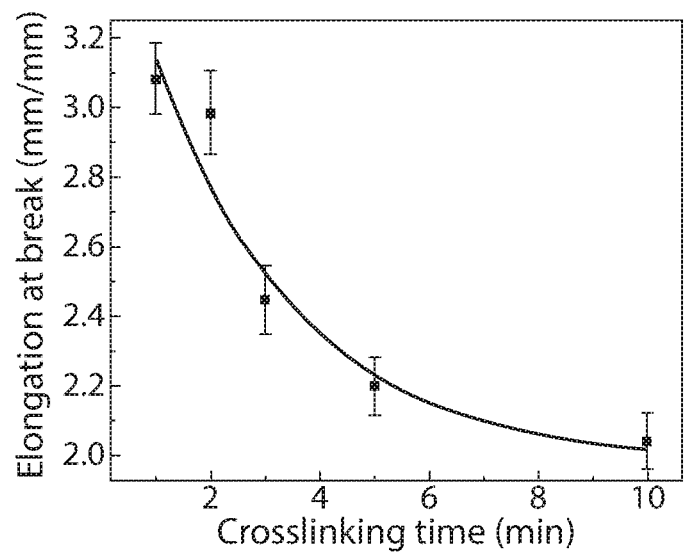
Figure 7A:
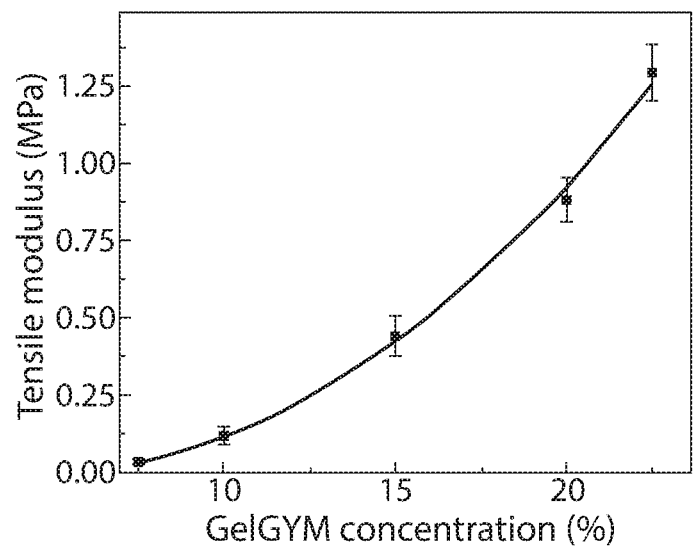
FIG. 7a-7d are line graphs showing mechanical properties of GELGYM.
Figure 7B:
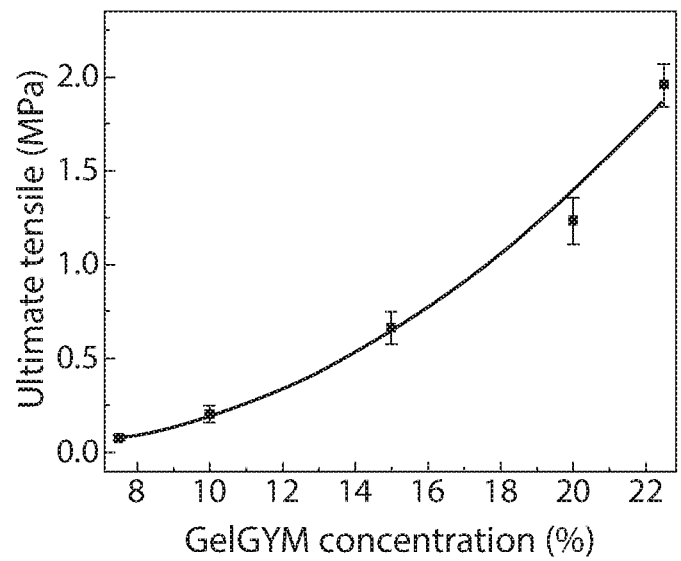
Figure 7C:
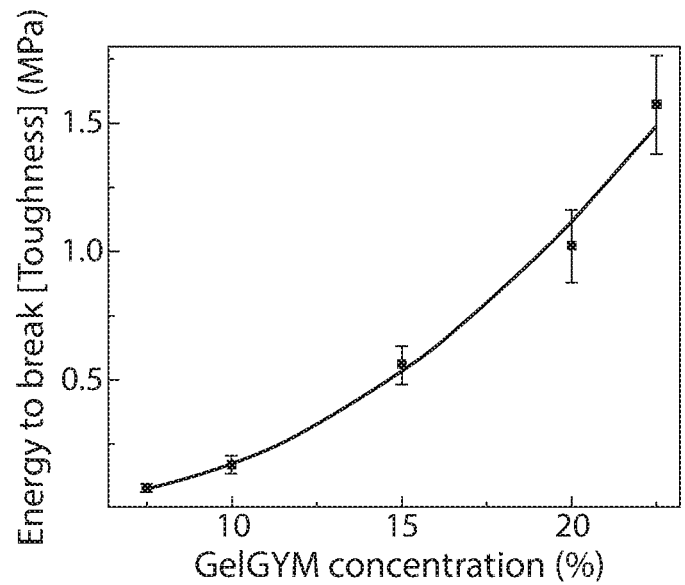
Figure 7D:
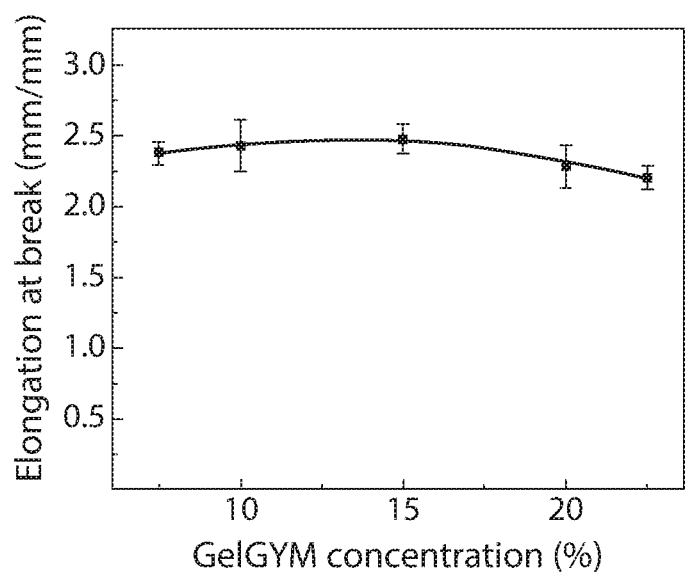
Figure 8A:
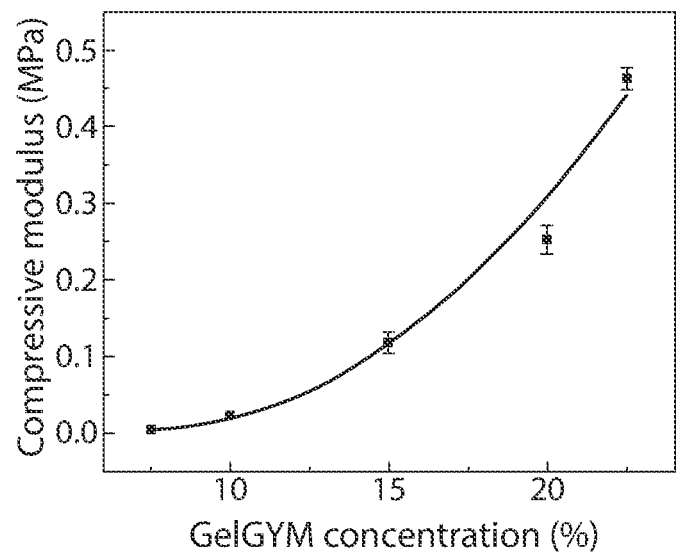
FIG. 8a-8b are line graphs showing mechanical properties of GELGYM.
Figure 8B:
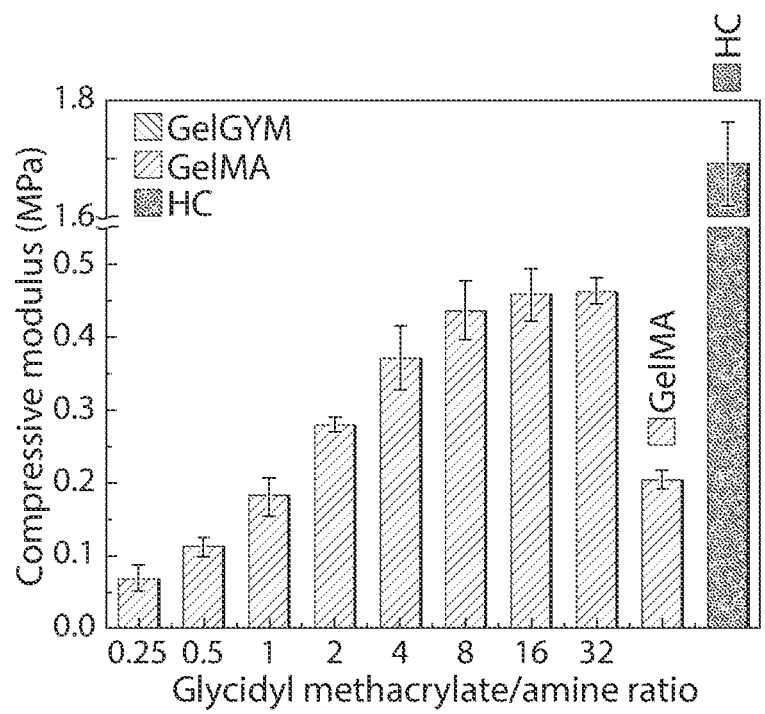
Figure 9A:
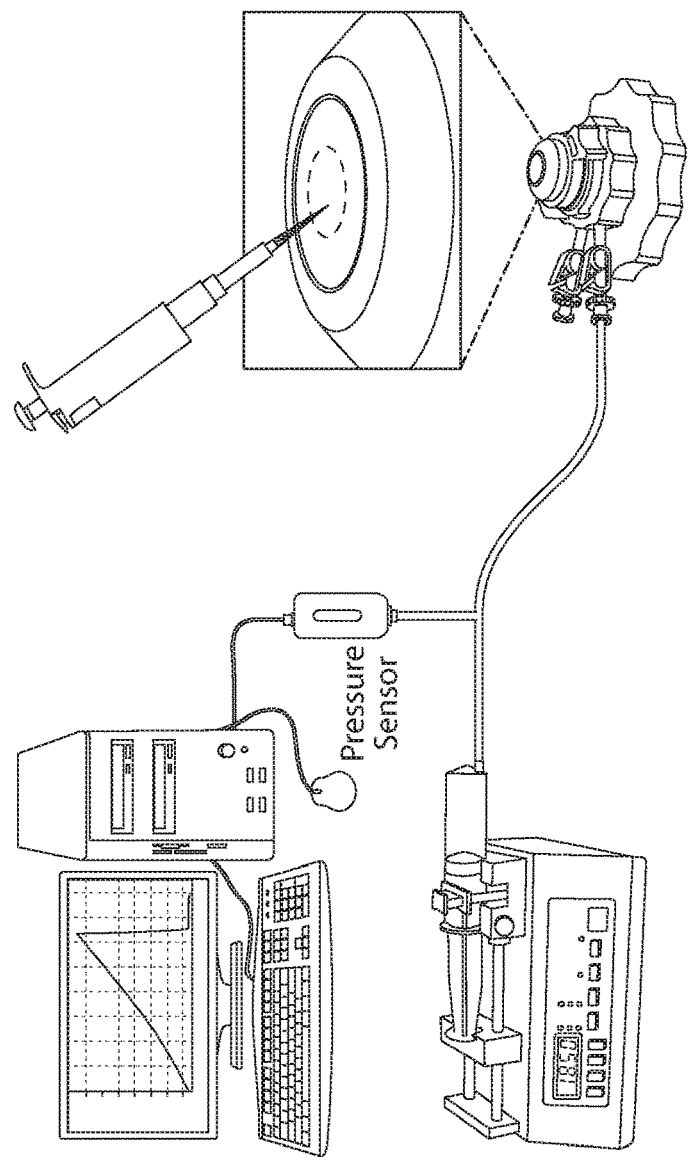
FIG. 9a-9b show adhesion properties of GELGYM.
Figure 9A:
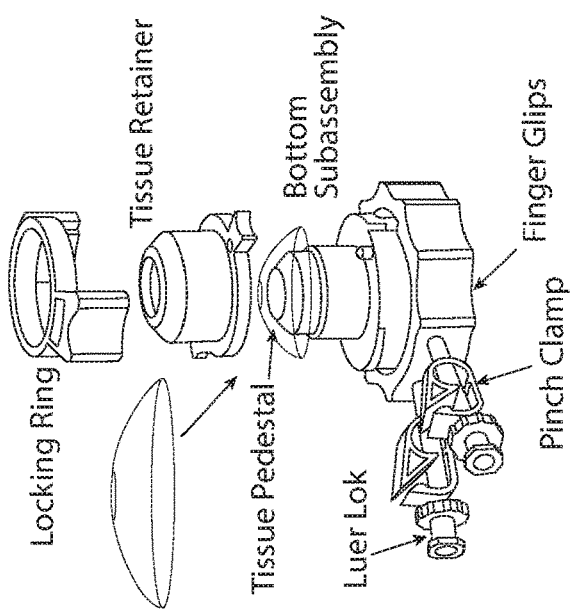
Figure 9B:
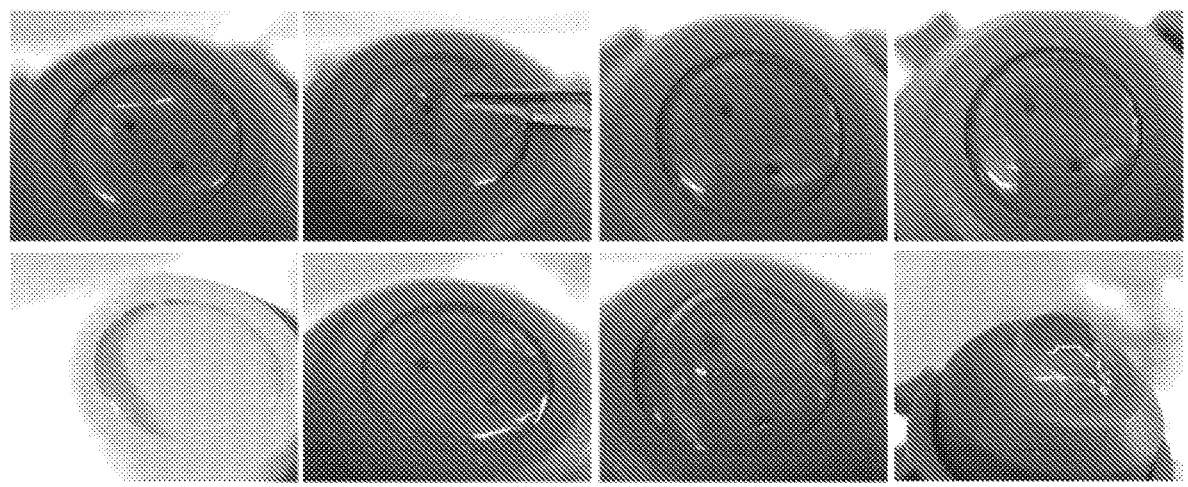

Material novelty: Glycidyl methacrylate-substituted gelatin (GELGYM) is novel, and has immense tuneability, which allows tailoring the properties of material to the medical needs. Gelatin functionalized with methacryloyl (GelMA) is the most studied derivative of gelatin for biomedical applications. However, scaffolds made of GelMA show poor mechanical properties due to low degree of functionalization (maximum 4%), which limits their biomedical application. To address this issue, we functionalized gelatin with glycidyl methacrylate, which allows us to controllably tune the functionalization degree in much wider range, since the product of first modification reaction also has the capability for further reaction. This leads to the extension of graft and installment of more functional moieties in a highly-controlled manner that enables mechanically robust scaffolds under lower energy and intensity of light, in the safe and acceptable range of light wavelength and intensity for ocular applications (FIG. 2). The current standards of care for repair of corneal stromal defects and thinning include tissue/patch grafting or glue application. Corneal transplantation and patch grafting require donor tissues, which may not be available. In addition, the use of allogeneic tissues for grafting carries a risk for immune reactions.

Tunable properties to optimize the biomechanical behavior of the scaffold: Unlike GelMA, which only holds 4% functional groups, the modification degree with glycidyl methacrylate and corresponding properties can be greatly tuned, unlocking multifunctional application of glycidyl methacrylate-substituted gelatin (FIGS. 4a-4f, FIGS. 12a-12b and FIGS. 13a-13b). The preliminary data has shown that the mechanical and adhesion properties of the hydrogel can be precisely controlled via tuning 1) functionalization degree, 2) light exposure time, and 3) prepolymer concentration, to afford biomaterials with varying tensile strength (0.1 to 2.3 MPa) and compressive modulus (0.05-0.5 MPa) that are comparable to the human native cornea (i.e. tensile strength of 6.88±0.58 MPa, and compressive modulus of 1.69±0.07 MPa) (FIGS. 4a-4f). However, GelMA hydrogels, in the similar settings, demonstrated tensile strength of 0.13±0.05 MPa and compressive modulus of 0.17±0.04 MPa. Such superb mechanical properties strongly suggest the application of glycidyl methacrylate-substituted gelatin as corneal adhesive to corneal substitute.

Figure 12A:
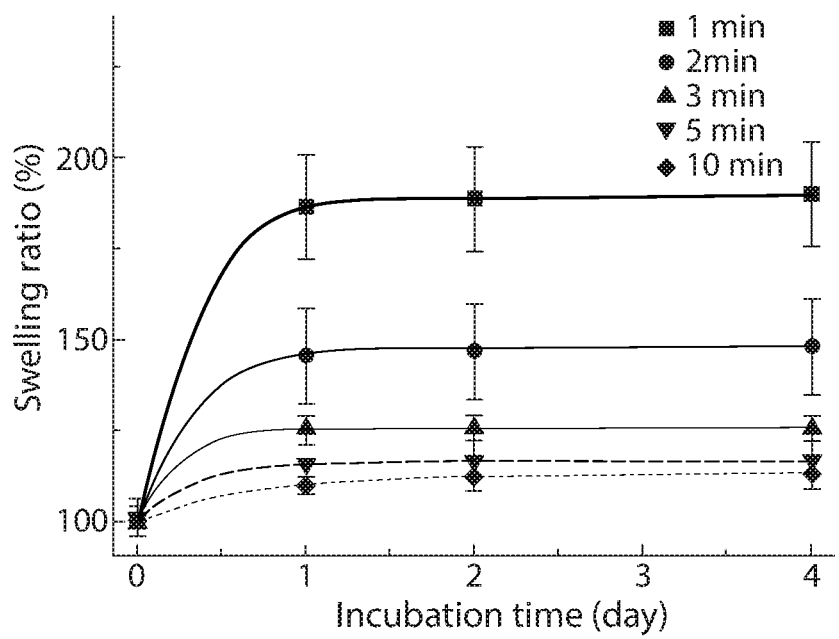
FIG. 12a-12b are line graphs showing physical and chemical properties of GELGYM.
Figure 12B:
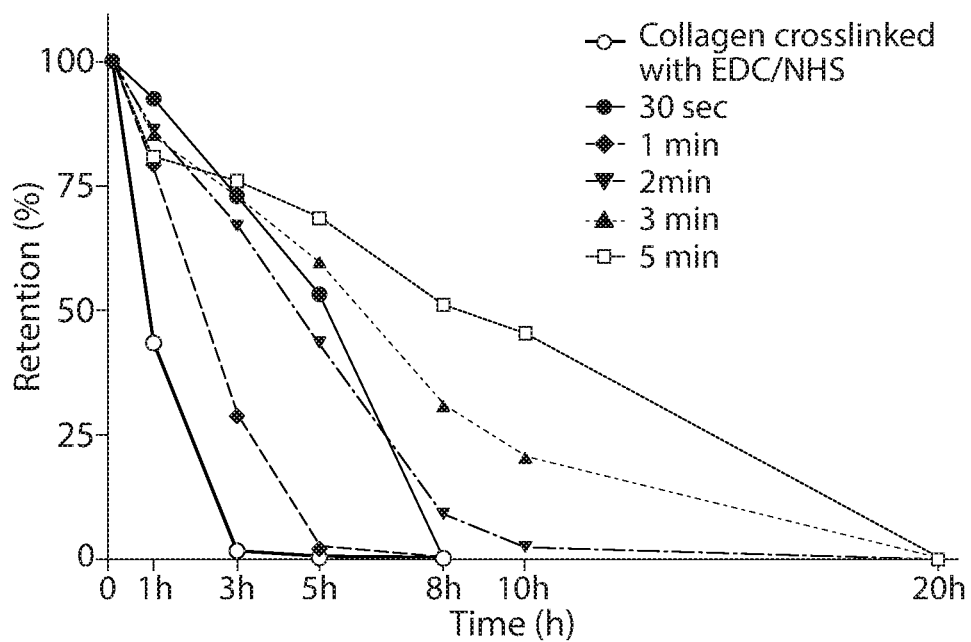

Furthermore, the data has revealed that the swelling ratio of glycidyl methacrylate-substituted gelatin can be easily tuned and controlled via varying crosslinking time, allowing to match those properties of the host tissue (FIG. 12a) which is in the range of 8-20%. In addition, we have shown that degradation time of glycidyl methacrylate-substituted gelatin in the presence of collagenase also can be programmed to match the healing time of the tissue (FIG. 12b). Moreover, the degradation time of the glycidyl methacrylate-substituted gelatin crosslinked under longer light exposure (i.e. 5 min or longer) is comparable to the porcine cornea degradation, which takes almost 26 h to fully degrade.

Figure 13A:
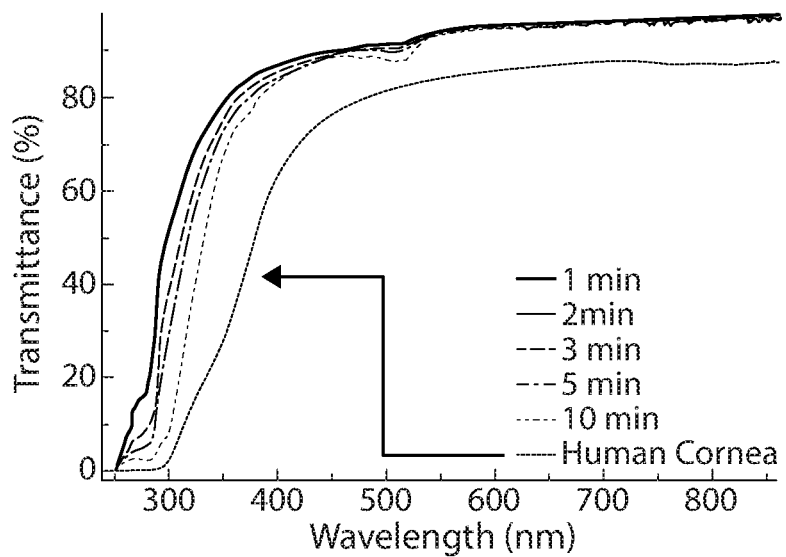
FIG. 13a-13b are line graphs showing optical properties of GELGYM and glucose permeability respectively.

Optimal optical properties: In vitro experiments demonstrate that glycidyl methacrylate-substituted gelatin has a similar optical behavior, in terms of transparency and UV absorption, to the human cornea (FIG. 13a).

Figure 13B:
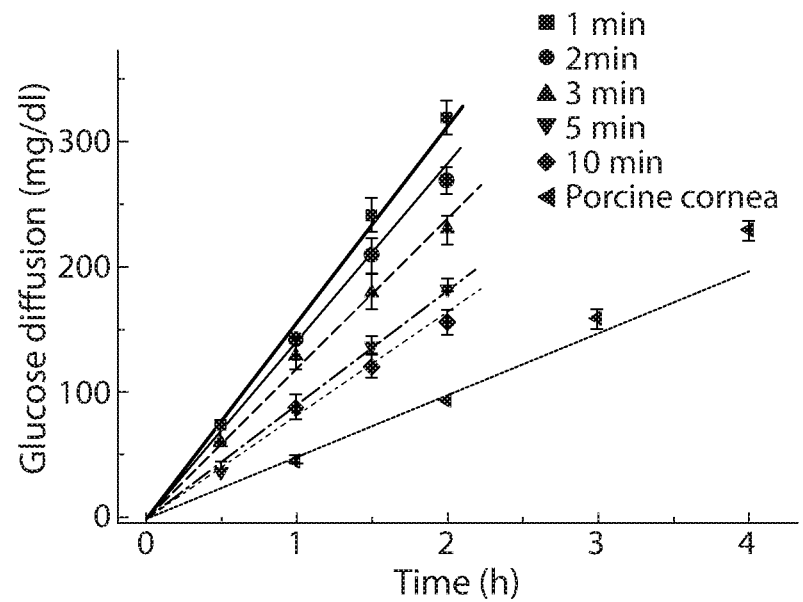
Figure 14A:
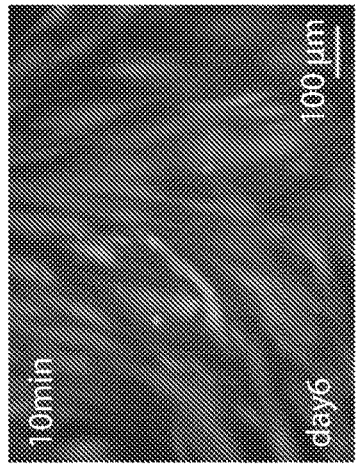
FIG. 14a-14e show in vitro biocompatibility of GELGYM in human corneal stroma cells.
Figure 14B:
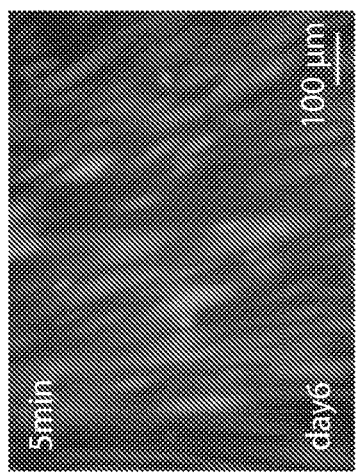
Figure 14C:
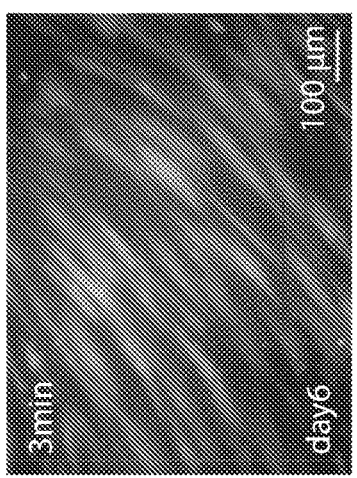
Figure 14D:
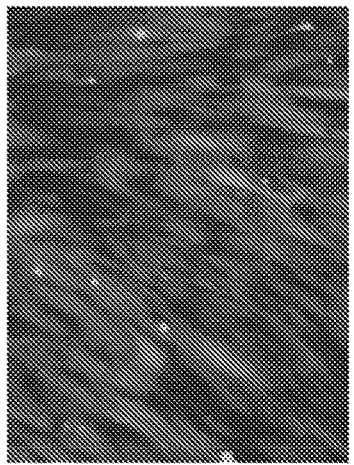
Figure 14E:
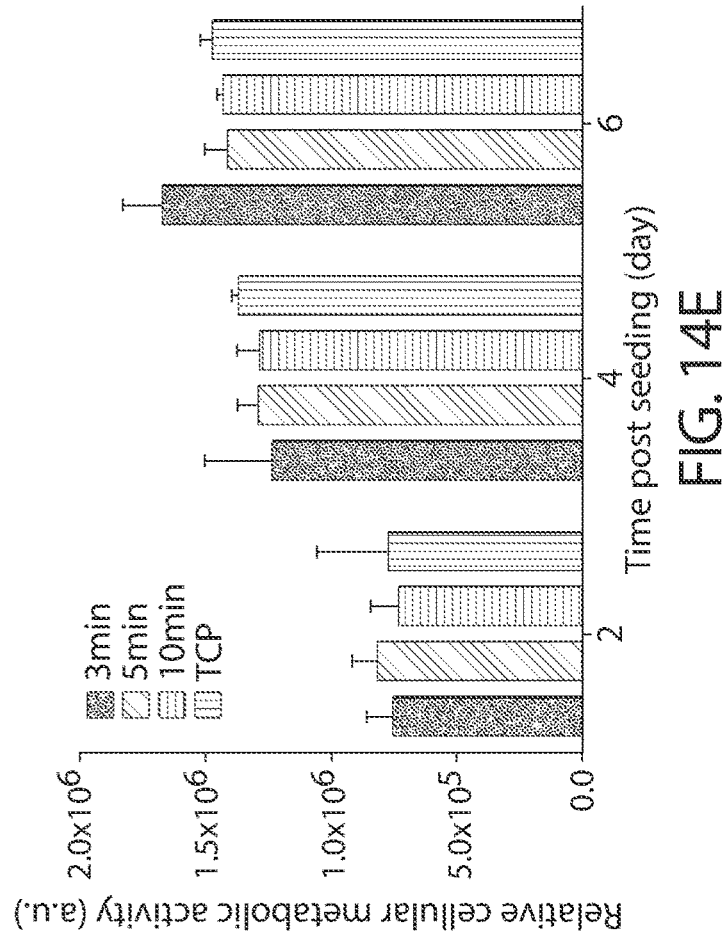
Figure 15A:
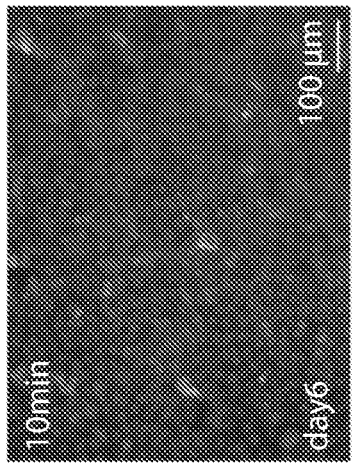
FIG. 15a-15e show in vitro biocompatibility of GELGYM in human corneal epithelial cells.
Figure 15B:
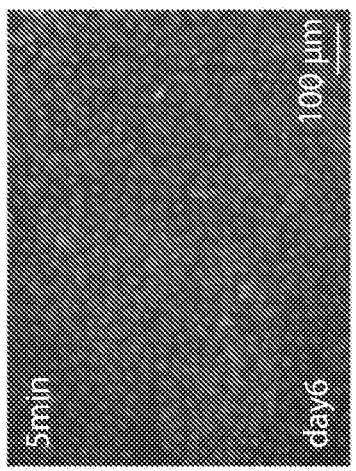
Figure 15C:
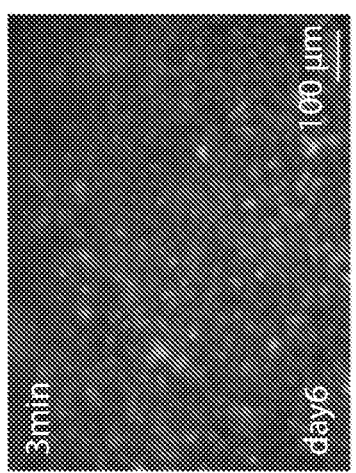
Figure 15D:
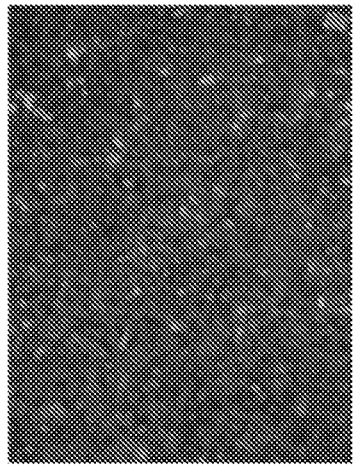
Figure 15E:
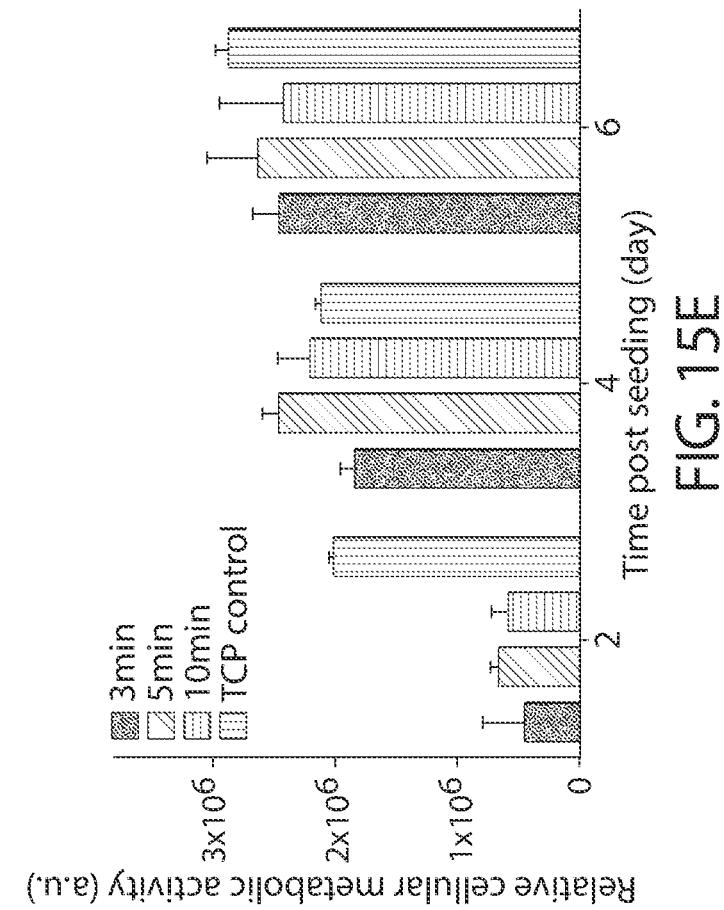
Figure 16A:
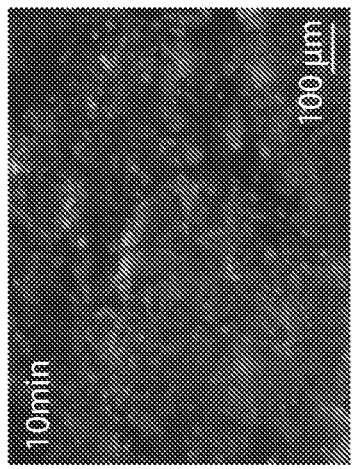
FIG. 16a-16e show in vitro biocompatibility of GELGYM in human neural progenitor cells.
Figure 16B:
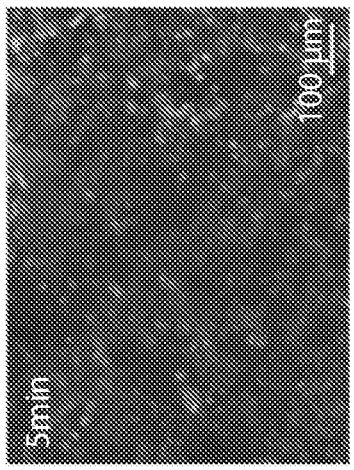
Figure 16C:
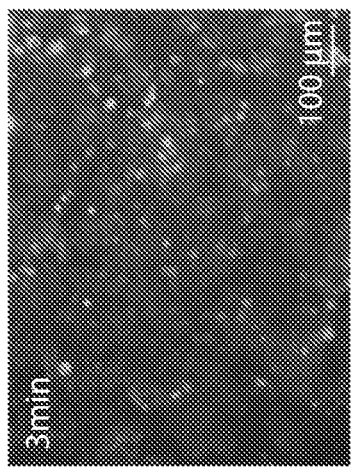
Figure 16D:
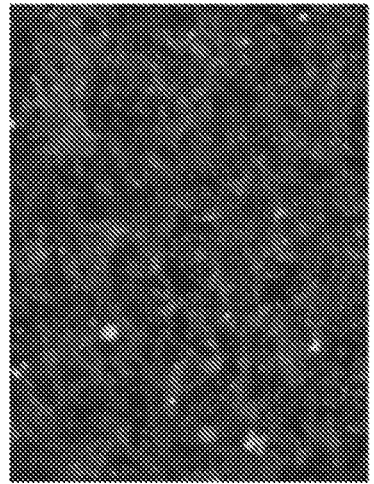
Figure 16E:
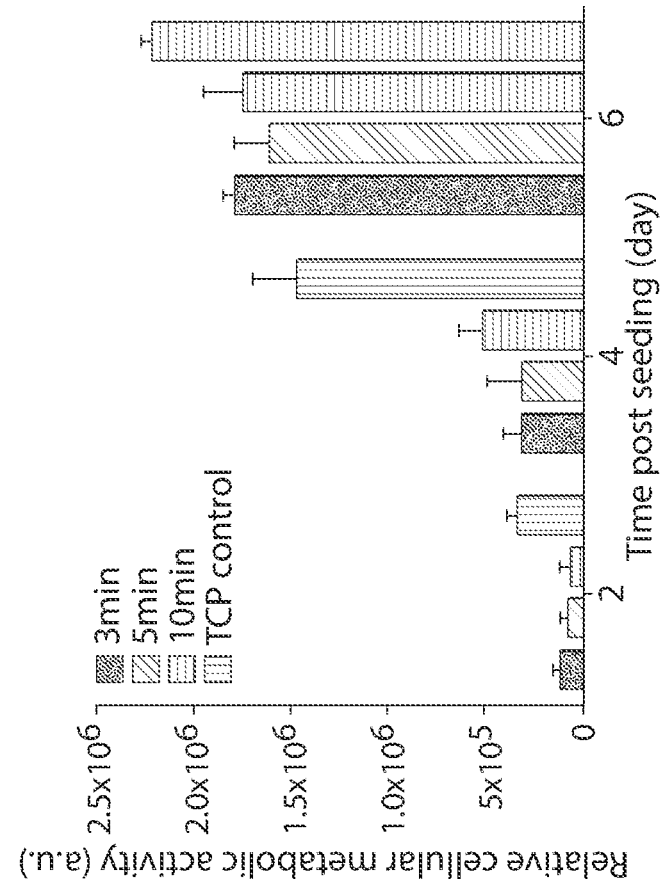
Figure 17:
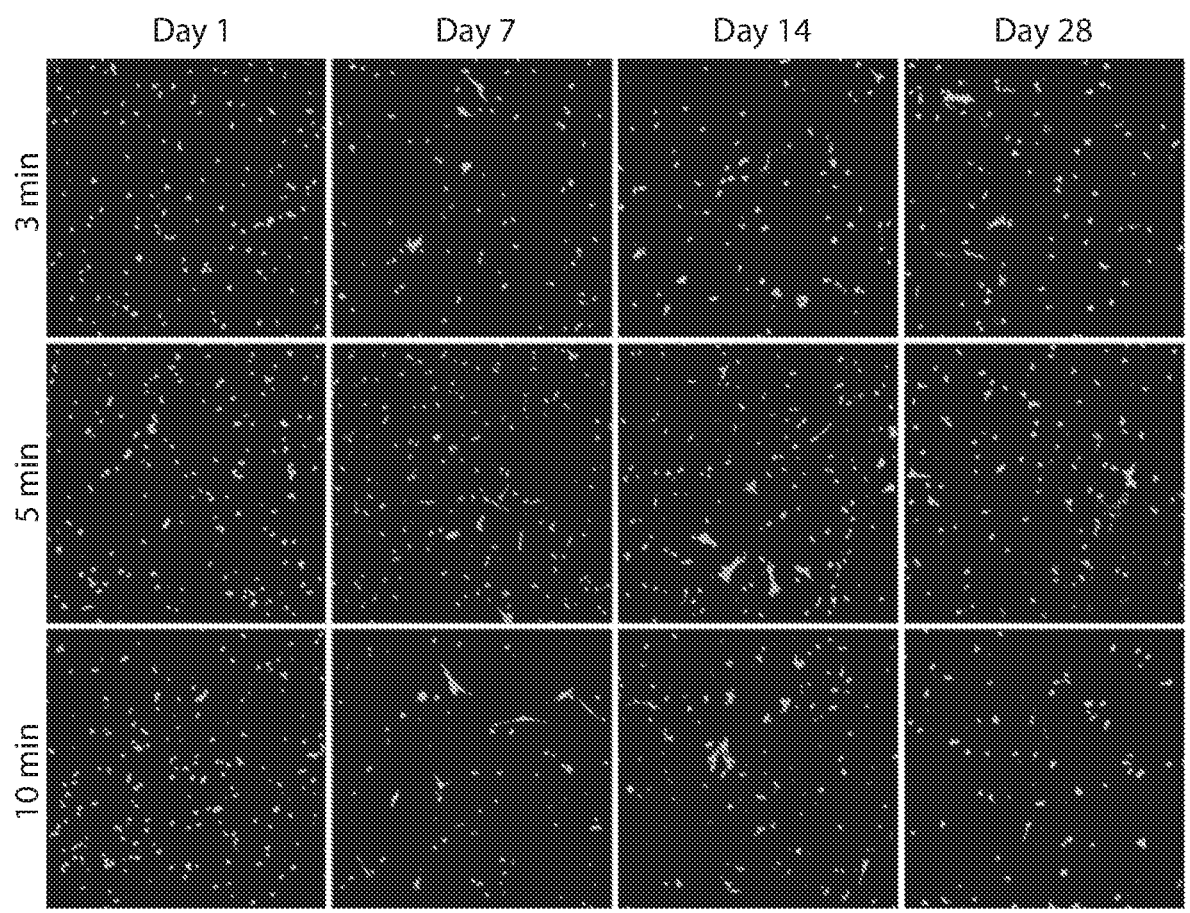
FIG. 17 are images showing biocompatibility of GEL-GYM in human corneal stroma cells in a 3D model. Human corneal stromal cells were cultured inside a prepolymer of GELGYM, and subsequently crosslinked, in order to evaluate the biocompatibility in a 3D model using a LiveDead assay. Moreover, the high cell viability observed even after 1 month in culture, suggests the feasibility of using GEL-GYM as a cell delivery system to be applied in cell therapy strategies.

High permeability to cell nutrients: In vitro data shows that glycidyl methacrylate-substituted gelatin has a higher glucose permeability compared to human cornea, allowing better diffusion of glucose and nutrients to the resident cells (FIG. 13b).

Optical biocompatibility: Most of the light-induced adhesives applied in biomedical applications use UV for cross-linking process, yet UV light is phototoxic and induces undesired DNA damage which limits its application for ophthalmology. Although, visible light crosslinking systems have well-established track records in a range of biomedical applications and have gained FDA approval for clinical use, the current light intensity and wavelength is too high for ocular use and may also lead to thermal and phototoxicity. To bypass such limitations, the inventors engineered a turquoise LED flash light (500-520 nm and 20 m W/cm$^2$ intensity) with its spectrum matching the maximum absorption of initiator (Eosin Y with $\lambda_{max}$ of 510 nm) to increase the efficacy of crosslinking reaction. Moreover, increasing the modification degree through grafting glycidyl methacrylate additionally allows to increase the efficiency of cross-linking and form hydrogels with superb mechanical and adhesion properties under low energy and intensity of light. Moreover, glycidyl methacrylate-substituted gelatin has superior biocompatibility since its base material is gelatin, derived from collagen, and unlike synthetic hydrogels which can release toxic fragments, its degradation leads to amino acid synthons that can be consumed by cells. Corneal epithelial cells and fibroblasts can migrate and proliferate over glycidyl methacrylate-substituted gelatin similar to the tissue culture plate, demonstrating high biocompatibility and biomimetic properties of the engineered scaffold (FIGS. 14a-14e and FIGS. 15a-15e).

Figure 11:
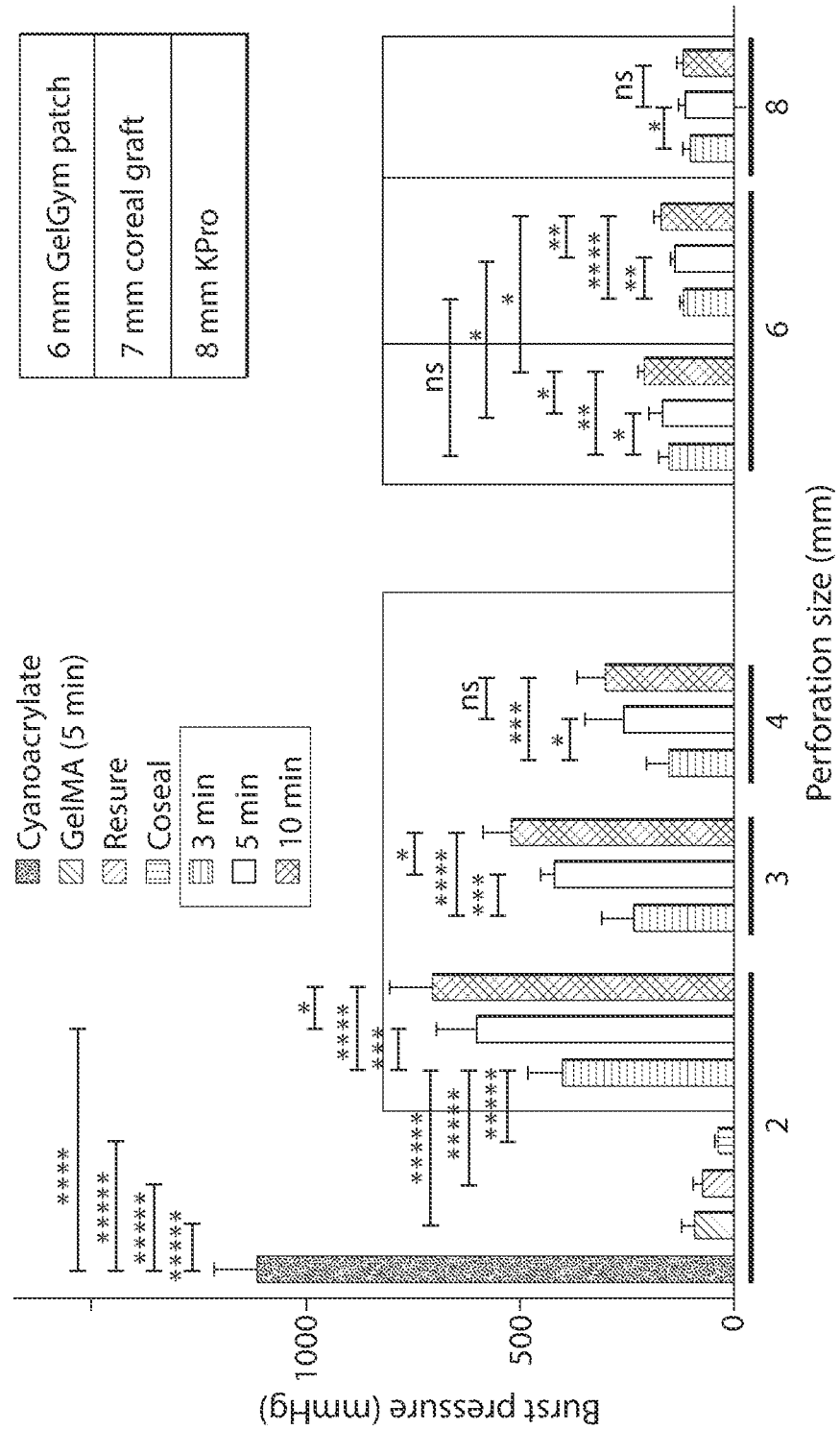
FIG. 11 is bar graph showing adhesion properties of GELGYM. The bar graph shows burst pressure evaluation of GELGYM in the liquid or implant form after application into perforated porcine corneas with different full-trephination diameters (2-6 mm) after 3, 5 and 10 min light exposure, compared to other tissue adhesives (cyanoacrylate, Resure, Coseal and GelMA after 5 min crosslinking). Liquid-phase of GELGYM can work as a sealant of corneal perforations with different diameters (perforation size). Moreover, polymerized GelGYM (solid-phase) can work as a substitute of the human cornea in keratoplasties and as Kpro carrier (GelGYM patch and KPro model, respectively, in the figure). Furthermore, liquid-phase GelGYM can glue not only perforations but also can be used to glue a GelGYM patch, a corneal graft or a KPro to the host cornea.

High adhesion and long retention (optimal biointegration): In vitro data has shown that glycidyl methacrylate-substituted gelatin has high adhesion to tissues even in wet conditions (according to burst pressure), and ex vivo adhesion tests (FIGS. 20a and 11), being able to repair even 4 mm-diameter penetrating corneal defects (FIG. 11). In addition, the preliminary data show that glycidyl methacrylate-substituted gelatin can adhere to human corneoscleral fragments and remain attached for more than 6 months under culture conditions, promoting proliferation and migration of corneal epithelial cells and fibroblasts into the glycidyl methacrylate-substituted gelatin (FIGS. 20a and 22a-22f). While biocompatible, glycidyl methacrylate-substituted gelatin has shown that its adhesion to the corneal tissue can by far exceed those of existing bioadhesives such as PEG-based sealants (ReSure and CoSeal) and GelMA (FIG. 11).

Example 2: Corneal Tissue Regeneration

Figure 22C:
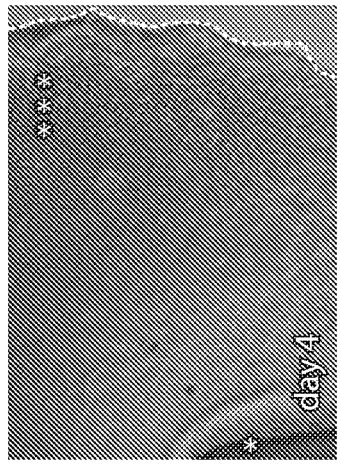
FIG. 22a-22f are images showing cell-GELGYM interaction.
Figure 22F:
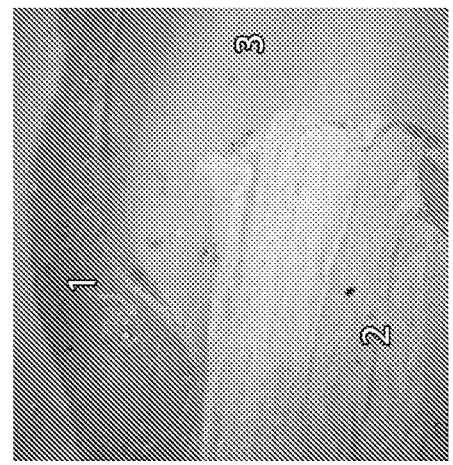
Figure 22B:
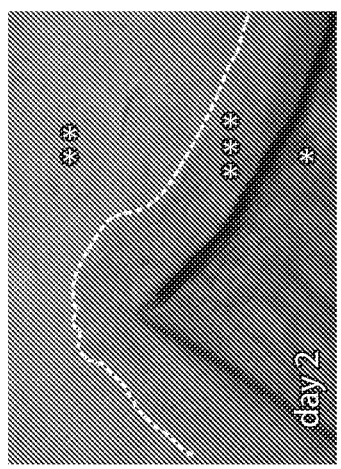
Figure 22E:
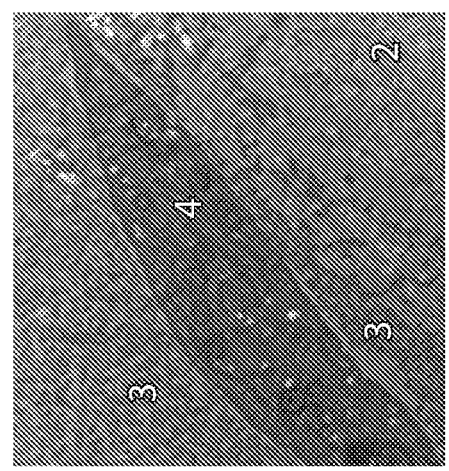
Figure 22A:
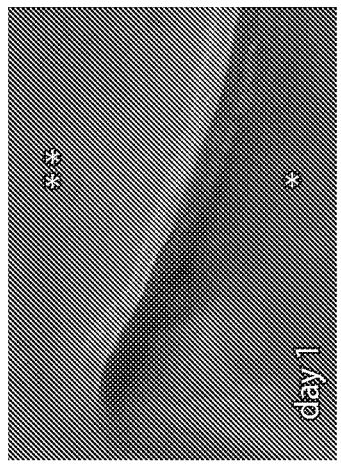
Figure 22D:
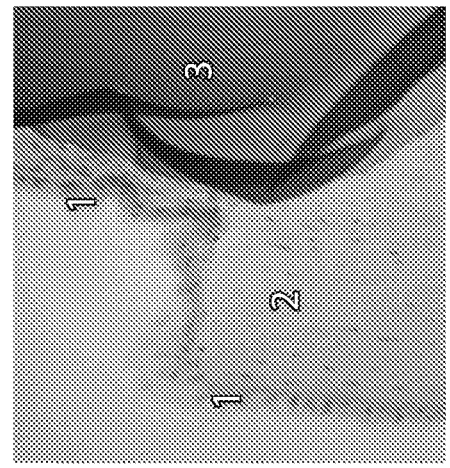

Unlike synthetic and many natural based scaffolds, glycidyl methacrylate-substituted gelatin allows both tissue sealing and regeneration, since cell binding sites such as Arg-Gly-Asp, and MMP-sensitive motifs retained intact. This permits cells to proliferate and migrate inside the hydrogel (FIG. 22a-22f), accelerating cornea tissue healing. The inventors note that this is the first engineered bioadhesive that can possibly meet all of the above criteria. The data demonstrates that epithelial cells of limbal tissue can migrate and proliferate to cover the 5 mm piece of glycidyl methacrylate-substituted gelatin in less than a week (FIG. 22a-22d). Fibroblasts also have been shown to penetrate inside of the scaffold within a month (FIG. 22e-22f).

Figure 10:
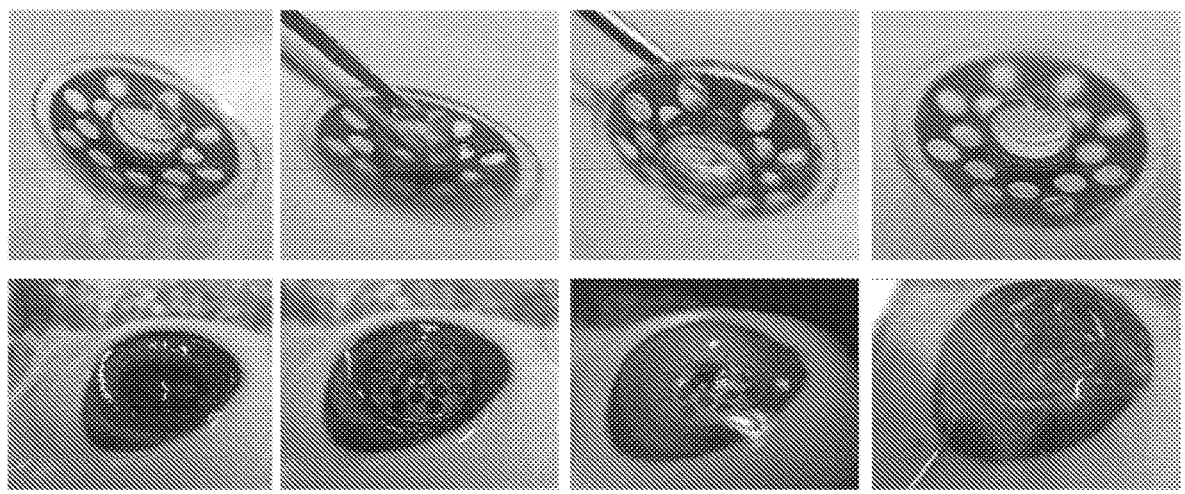
FIG. 10 are images showing application of pre-crosslinked polymerized GELGYM as scaffold to act as KPro carrier. GELGYM has been also used as a bioadhesive to glue the polymerized GelGYM-based KPro carrier to the host trephined cornea in a porcine ex vivo model.

Ease of fabrication and handling: Glycidyl methacrylate-substituted gelatin can be easily molded into desired sizes and shapes, and subsequently cured by visible light. Additionally, as an adhesive, there is a sufficient control to allow the surgeon to re-apply the adhesive if needed (FIG. 10).

In vitro and ex vivo data suggests that glycidyl methacrylate-substituted gelatin, with its higher degree of functionalization (32:1), at the concentration of 22.5% w/w, and when exposed to engineered visible light for a longer period of time (≥5 min) embues the glycidyl methacrylate-substituted gelatin scaffold with mechanical and optical properties comparable to those of human cornea. The data also demonstrate that the crosslinking reaction reaches near completion after 5 min light exposure, and longer radiation only minimally enhances the mechanical properties.

Example 3: Synthesis, Mechanical Properties and Applications of GELGYM

Figure 25A:
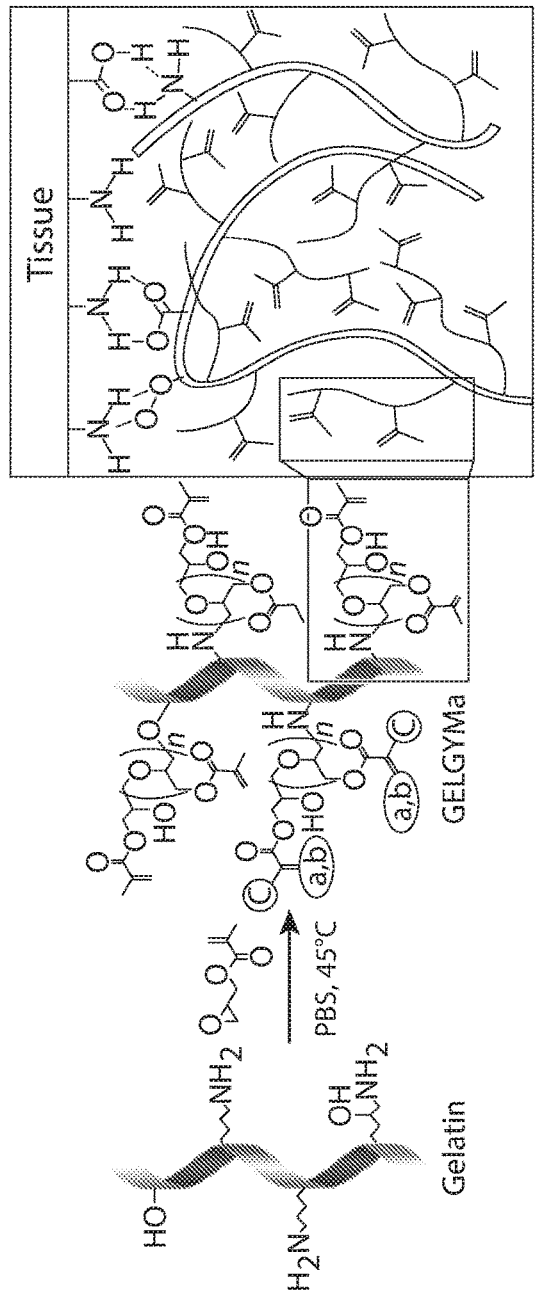
FIG. 25a-25e show synthesis, crosslinking and chemical characterization of GELGYM.
Figure 25B:
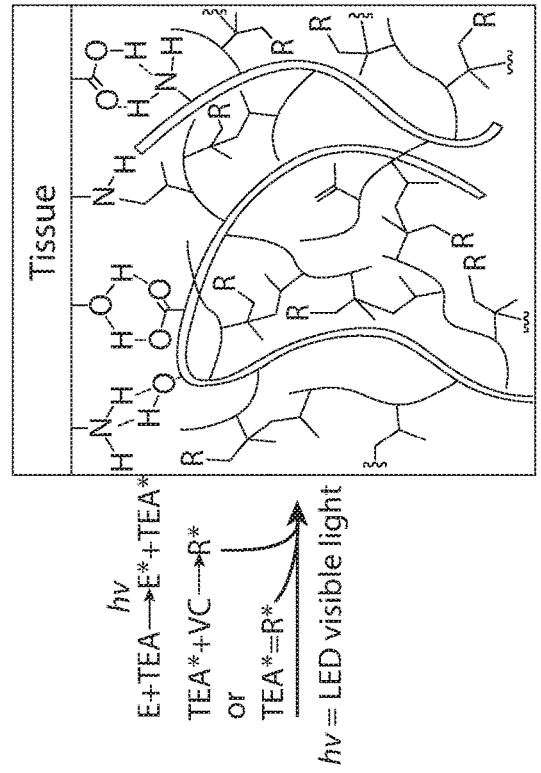
Figure 25C:
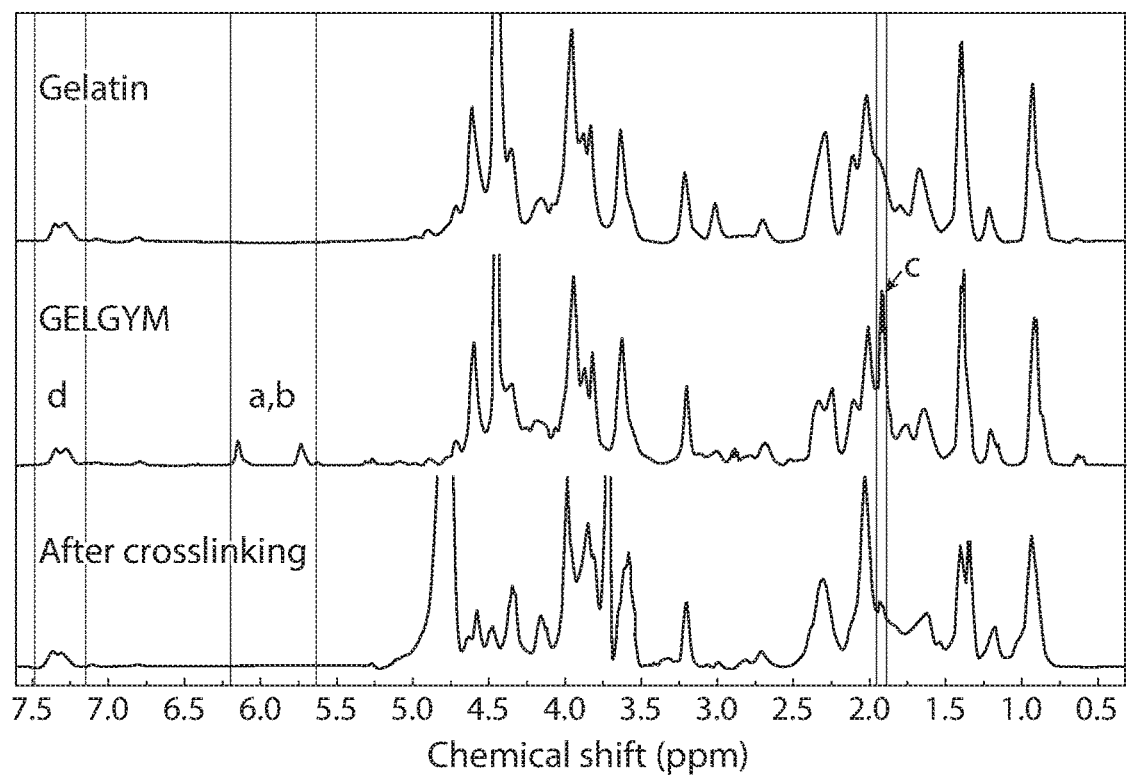
Figure 25D:
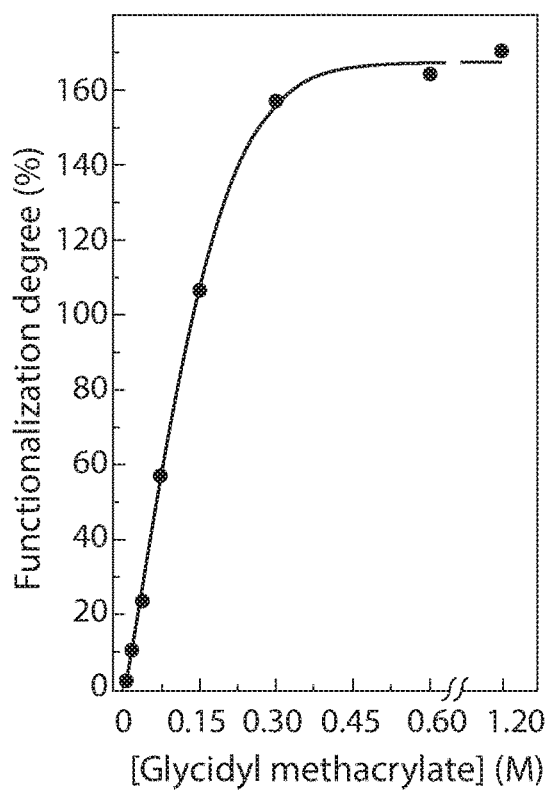
Figure 25E:
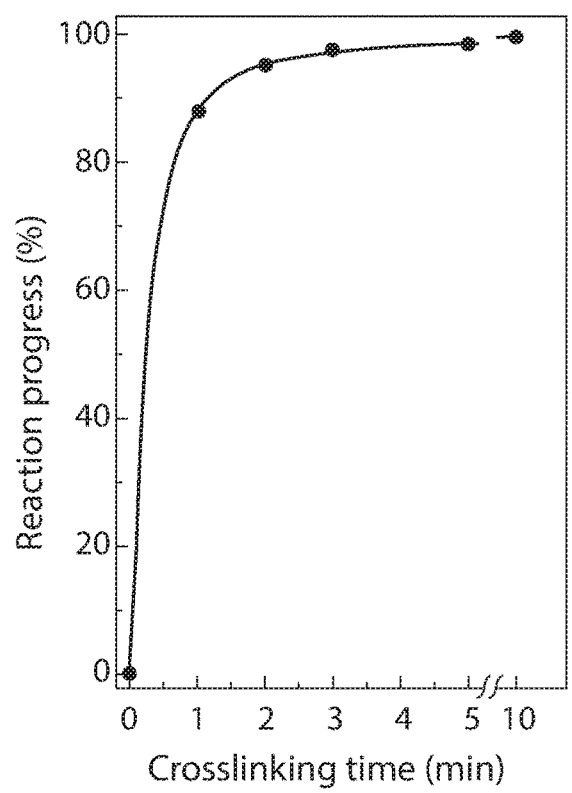

It was postulated that the addition of more crosslinkable functional moieties on the gelatin backbone could enable us to bypass such limitations and modulate the functionalization and subsequent crosslinking degree in a greater range. In order to achieve this, we utilized graft polymerization approach, and grafted the nucleophile groups of gelatin with glycidyl methacrylate via epoxide ring opening reaction (FIG. 25a). Varying the concentration of glycidyl methacrylate in the reaction has enabled us to readily tune the functionalization degree (FD) between 2.6% to 171% (in average per each amine moieties, from 0.026 to 1.71 glycidyl mathacrylates groups are attached to the backbone). The FD of engineered precursor (herein called GELGYM) was calculated using proton nuclear magnetic resonance ($^1$H-NMR) spectroscopy, through comparison of a+b integrals, corresponded to olefinic hydrogens of methacrylate (5.73 and 6.15 ppm) with the aromatic hydrogens present in the phenylalanine, tyrosine and histidine (indicated by d in 7.3-7.5 ppm) (FIGS. 25c-25d). The Fourier-transform infrared (FT-IR) spectroscopy of the GELGYM precursor further demonstrated the formation of GELGYM with different FD. The appearance of the carbonyl absorption peak of methacrylate ester moieties as manifested by a gradual increase in the intensity of absorption peak at 1650 cm$^{-1}$ along with a spectral blue shift at 1650 and 1533 cm$^{-1}$ in FT-IR spectra further validated the formation of GELGYM with different FD. The engineered GELGYM has shown to be crosslinked upon exposure of visible light (505-515 nm) with an intensity as low as (i.e. 20 mW/Cm$^2$) in the presence of eosin Y (E) triethanolamin (TEA) and vinyl caprolactam (VC) through radical reaction and form a robust hydrogel that can strongly adhere to different biological tissue surfaces (FIG. 25b). Gradual decline in the integral of a+b peaks in the H-NMR spectra of GELGYM compared to aromatic hydrogens (d) as a function of reaction time was utilized to quantify the reaction progress (FIG. 25c). Our analysis demonstrated a sigmoidal correlation between the crosslinking reaction progress and radiation time; and the reaction reaches to nearly completion in 10 min (FIG. 25e).

Figure 26A:
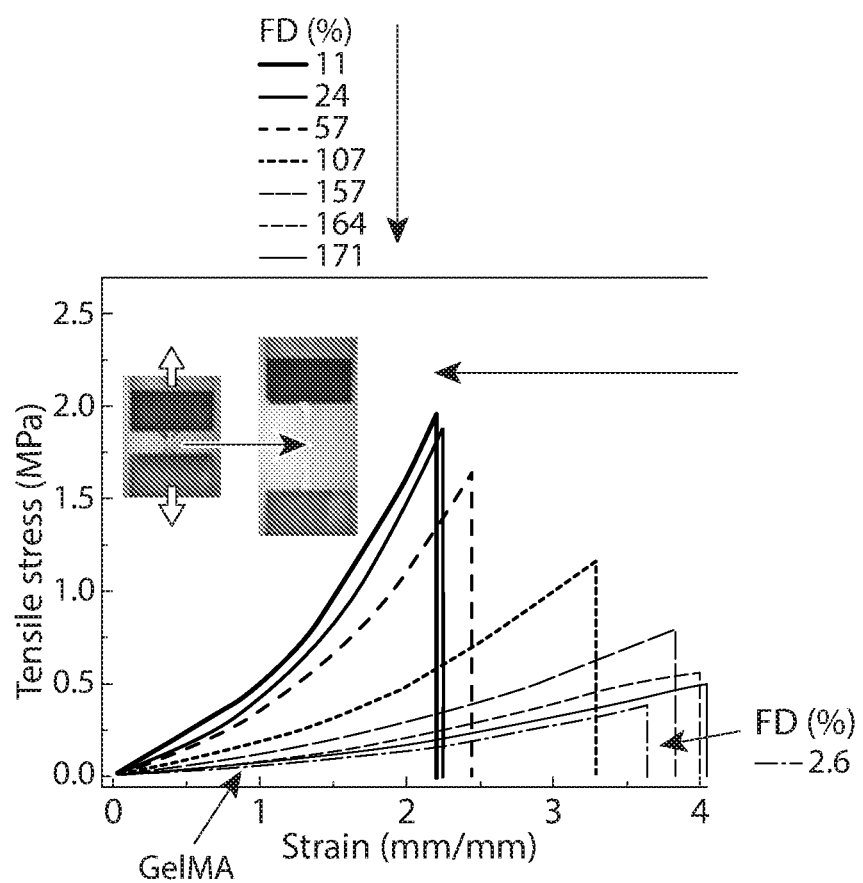
FIG. 26a-26p show mechanical characterization of GEL-GYM, crosslinked with a visible LED in the presence of Eosin Y (0.05 mM), TEA 0.04% and vinyl caprolactam (0.04%).
Figure 26B:
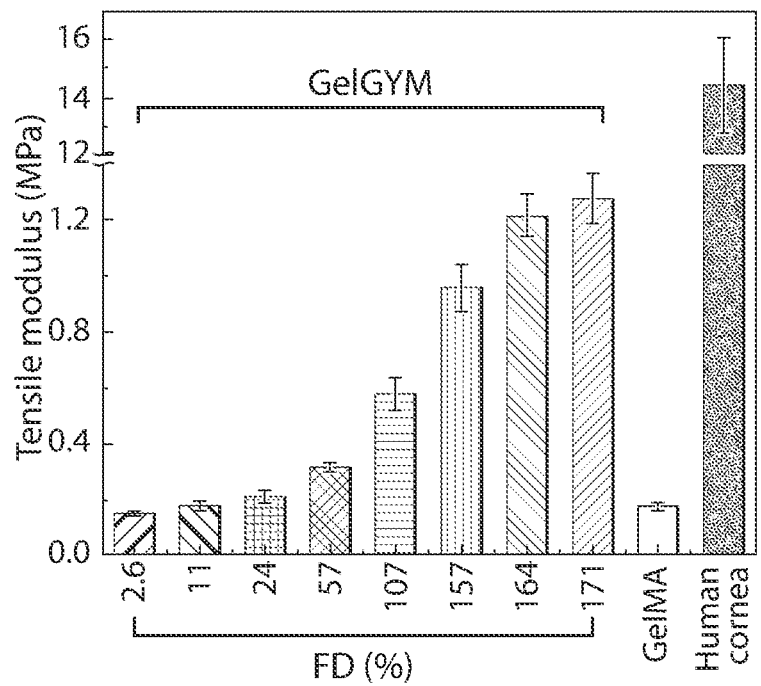
FIG. 26b is bar graph showing tensile modulus compared to those of GelMA and fresh human cornea.
Figure 26C:
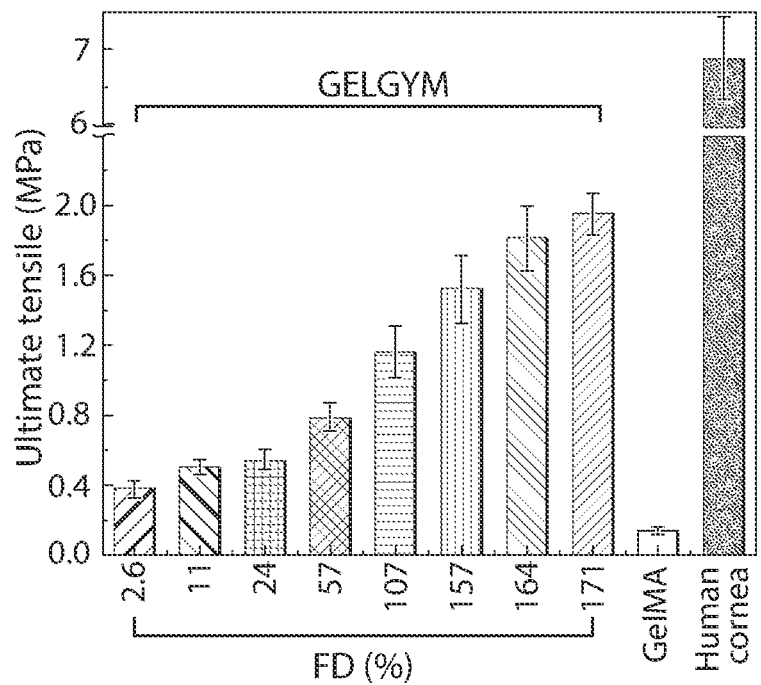
FIG. 26c is bar graph showing ultimate tensile compared to those of GelMA and fresh human cornea.
Figure 26D:
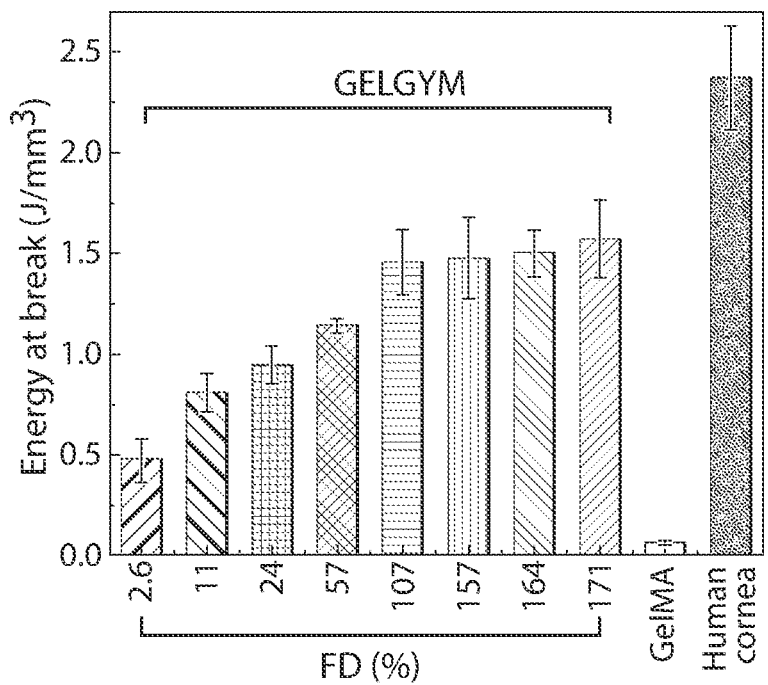
FIG. 26d is bar graph showing energy at breaks compared to those of GelMA and fresh human cornea.
Figure 26E:
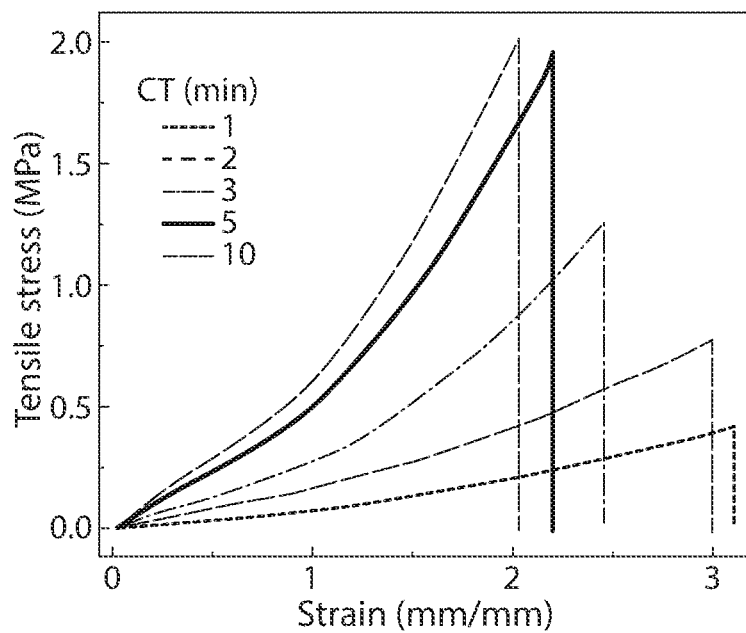
FIG. 26e shows representative tensile stress/strain curve of GELGYM hydrogels (FD of 171% and 22.5% w/v) with varying crosslinking time (CT) and their corresponding mean tensile modulus (FIG. 26f), ultimate tensile (FIG. 26g) and energy at breaks (FIG. 26h), compared to those of GelMA and fresh human cornea.
Figure 26F:
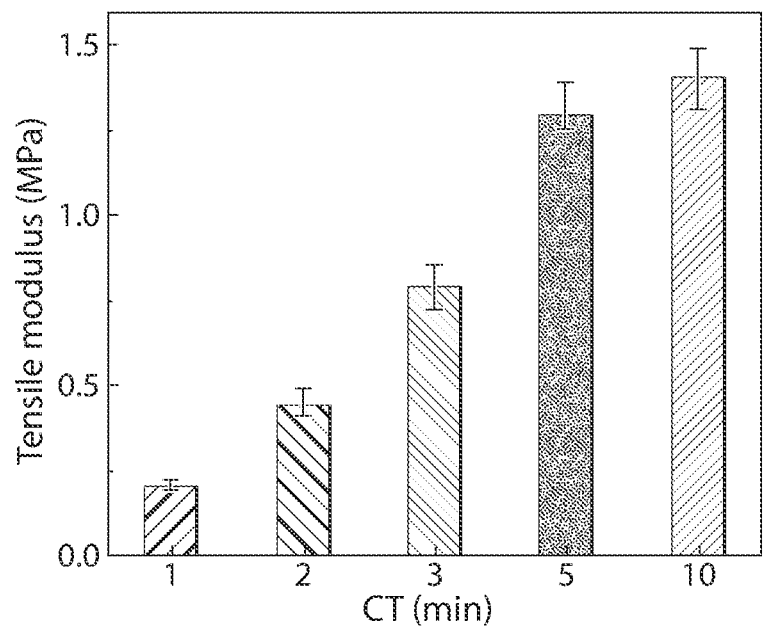
FIG. 26i shows representative tensile stress/strain curve of GELGYM hydrogel (FD of 171% and crosslinked for 5 min) with varying concentration and their corresponding tensile modulus (FIG. 26j), ultimate tensile (FIG. 26k) and energy at breaks (FIG. 26l), compared to GelMA and fresh human cornea.
FIG. 26m shows representative compressive stress/strain curves for GELGYM (22.5% w/v and crosslinked for 5 min) with varying functionalization degree (FD). The mean compressive modulus of GELGYM with varying FD (FIG. 26n), CT (FIG. 26o) and concentration (FIG. 26p), compared to those of GelMA and fresh human cornea. (The inset of (FIG. 26m) demonstrates the unique compressibility of the GEL-GYM).
Figure 26G:
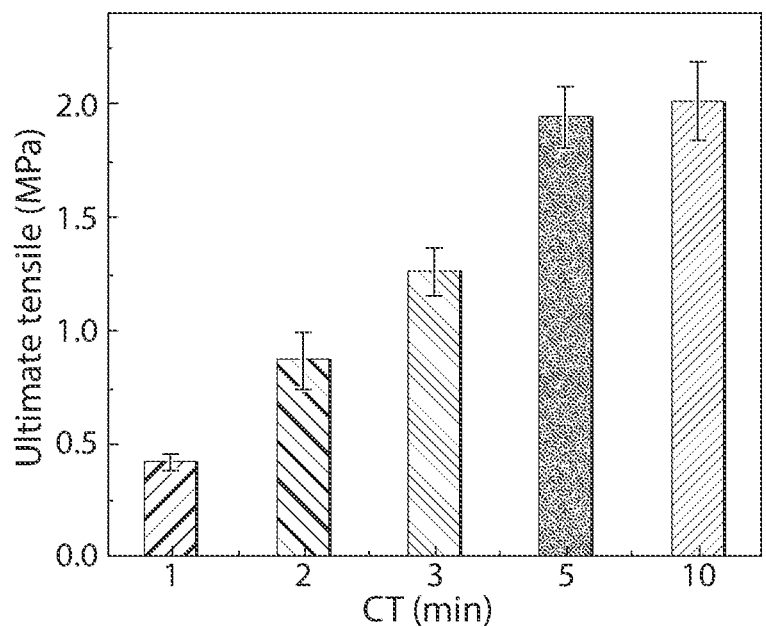
Figure 26H:
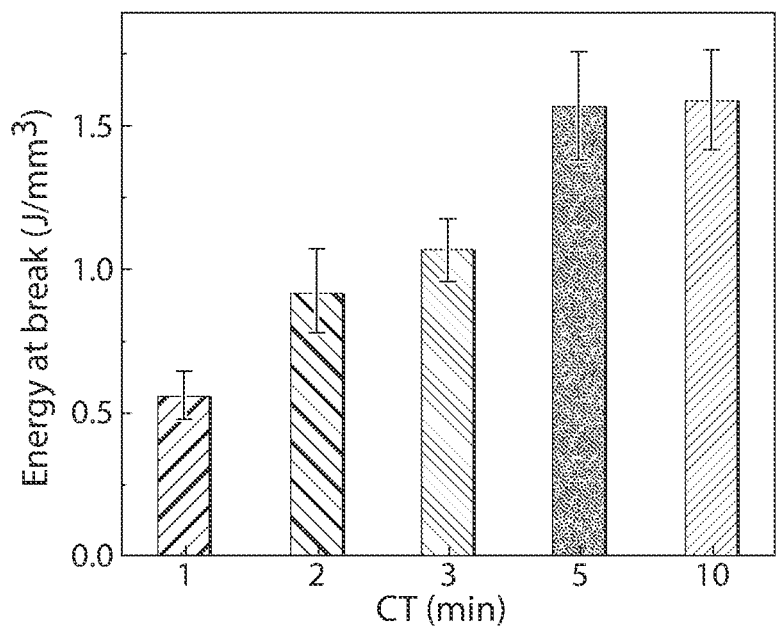
Figure 26I:
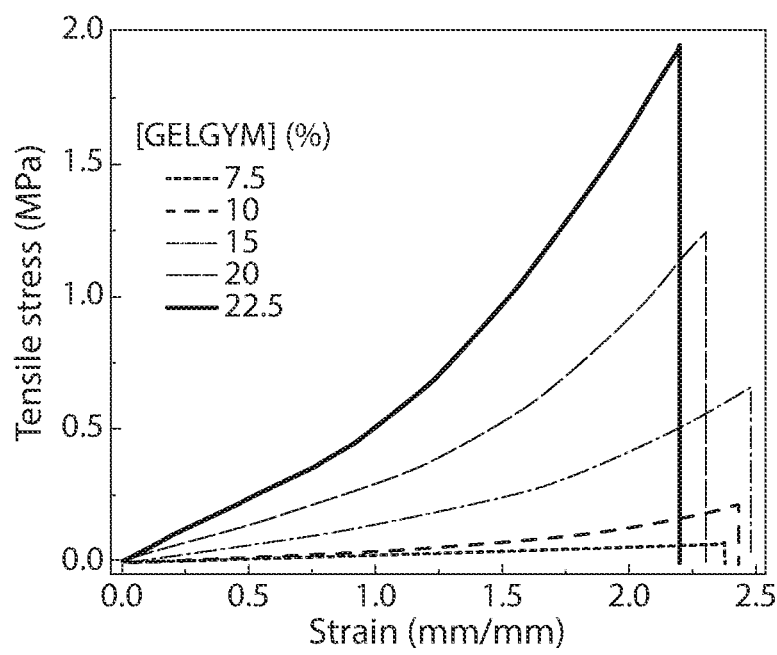
Figure 26J:
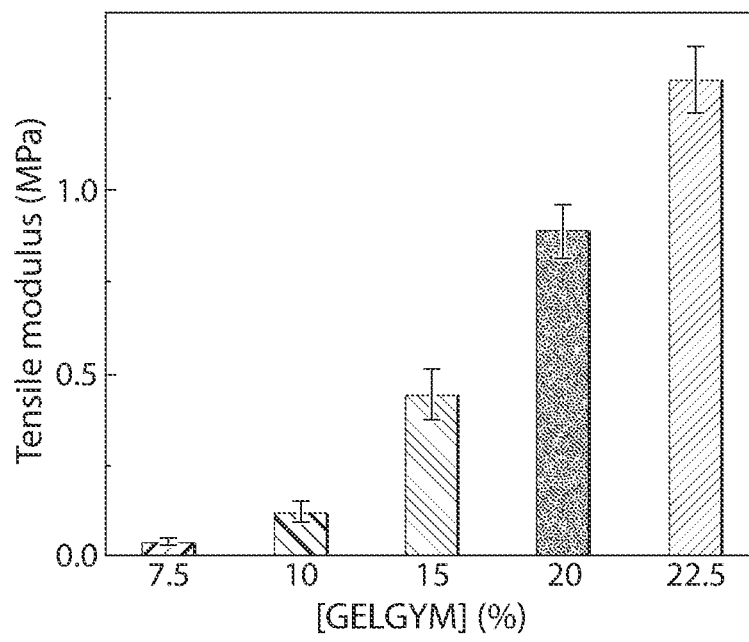
Figure 26K:
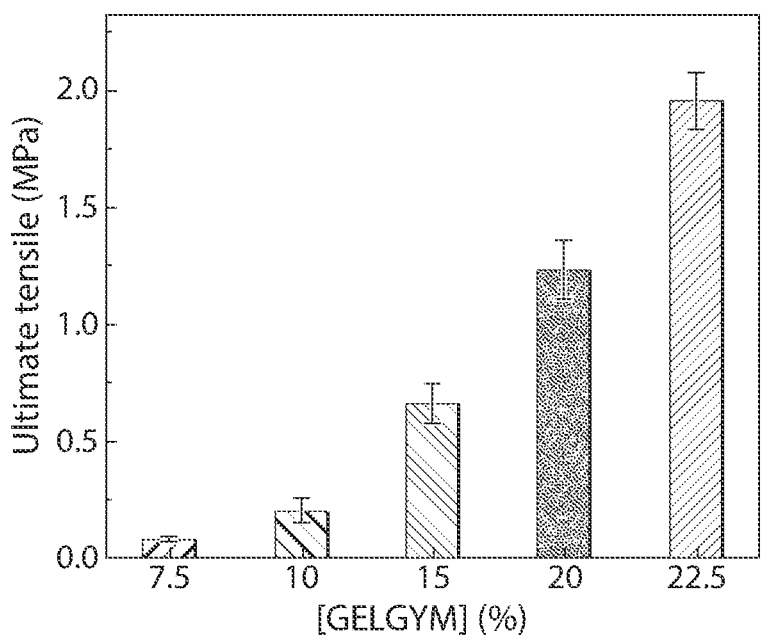
Figure 26L:
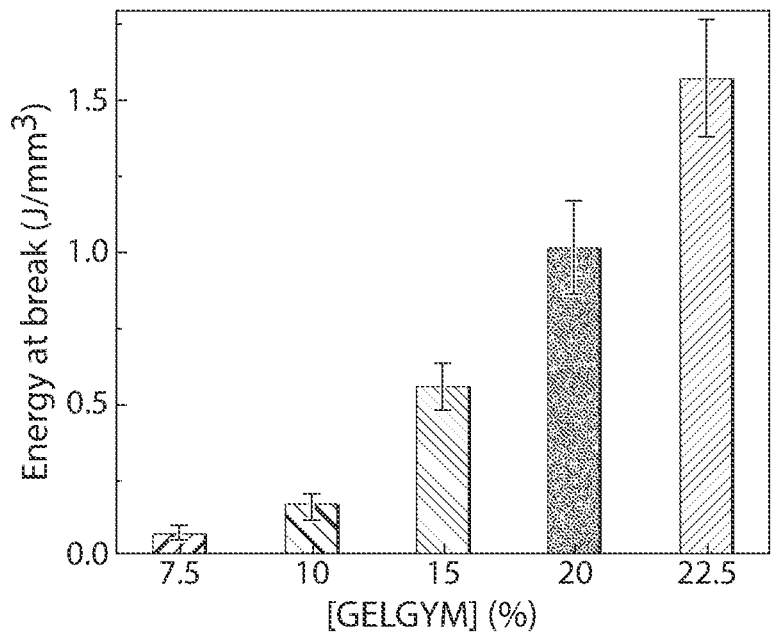
Figure 26M:
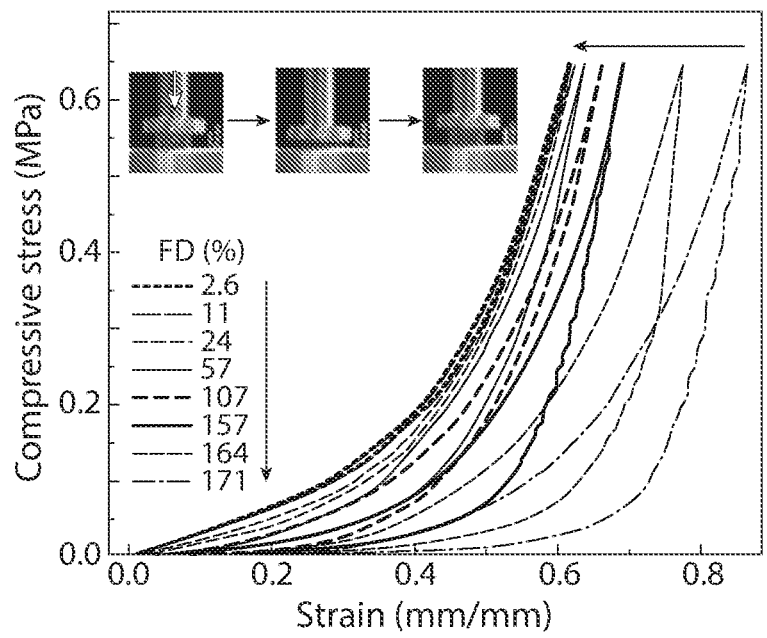
Figure 26N:
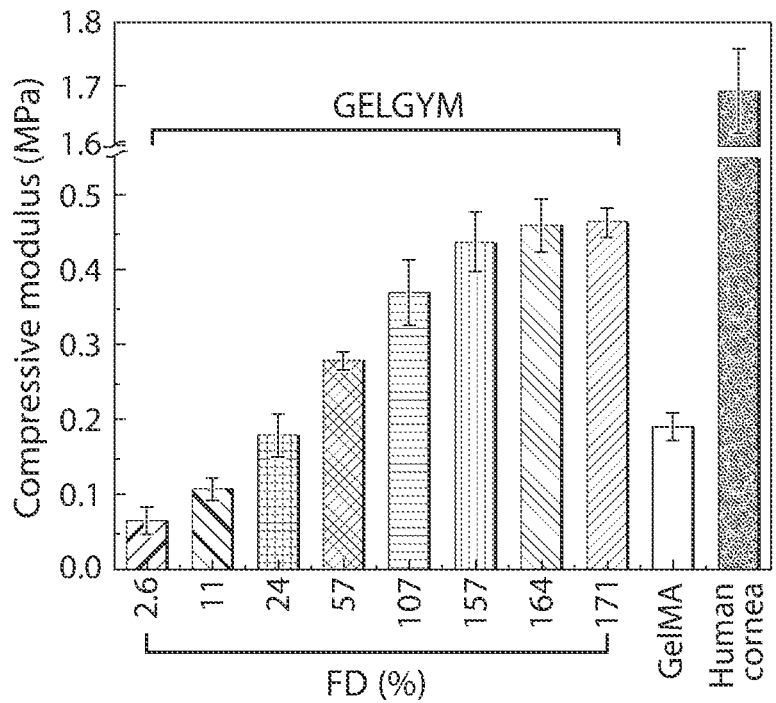
Figure 26O:
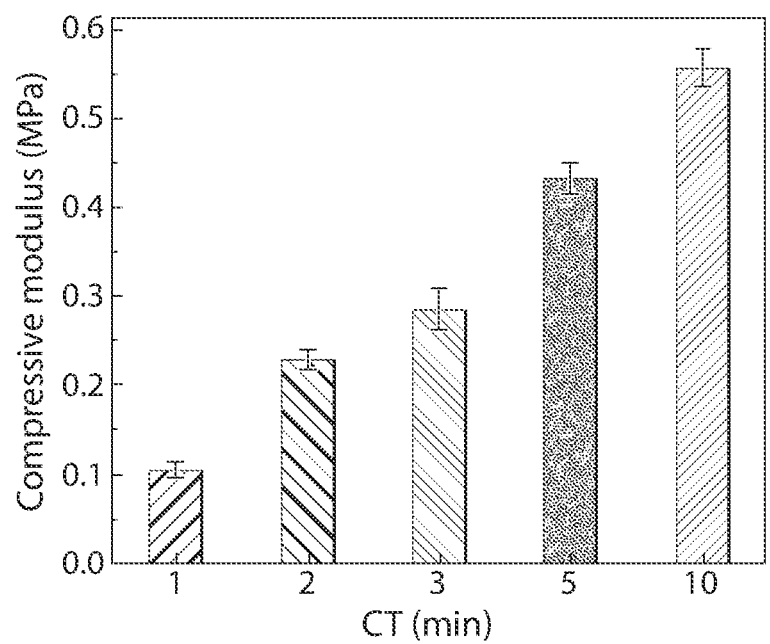
Figure 26P:
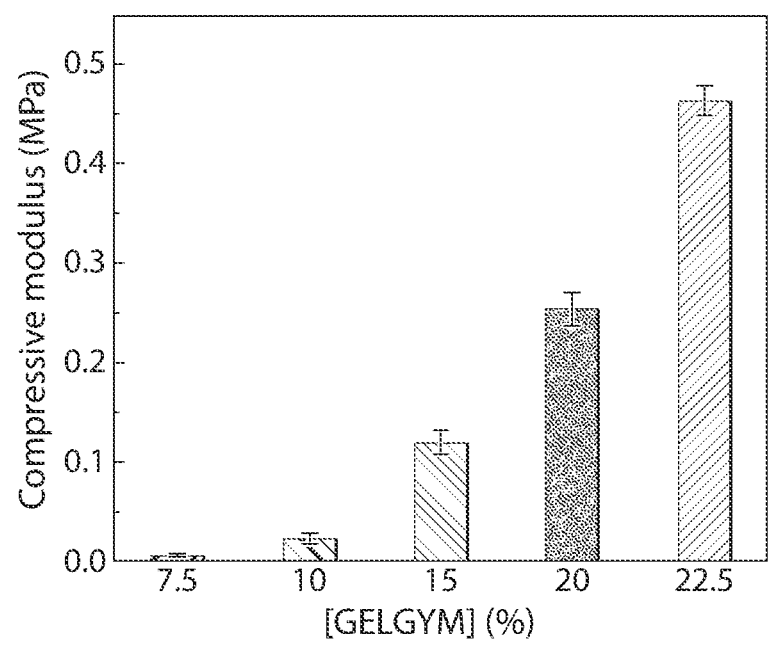

The mechanical properties of GELGYM were assessed by performing standard uniaxial tensile and compression experiments (FIG. 26a-26p and methods). Tensile measurements demonstrated that the tensile moduli, ultimate tensile, elongation and energy at break (toughness) of GELGYM samples are strongly depend on the FD of gelatin. Varying FD, the tensile moduli of the hydrogel (5 min crosslinking, 22.5% w/w) can be tuned from 0.15 MPa (2.6% FD) to ≈1.25 MPa (171% FD) compared to 14 MPa for human cornea and 0.18 MPa for GelMA in the same settings (FIG. 26a-26b). GELGYM hydrogels also have shown to withstand extremely high stresses before breakage, demonstrated by their significantly high ultimate tensile up to 1.95 MPa (171% FD, 5 min crosslink and 22.5% w/w) approaching those of the human cornea (6.9 MPa), compared to 0.1 MPa for GelMA in the same settings (FIGS. 26a and 26c). Moreover, the GELGYM hydrogels can be stretched up to 4.1 times (FIG. 26a) of their initial length with the energy at break of up to 1.6 MPa (FIG. 26d) demonstrating superior elasticity and toughness, compared to the existing hydrogels such as GelMA. In addition, our study indicated that varying crosslinking time (CT) (FIG. 26e-26h) and GELGYM concentration (FIG. 26i-26l) are also other available tools, allowing us to generate a library of GELGYM hydrogels with a wide range of mechanical properties (with the tensile moduli of ranging from 0.034 to 1.45 MPa, ultimate tensile of 0.074 to 2.05 MPa, toughness of 0.076 to 1.71 MPa and elasticity of 210-410%) according to biomedical needs (FIG. 26a-26p). Compressive stress-strain measurements of GELGYM hydrogels expressed a similar trend with the strong compressive moduli dependence on the FD of gelatin, CT and GELGYM concentrations. Our data demonstrated that via altering FD of GELGYM hydrogels, the compressive moduli of the hydrogel can be programmed from 0.07 MPa (2.6% FD) to ≈0.46 MPa (171% FD) compared to 1.69 MPa for the human cornea and 0.19 MPa for GelMA in the same settings (FIGS. 26m and 26n). Compression measurements have indicated that the GELGYM hydrogels can dissipate energy effectively as shown by the pronounced hysteresis (FIG. 26m). While the GELGYM with lower FD demonstrated greater degree of hysteresis, dissipating more energy, the ones with higher FD have shown to store more energy with an elastic behavior. Moreover, GELGYM hydrogels were able to only withstand compressive strains as high as 80% without breaking, but also recover to the initial state without deformation as depicted in FIG. 26m inset. In addition, we have shown that the compressive moduli of GELGYM can also be programmed from 0.004 to 0.56 MPa through varying CT (FIG. 26o) and GELGYM concentration (FIG. 26p). While the superior tensile and compressive strengths of GELGYM are believed to originate from an enhanced FD and subsequent greater crosslinking density, the unique elasticity is attributed to the formation of soft and flexible oligomeric ethylene glycol bridges between the gelatin backbones.

Moreover, scanning electron microscopy (SEM) was used to study the nanoporous structure of the hydrogel, demonstrating programmability of that the pore and wall thickness from 250 to 3750 μm$^2$ and 0.3 to 4.1 μm, respectively when varying CT (FIG. 19a-19f). Furthermore, our analysis noticed that CT has a direct correlation with the pore size, yet inverse correlation with the wall thickness. Although, we did not quantitatively assess the connectively of the nanopores, SEM images suggest that they are not interconnected (FIG. 19a-19e). Furthermore, we have shown that such structural properties can also dictate the glucose diffusion rate across the GELGYM membrane (data not shown). This is believed to originate from altering crosslinking density as a function of CT and can be a valuable tool to modulate not only structural properties of the hydrogel, but also its 3D cellular interaction and tissue formation. We also studied the swelling behavior of the hydrogel in PBS solution for up to 4 days at 37° C. in an incubator. The swelling ratio was shown to be tuneable from 20 to 190% of original size, depending on the CT of the GELGYM hydrogel (longer CT leads to lower swelling ratio) (FIG. 12a). This is consistent with the prior mechanical and structural evaluations and attributed to the varying crosslinking density between gelatin chains, and can be a key element to impact mechanical, mass transport and surface properties, along with the fidelity of engineered micropattern architectures for many biomedical applications.

Figure 18:
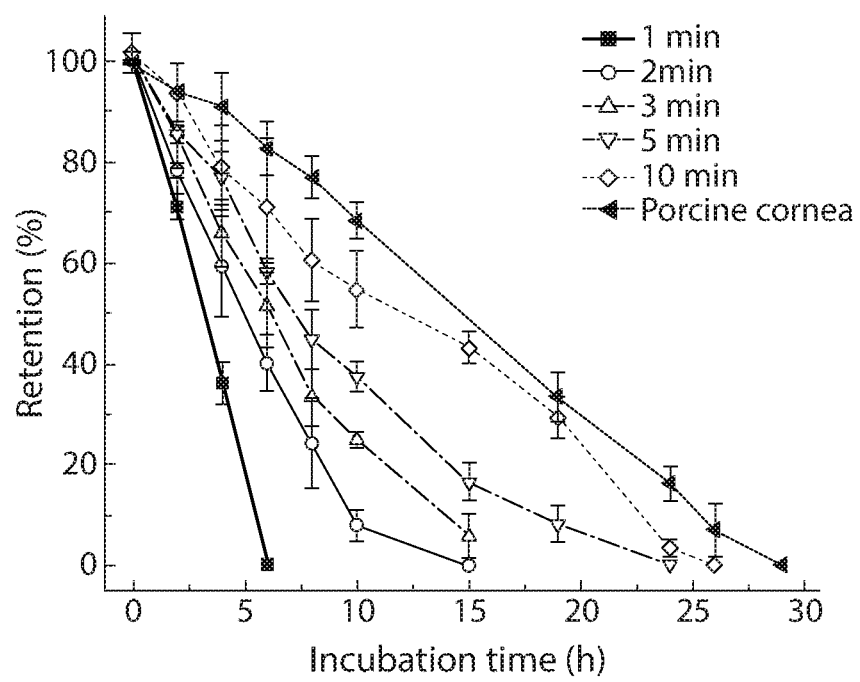
FIG. 18 is a line graph showing collagenase degradation. The degradation of GelGYM in a collagenase study can be modulated based on the crosslinking time, showing similar values to native corneas after 10 minutes of crosslinking.
Figure 19A:
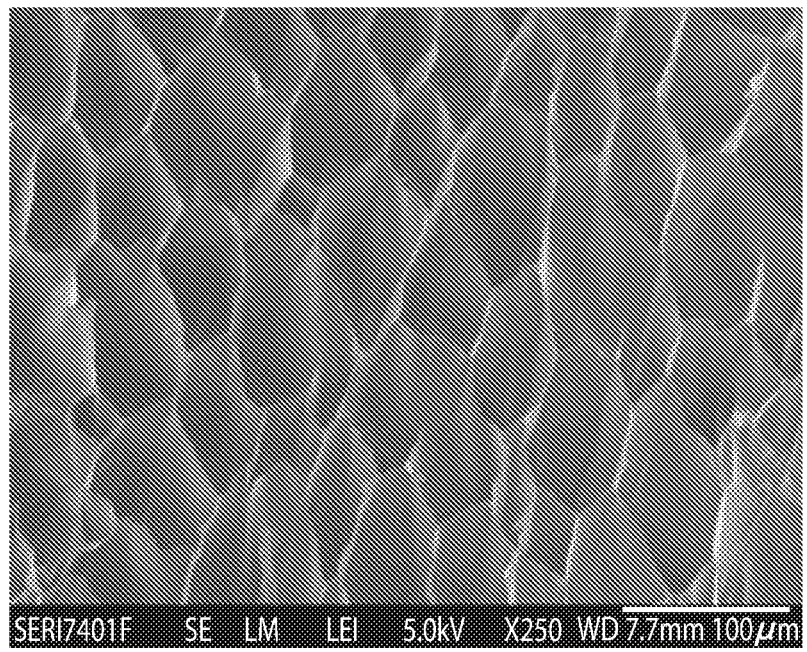
FIG. 19a-19f show characterization of the ultrastructure and porosity of GELGYM polymerized with different crosslinking times. The tunability in terms of porosity of the material can provide a perfect carrier for delivery of cells, drugs or nanoparticles.
Figure 19B:
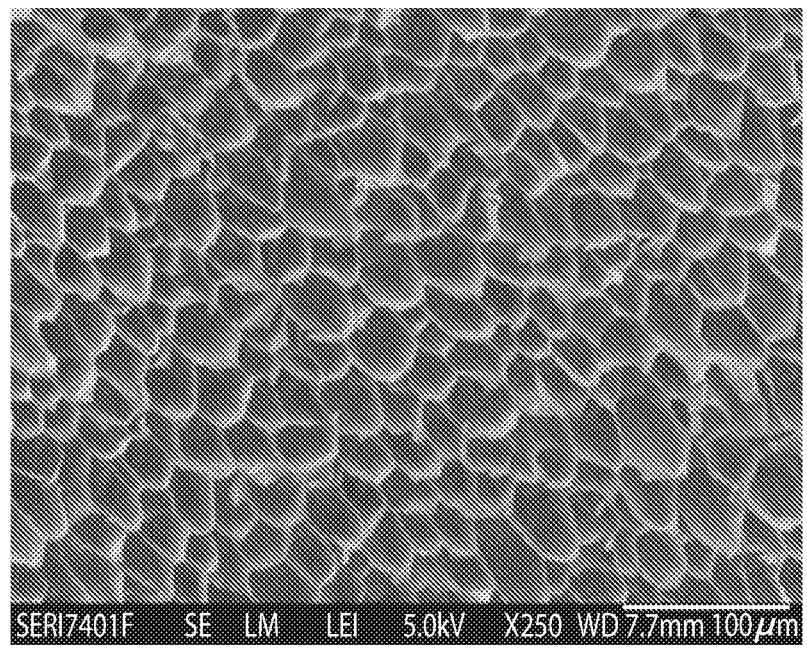
Figure 19C:
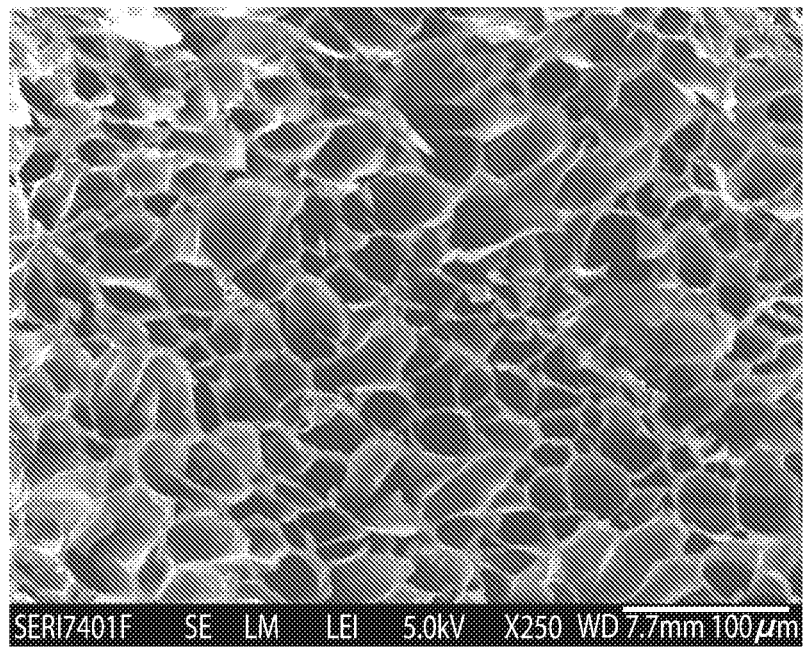
Figure 19D:
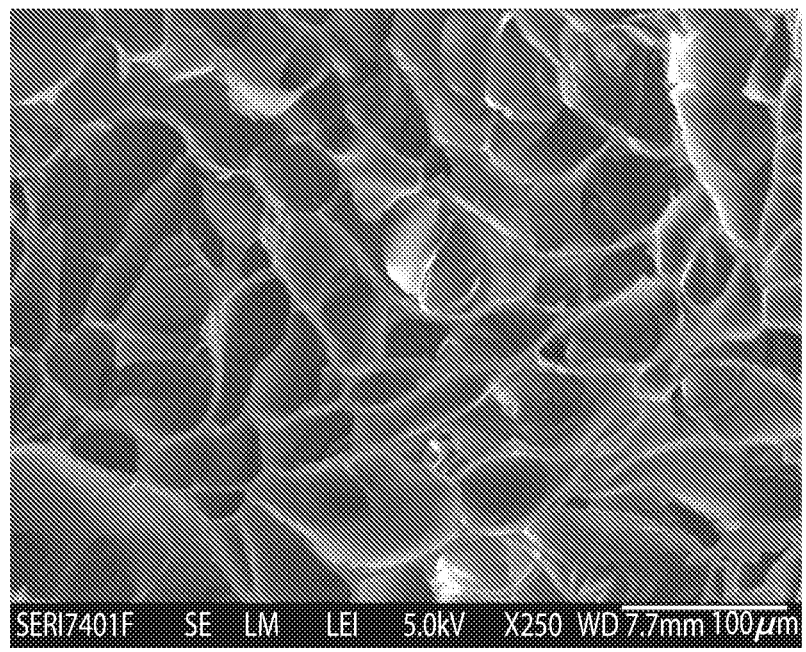
Figure 19E:
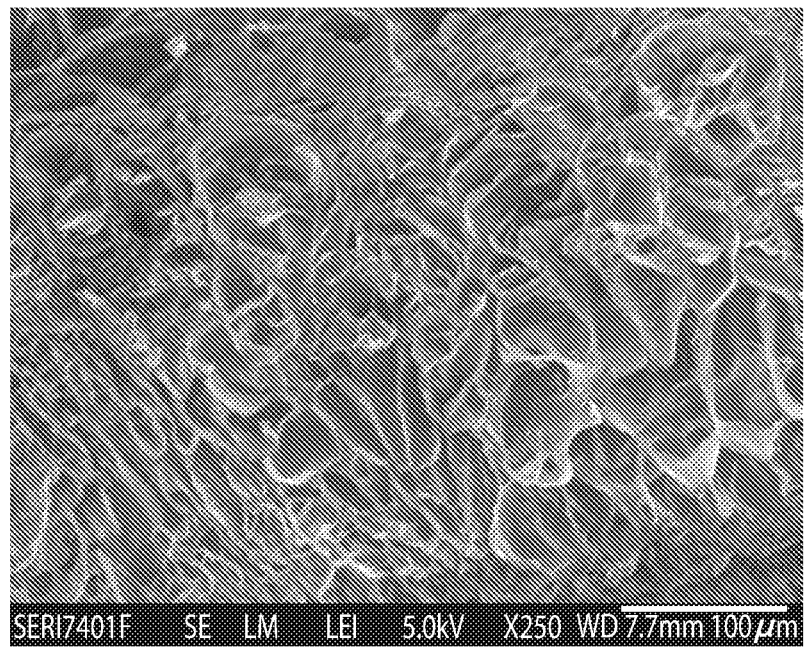
Figure 19F:
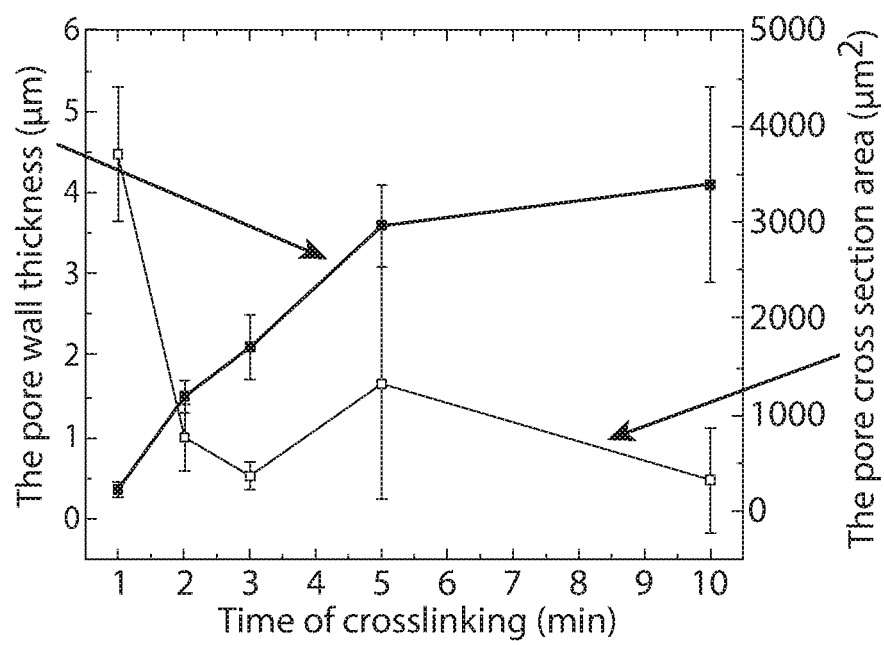

Collagenase induced degradation of the protein-based hydrogels over time leads to weakening and dissolution of the scaffold, unless there is a simultaneous tissue remodeling and regeneration process. To evaluate the stability of the hydrogel against enzymatic degradation, we have incubated the GELGYM in the solution containing collagenase, and compared the dried mass of sample to the initial mass as a function of time. Our data reveled that GELGYM, when crosslinked for longer time, has similar stability to the native tissue (i.e. porcine cornea) as shown in FIG. 18. This is due to the enhanced crosslinking density of GELGYM, which restricts the accessibility of the enzyme to the cleavage sites of hydrogel, along with increasing the anchoring points of cleavable units in the gelatin backbone. Moreover, the data revealed that the biodegradation of the hydrogel can be easily controlled from 6 to 26 hours through varying CT.

Figure 27A:
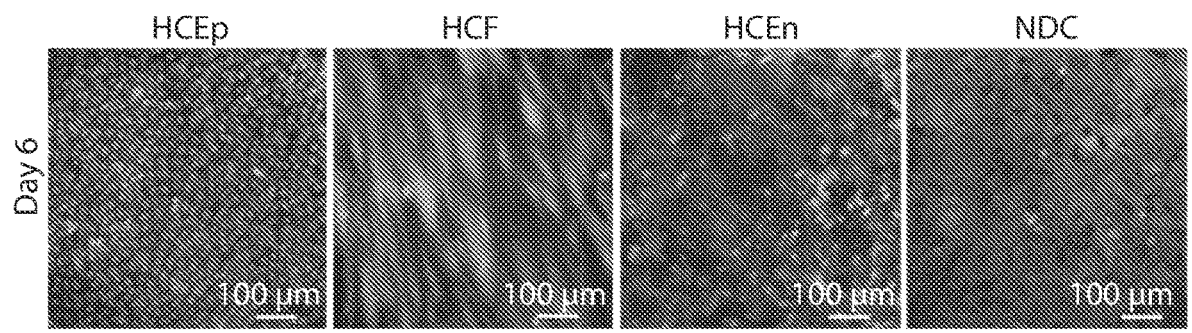
FIG. 27a-27d show biocompatibility, retention and biointegration of GELGYM.
Figure 27B:
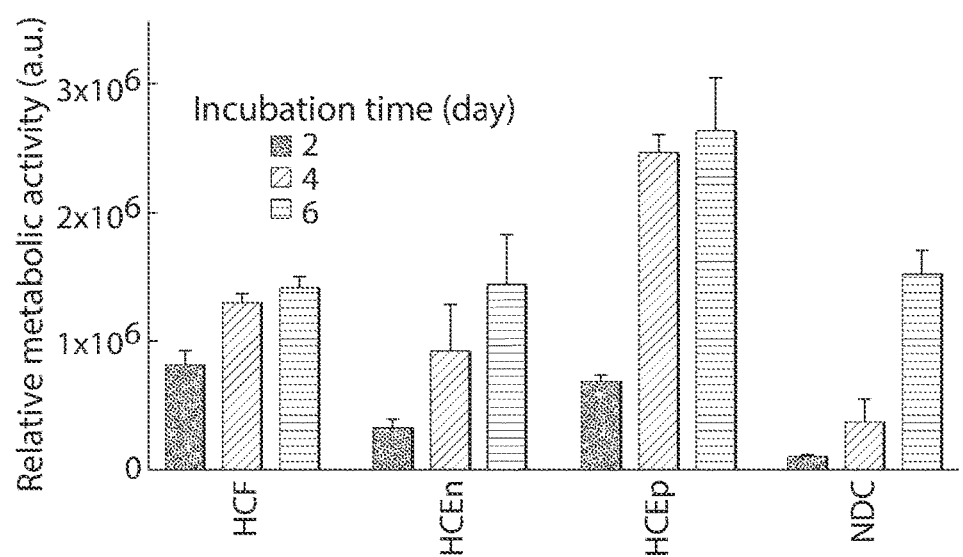

Such unique properties demand the application of GELGYM in a wide range of biomedical areas such as ophthalmology, where there is an immense need to develop an effective solution for restoration of corneal defects. This is due to crucial role of corneal in one's vision, and the high prevalence of corneal diseases, specially, in the developing countries, where millions of patients suffer from bilateral or monocular corneal blindness. Although significant progress has been made to engineer an artificial scaffold, they still fall short in emulating mechanical, chemical and other biomimetic characteristics of the native cornea. The ideal biomaterial for corneal restoration should (i) be transparent; (ii) be biocompatible; (iii) possess mechanical properties similar to the human cornea to adequately respond to the intraocular pressure fluctuations; (iv) have a strong adhesion to adjacent corneal tissue with long-term retention and biointegration; (v) have biodegradative properties that match the time of tissue remodeling and regeneration; (vi) possess appropriate porosity and hydropathicity for diffusion of nutrients, while serves as a microbial barrier; (vii) be cost-effective and easy to apply. Considering the superb structural properties of GELGYM, we postulated its potential to satisfy such ophthalmological needs. First, we evaluated the optical transmission of GELGYM using ultra-violet (UV-Vis) spectrophotometer in the range of 250-850 nm. Our measurements demonstrated that GELGYM have a similar transparency to the human cornea (FIG. 13a). Moreover, we have shown that while increasing the crosslinking time (CT) led to significant blockage of light transmission in the UV range (200-350 nm), it enhances the optical transparency in the visible range. We further performed in vitro cell biocompatibility studies (2D cell culture) to evaluate the interaction of human corneal epithelial cells (HCEp), corneal fibroblasts (HCF) and corneal endothelial cells (HCEn) along with hybrid neuroblastoma cells (NPC) with the engineered GELGYM as a function of CT. This enabled us to take into account the effect of structural properties of GELGYM with different crosslinking density on the cellular biocompatibility of the hydrogel. Standard live-dead assay indicated that all four types of cells were able to maintain nearly 100% viability after 48-hour cell culture for varying CT (i.e. 3, 5, 10 min) (FIG. 27a). Moreover, in vitro cultured cells were able to spread, migrate and proliferate, reaching full confluency in less than 6 days. The metabolic activity of all four types of cells cultured on GELGYM with varying CT was also quantified using Alamar-Blue assay. All of the studied cells exhibited a significant increase in relative fluorescence intensity as a function of incubation time, yet with a distinct pattern, suggesting an enhanced cellular activity and proliferation rate over time. This further validates the biomimetic characteristics of the engineered hydrogel, rending it as an excellent biocompatible scaffold. Moreover, there was no salient difference between proliferation rate of cells cultured in GELGYM crosslinked for different period of time, suggesting the insensitivity of biocompatibility characteristics with respect to varying structural properties.

Figure 20A:
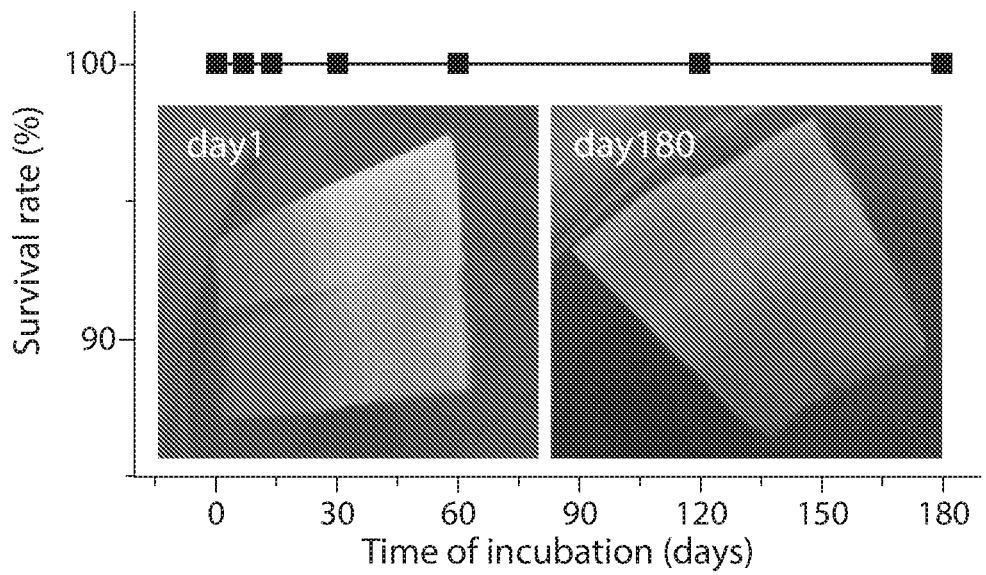
FIG. 20a-20f show retention properties of GELGYM.
Figure 20B:
Figure 20C:
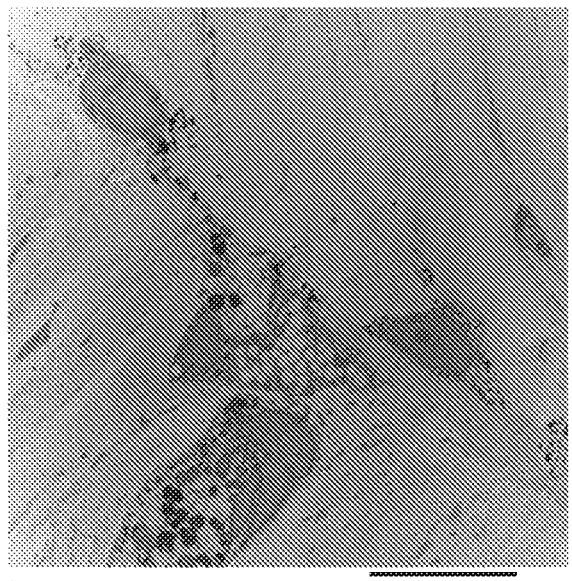
Figure 20D:
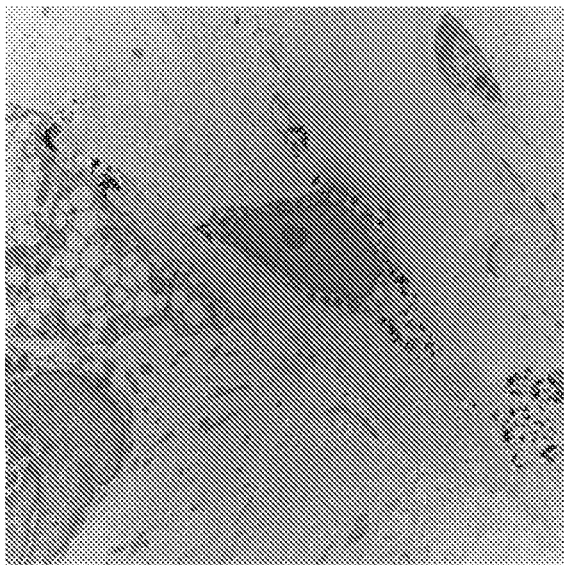
Figure 20E:
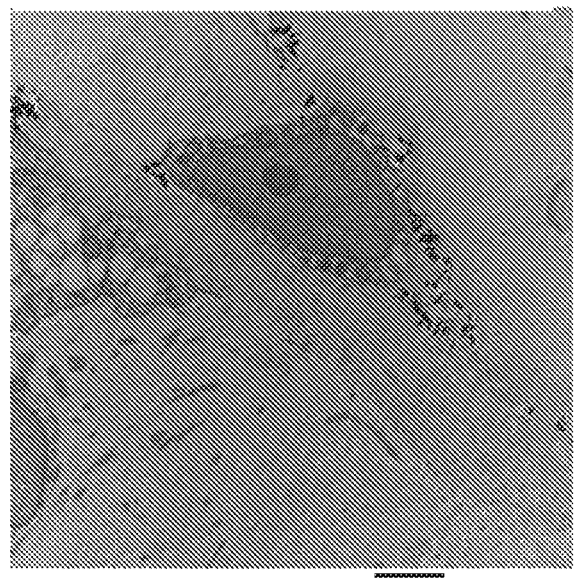
Figure 20F:
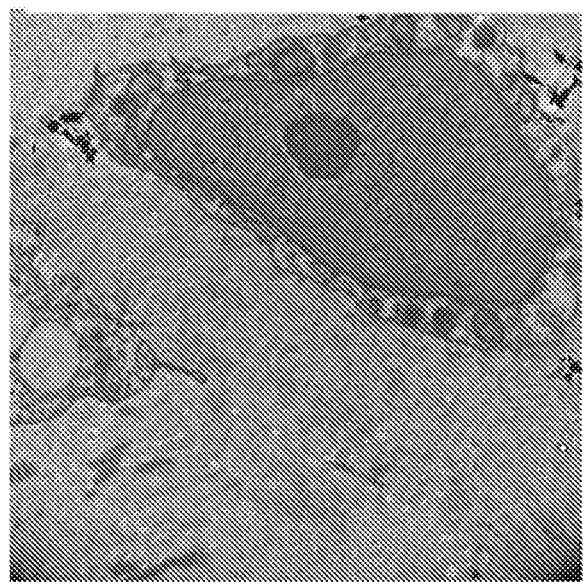
Figure 21A:
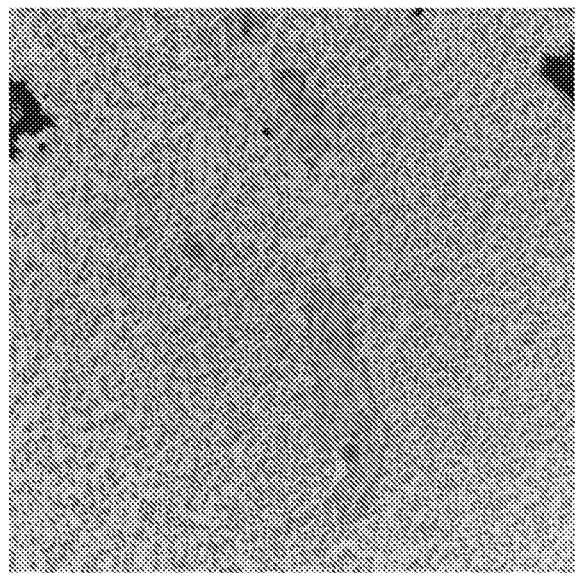
FIG. 21a-21f are representative transmission electron microscopic images of the cross-sectional interface of tissue-glue after 6-month incubation in culture media.
Figure 21B:
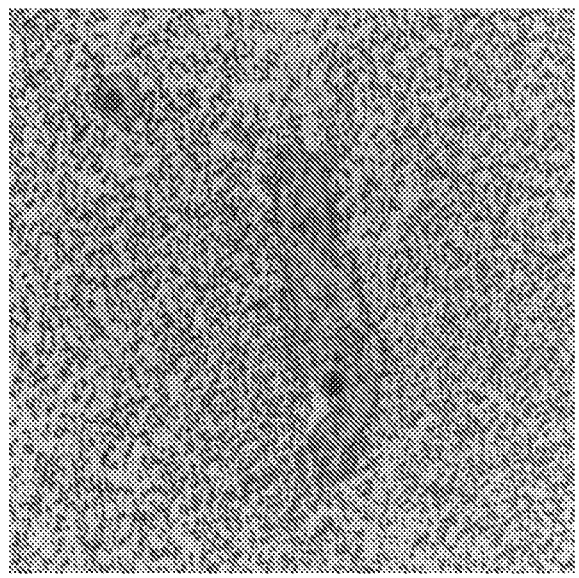
Figure 21C:
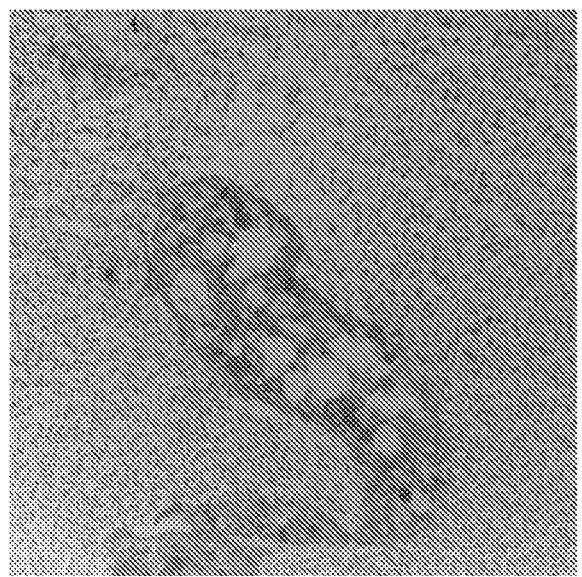
Figure 21D:
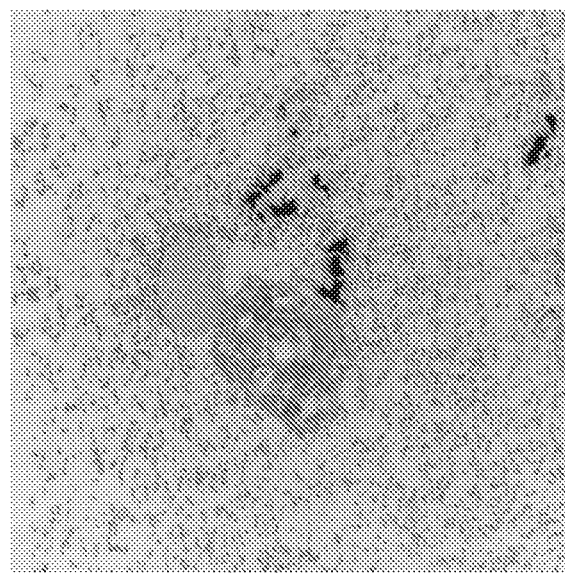
Figure 21E:
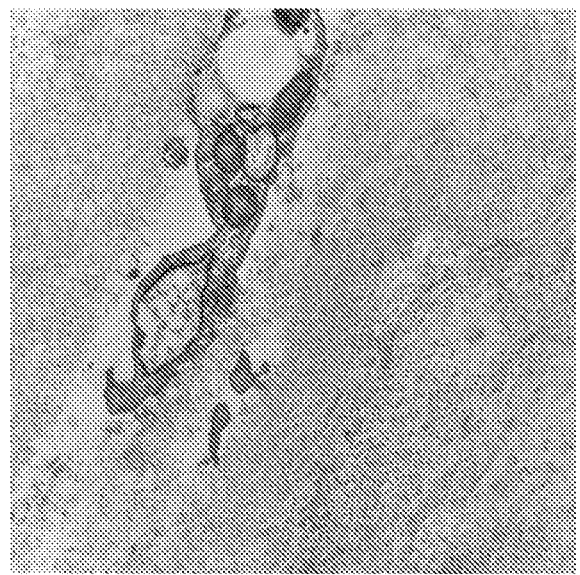
Figure 21F:
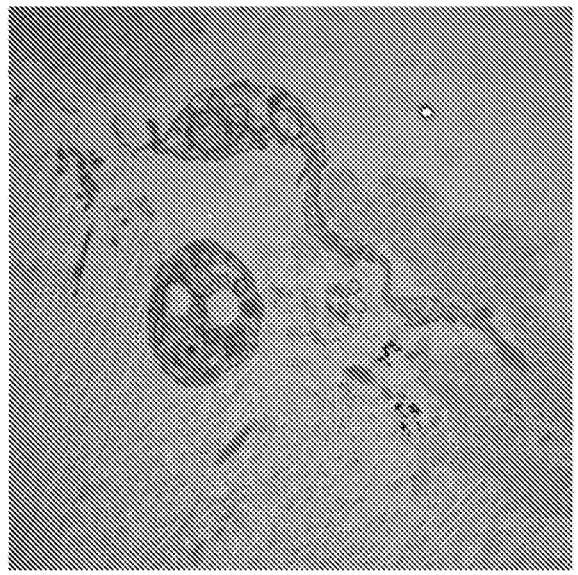
Figure 27C:
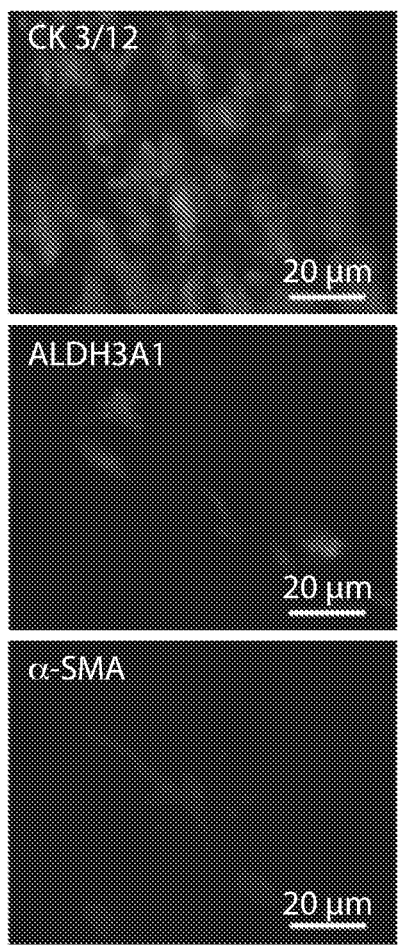
Figure 27D:
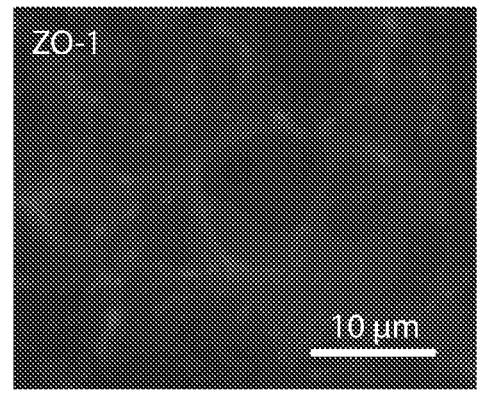

To evaluate the ex-vivo retention of the hydrogel after application in corneal tissue, we applied GELGYM as an adhesive to attach two human corneoscleral limbal pieces together and incubated them under culture conditions (FIG. 20a). Our studied revealed that the retention rate of attachment under culture was 100% until the end of the study (i.e. 6 months). While full stratified epithelialization of the glued area took place in less than a week, fibroblast migration into GELGYM happened with a slower rate. Transmission electron microscopy (TEM) revealed the presence of fibroblast into GELGYM after one month in culture. Moreover, TEM of the glued area demonstrates a perfect interpenetration of the hydrogel into the collagen lamellae of the human corneal stroma. Furthermore, simultaneous degradation of the hydrogel and the formation of new collagen fibers secreted from migrated fibroblast into GELGYM were also observed by TEM, indicating synchronized degradation and biointegration. This latter ultimately might lead to healing of the damaged area once is applied in vivo. (FIG. 27d)

Phenotypic evaluation of the human corneal epithelial cells (HCEp) and fibroblasts (HCF) were performed by immunohistochemistry. Our data revealed that the HCEp populated on the glued area expressed cytokeratin 3+12 (specific corneal epithelial markers) (FIG. 27c). It was also shown that both resided and migrated HCF expressed ALDH3A1 protein (keratocyte or corneal fibroblast marker), without expressing alpha-SMA (myofibroblast marker, associated to a fibrotic response). In addition, HCEn cultured on GELGYM scaffold has shown to express ZO-1 (corneal endothelial marker associated to the presence of tight junctions). These indicate that the interaction with GELGYM did not alter phenotypic characteristics of HCEp, HCF and HCEn, and further validating the biomimetic characteristics of the engineered hydrogel.

Corneal wound closure also begs an effective solution to replace the traditional sutures as they are associated with irritation, inflammation, infection and may lead to vascularization and astigmatisms. Although substantial efforts have been dedicated to design an effective adhesive to close corneal incisions and various biomaterials explored, none of the existing materials are capable of meeting those requirements. For instance, fibrin glue lacks required mechanical properties, degrades quickly, and may lead to viral infections and immunological reactions. PEG-based adhesives seal corneal incisions, yet are incapable of filling stromal defects, lacks cell adhesion and falls off quickly. Cyanoacrylates, while effective for treating small corneal perforations (<3 mm in diameter), have low biocompatibility and are non-degradable. To evaluate the potential of the GELGYM in ophthalmic surgery as an adhesive, we examined the adhesion strength of the hydrogel to corneal tissue using adopted burst pressure test. Our ex vivo data revealed that GELGYM have a high adhesion to the surface of cornea, and is able to seal up to 4 mm-diameter full penetrating corneal defects (FIG. 11) when used as a prepolymer solution. However, cyanoacrylate could only seal 2-mm perforations in similar settings as previously has been described. In addition, our data has also demonstrated that GELGYM can function as a tissue adhesive and attach either corneal graft or precrosslinked GELGYM patch to larger perforations (e.g. 6-8 mm), withstanding pressures as high as 200 mmHg. Given its superior mechanical and adhesion properties, GELGYM can also function as carrier for keratoprosthesis implantation without the need for donor cornea and can be glued to the host tissue. Such strong adhesion is believed to stem from covalent bonding of amine groups substituents of proteins in the tissue with α,β-unsaturated ester functionalities of GELGYM through Michael addition, along with hydrogen-bonding, electrostatic and hydrophobic interactions and physical anchoring of crosslinked chains interlocked in the microscopic pores of the tissue. In addition, our studies revealed that the increasing CT significantly improves the adhesion strength (measured by burst pressure) of GELGYM. This is believed to stem from improving mechanical properties of the hydrogel, approaching those of the native tissue, leading to harmonized distribution of applied forces as the crosslinking reaction progress along with enhancing physical anchoring. In vivo application of the GELGYM as an adhesive sealant in anterior lamellar keratoplasties has further demonstrated the biocompatibility and effectiveness of the GELGYM in ophthalmology. Our studies indicated that while there was no sign of inflammation, the GELGYM retained the transparency with a smooth surface until the end of planned study (1 month). Histological evaluation of harvested rabbit corneas after one month demonstrated full epithelialization over GELGYM along with migration and proliferation of fibroblasts inside of the hydrogel, indicating harmonized biodegradation and biointegration process which leads to wound healing.

Figure 23A:
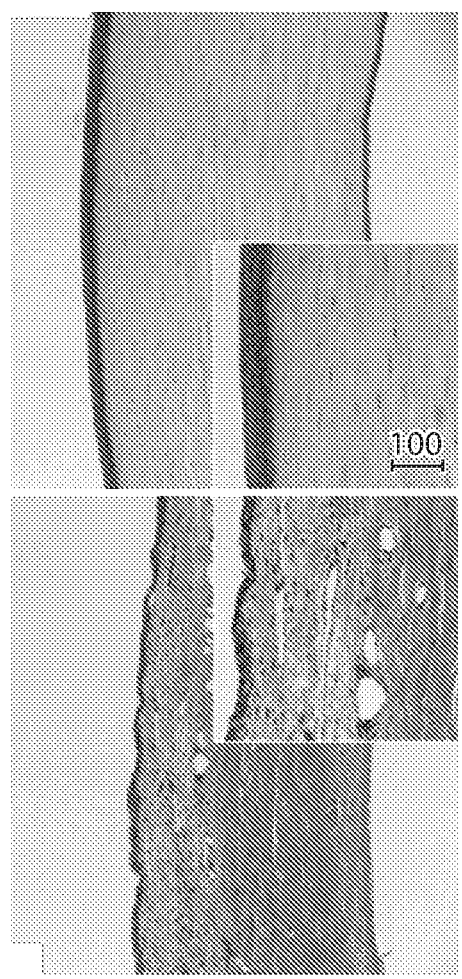
FIG. 23a-23d show applications of GELGYM in tissue engineering.
Figure 23B:
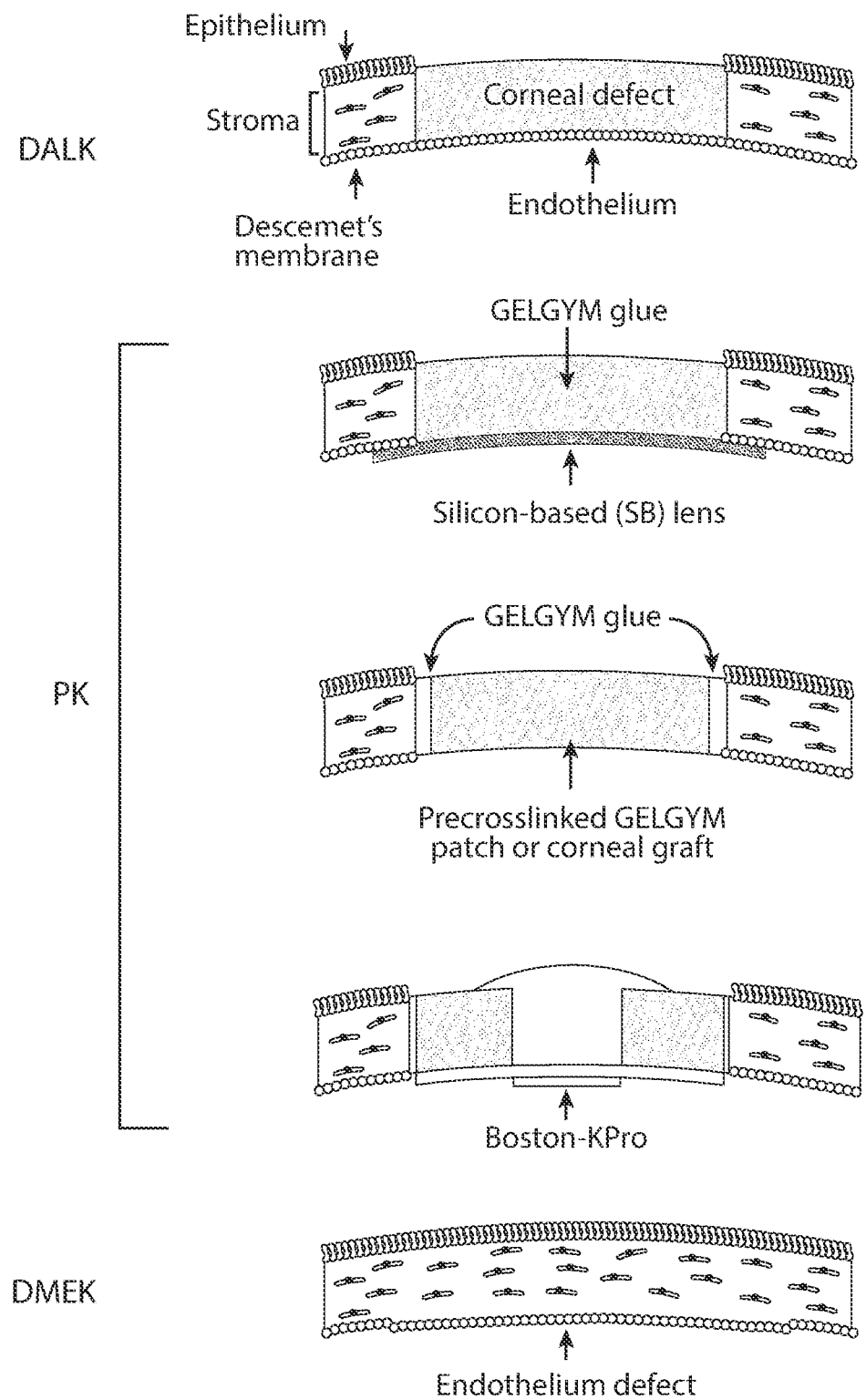
Figure 23C:
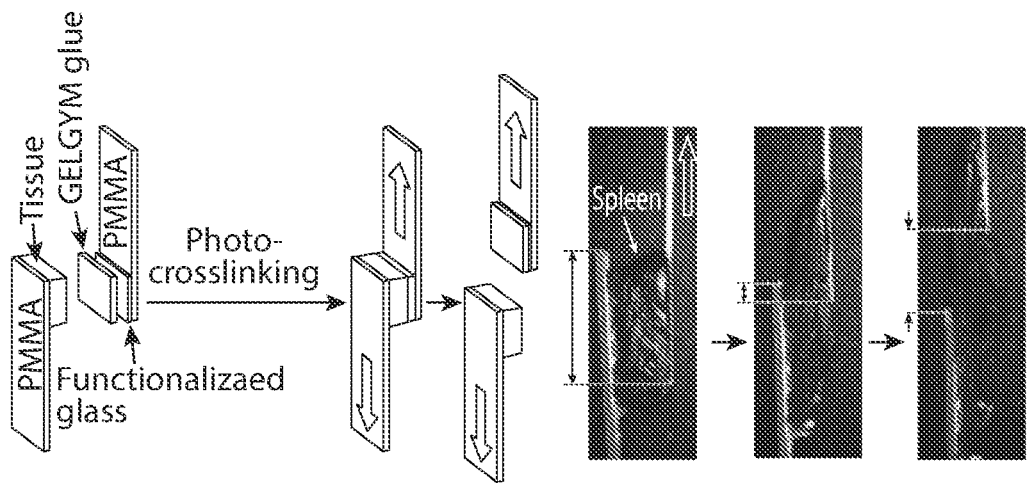
Figure 23D:
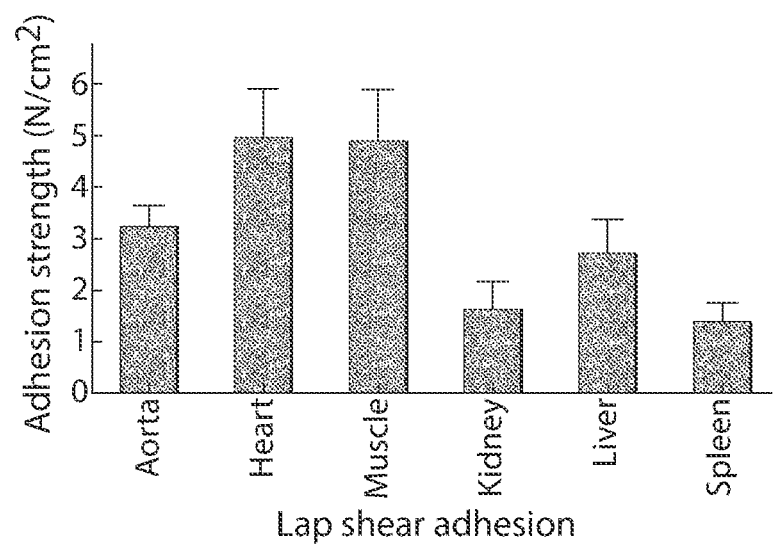
Figure 24A:
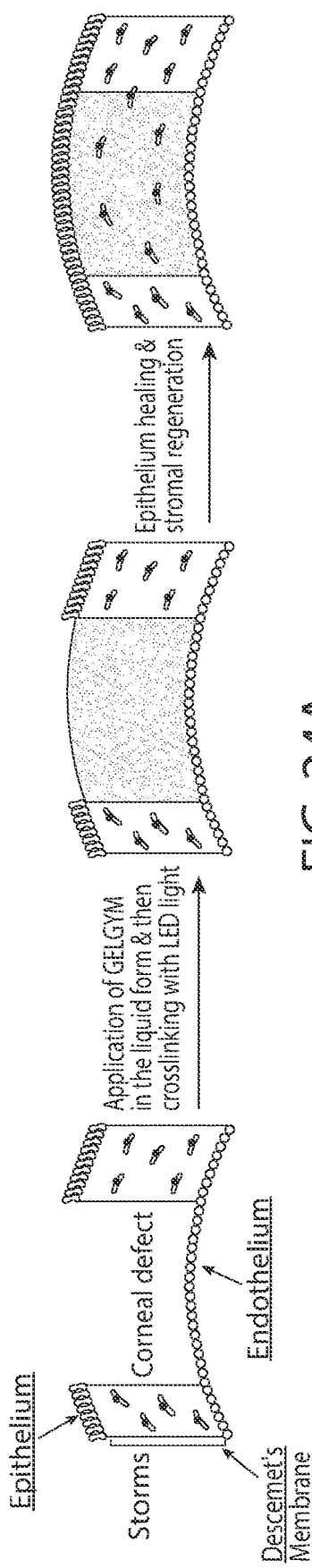
FIG. 24 is schematic diagram showing application of GELGYM for non-penetrating and penetrating corneal defects.
Figure 24B:
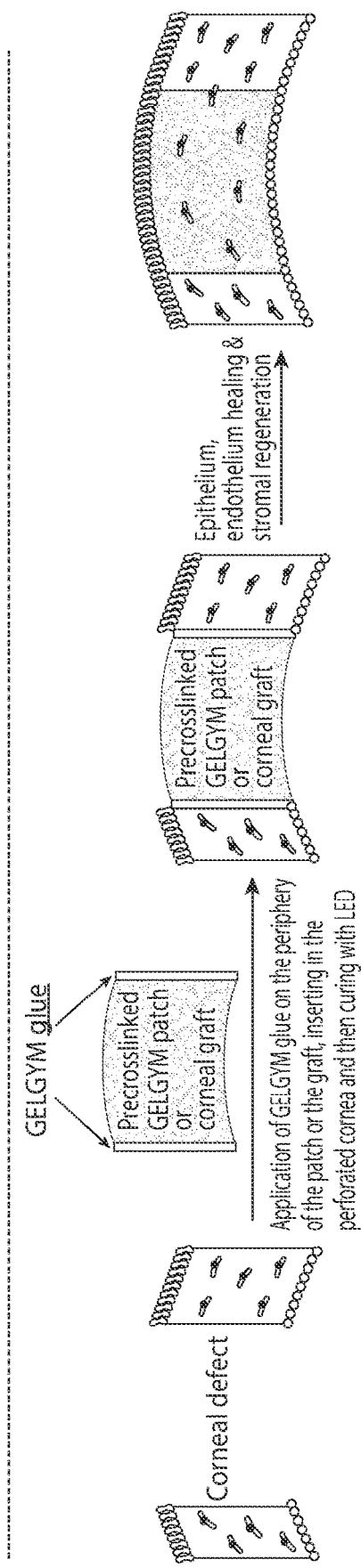

Considering such unique properties, we envisioned that GELGYM have a potential to satisfy various needs in ophthalmology including, (i) as an adhesive sealant for corneal or corneoscleral lacerations facilitating an instant primary closure, (ii) as a corneal glue for facilitating sutureless grafting in anterior, endothelial and penetrating keratoplasties, and (iii) as a corneal stromal substitute to generate an immediate sutureless keratoplasty without the need of a donor corneal stroma in anterior lamellar keratoplasties, penetrating keratoplasties, including keratoprosthesis implantation, and endothelial keratoplasties. Our ex vivo studies have demonstrated the successful application of GELGYM either as adhesive or as substitute for the aforementioned applications as indicated by optical coherence tomography (OCT) and burst pressure experiment (FIGS. 11 and 23b).

Additionally, we envisaged the application of GELGYM for various organs and tissues. As a proof of concept, we performed a standard lab shear test to study the adhesion of GELGYM with various dynamic wet biological surfaces. We have shown that GELGYM can strongly adhere to the wet surface of aorta, heart, muscle, kidney, liver and spleen, superseding by far the adhesion strength of most of widely used adhesives such as fibrin glue (Evicel) and PEG-based adhesive (Duraseal) with shear strength of 0.1, 0.6 N/cm$^2$, and approaching cyanoacrylate (Omnex, with 2.9 N/cm$^2$). Moreover, our data revealed that the adhesion strength strongly depends on the structural properties of the tissue. Tuneable properties of GELGYM along with its biological active matrix, ease and biosafety of processing have also driven us to evaluate the potential of the hydrogel for 3D cell culture. Our data revealed that encapsulated fibroblasts not only retain high viability but also can spread, migrate and proliferate up to 30 days post seeding, yet with different rates corresponded to the varying CT, as demonstrated by standard live-dead assay (FIG. 27a). This further validates the biomimetic characteristics of GELGYM to imitate the native ECM, and provide a biologically active microenvironment to support cell-matrix and cell-cell interactions.

We demonstrated that GELGYM is programmable hydrogel with a strong adhesion to the wet biological tissues and long retention. It is also biocompatible with a wide range of structural and biodegradative characteristics, controlled by varying FD, CT, and prepolymer concentration, allowing to customize the properties according to the medical needs. These along with ease and biosafety of processing (crosslinked with low intensity of visible light and low concentration of the crosslinking reagents) to create 3D cell encapsulated constructs further emphasize the application GELGYM to many biomedical research areas such as transplantation, tissue adhesives and sealants, immobilizing medical devices, 3D-bioprinting, differentiation studies, drug discovery, cancer research, gene expressions studies and for the understanding of cell physiology.

Methods:

Chemical synthesis of GELGYM: To synthesize GELGYM with different FD, 8.0 g of gelatin was dissolved in 80 ml of PBS and equally divided to 8 vials (20 ml). Then, varying amount of gylcidyl methacrylate (0.0125, 0.025, 0.05, 1.0, 0.2, 0.4, 0.8, 1.6 ml) was added to different vials to form varying concentration of gylcidyl methacrylate (0.009375 to 1.2M). The reaction mixtures were agitated for 4 h at 45° C., diluted with 10 ml deionized water (DIW), and then dialyzed for 1 week using dialysis membrane with molecular weight cut-off of 14000. Then they were freeze-dried for 3d to obtain foam-like GELGYM precursors with different FD.

Crosslinking conditions: To prepare a GELGYM solution with different precursor concentration, 2.45 ml of PBS was added to varying amount of GELGYM (0.334, 0.445, 0.667, 0.890 and 1.00 g) and agitated at 45° C. to generate a homogenous solution. Then, the solution was mixed with 1.0 ml solution containing Eosin Y (0.22 mM), triethanolamine (1.78% w/v), and vinyl caprolactam (1.78% w/v) under dark condition, and centrifuged at 5000 rpm at 45° C. to eliminate any bubbles. Afterwards, the resulting prepolymer solution was carefully transferred to an appropriate mold or applied to the desired structure and crosslinked for varying time (1, 2, 3, 5 and 10 min) using our hand-made visible light source (i.e. LED with wavelength of 505-515 nm and the intensity of 20 mW/Cm$^2$) to cure the hydrogel.

Chemical characterization ($^1$H-NMR): A small amount of the GELGYM (10 mg) mixed with 0.5 ml of D20 in a NMR tube, and heated for nearly 30 min at 40° C. to fully dissolve the precursor. Then $^1$H-NMR spectrum of the samples was acquired using Bruker 400 MHz NMR. In case of the $^1$H-NMR spectrum of the samples after crosslinking, 80 μl of the prepolymer solution was transferred to a cylindrical mold (0.6 mm diameter, and 0.2 mm depth), crosslinked and washed with copious amount of DIW. Afterwards, the samples were incubated in 2 ml collagenase solution (10 U/ml), containing 0.1M Tris-HCl buffer (pH 7.4) supplemented with 5 mM $CaCl_2$ at 37° C. to digest the hydrogel and form homogenous solution. Then, the solutions were freeze-dried to eliminate the water, and similar to non-crosslinked samples were dissolved in $D_2O$ and their H-NMR spectra were acquired.

Mechanical Characterization:

Tensile Strength: First, 0.1 ml of the prepolymer solution with different FD and GELGYM concentration was transferred to an appropriate dumbbell-shaped poly(dimethylsiloxane) (PDMS) mold (total length of 15 mm, a gage area of 3×1 mm², grip area 6×4 mm² and thickness of 1 mm), and the crosslinked for varying period of time (1, 2, 3, 5 and 10 min) and immediately placed in mechanical tester (Mark-10 ESM 303 equipped with MESUR Gauge Plus software, and load cell of 50N), and the stress was recorded as a function of the strain with crosshead speed was 2 mm/min. The obtained stress/strain curve was used to extract elastic modulus, ultimate tensile strength, elongation and energy at break for each hydrogel [n=8].

Compressive Strength: First, 80 µl of the prepolymer solution of GELGYM with different FD and concentration was transferred to a PDMS mold (0.7 mm diameter, and 0.2 mm thickness), crosslinked for varying period of time (1, 2, 3, 5, 10 min) and immersed into PBS solution for 5 min (FIG. X & SI section FIG. SX). Then, the compression test was performed on the resulting disc-shaped hydrogels using mechanical tester with crosshead speed was 0.5 mm/min, and the compressive stress was recorded as a function of the strain. The obtained stress/strain curve was used to extract compressive modulus of each hydrogel [n=8].

Electron scanning microscopy: To analyze the microstructure of GELGYM, 80 µl of the prepolymer solution of GELGYM with the concentration of 22.5% w/w "GELGYM solution" was transferred to a PDMS mold (7 mm in diameter and 2 mm in thickness) and crosslinked for varying period of time (1, 2, 3, 5, 10 min), followed by immersing in DIW for 1 h. Then, the samples were frozen in dry-ice and lyophilized. Afterwards, they were cut to expose their cross-sections, coated with gold using a sputter coater, and imaged using a field emission scanning electron microscope (FE-SEM, S-4800, Hitachi, Japan) under an accelerating voltage of 5 kV. The average pore size and the wall thickness of the scaffolds were quantified by ImageJ. Software [n=4].

Swelling ratio: To measure the swelling ratio, 80 µl of the GELGYM solution was transferred to a PDMS mold (7 mm in diameter and 2 mm in thickness) and crosslinked for varying period of time (1, 2, 3, 5, 10 min). The resultant disc-shaped hydrogels were rinsed with DIW, and their surface water was removed to obtain their initial wet weights (WO, before their immersion in the PBS solution and incubated at 37° C. After predetermined period of time (i.e. 1-4d), swollen hydrogel samples were rinsed with DIW, their surface water was removed, and swollen weights ($W_s$) were measured. The swelling ratio (S) for the hydrogels [n=5] was obtained according to as the following equation:

$$S\ (\%) = \frac{(W_s - W_i)}{W_s} \times 100$$

Glucose diffusion: Static Franz cell system composed of 1-ml upper cell cap and a 5-ml lower receptor chamber with the diameter of 9 mm (PermeGear 6G-01-00-09-05) was used to measure the permeability of the GELGYM hydrogels and corneal samples. First, 200 µl of the GELGYM solution was prepared and transferred to a PDMS mold (15 mm in diameter and 1 mm in thickness), crosslinked for varying period of time (1, 2, 3, 5, 10 min) and washed with copious amount of DIW to yield a GELGYM membrane. Those membranes along with 15-mm diameter discs of trephined fresh porcine corneas (control groups) were immediately inserted between the two compartments of Franz cell, creating a barrier between the two chambers. The upper section was filled with 1 ml PBS and the bottom part was filled with 5 ml glucose solution (2000 mg/dl). Both chambers were equipped with a small stirrer bar, and the solutions were mixed with magnetic stirrer throughout the experiment, and the entire unit was placed inside of an incubator at 37° C. After glucose diffused through the membrane for different time points, the glucose concentration in the upper chamber was measured using a Counter Next EZ blood glucose meter (Bayer) with the test strips. For each group [n=4], the diffusion coefficient was calculated using the method previously described by Myung et al (Myung D, Derr K, Huie P, Noolandi J, Ta K P, Ta C N. Glucose permeability of human, bovine, and porcine corneas in vitro. Ophthalmic Res 2006, 38(3): 158-163).

Optical Transmission: The optical transmission of the GELGYM hydrogels along with human cornea were examined by a UV-Vis spectrometer (Molecular Devices SpectraMax 384 Plus Microplate Reader). First, 40 µl of the GELGYM solution was transferred to a PDMS mold (6 mm in diameter and 1 mm in thickness) and crosslinked for varying period of time (1, 2, 3, 5, 10 min) to yield disc-shaped constructs. Those constructs along with 6-mm diameter trephined discs of fresh human corneas (control groups) were placed in a 96-well quartz microplate, filled with DIW, and their optical transmittance were recorded from 250-850 nm in quartz microplate at 1-nm wavelength increments. The transmittance of the samples [n=4] was corrected with blank media (DIW) and the mean transmittance (%) for each group calculated and plotted as a function of wavelength.

In vitro Biodegradation: Enzymatic degradation of GELGYM hydrogels were evaluated using collagenase from *Clostridium histolyticum* (Sigma-Aldrich), as previously described. Briefly, 80 µl of the GELGYM solution was transferred to a PDMS mold (6 mm in diameter and 2 mm in thickness) and crosslinked for varying period of time (1, 2, 3, 5, 10 min) to yield disc-shaped constructs. Then, they were washed with plentiful DIW, lyophilized and weighed to obtain their dried weight ($W_i$). Afterwards, they were soaked in PBS solution for 1 h to reabsorb the water, and along with 6-mm trephined fresh porcine cornea (control group) were placed in a solution containing 5 U/ml collagenase in 0.1M Tris-HCl (pH of 7.4) buffer, supplemented with 5 mM $CaCl_2$ and incubated at 37° C. The collagenase solution was changed at every 8 h and the residue was carefully removed from the solution, rinsed with DIW and lyophilized, and its dried mass at different time points ($W_f$) was weighed. The degradation rate was calculated [n=4] using following equation:

$$\text{Residual mass}\ (\%) = \frac{W_f}{W_i} \times 100$$

In Vitro Biocompatibility:

Live-Dead Assay: To evaluate the interaction of HCEp, HCF, HCEn and NPC with the GELGYM surface, we performed standard live-Dead assay. Briefly, 40 µl of the GELGYM solution was transferred to a PDMS mold (15 mm in diameter and 1 mm in thickness), crosslinked for varying period of time (3, 5 and 10 min), and washed with plentiful DIW and immersed in PBS overnight. Then, they were trephined with 6 mm biopsy punch to generate 6-mm "culture discs" which then were transferred to 96-well plate. Almost 10,000 of cells (i.e. HCEp, HCF, HCEn and NPC)

were seeded on each disc, followed by addition of 100 µl appropriate media and incubated at 37° C. and 5% $CO_2$ condition. Cell culture media were changed every 3-day to retain experimental consistency. After 6 days of incubation, live-dead staining was performed on the cultured discs using staining kit (Life Technologies Corporation), where cells were double-stained by calceinacetoxymethyl and ethidium homodimer and imaged by inverted fluorescent microscope (Zeiss Axio Observer Z1) with 10× objective. Four samples per each group were tested and compared tissue culture well plate as a control group.

AlamarBlue assay: To access the metabolic activity of the cells cultured on the GELGYM discs, we used standard Alamar Blue assay. Briefly, HCEp, HCF, HCEn and NPC (10000 per each well) were seeded on the GELGYM culture discs with varying CT (3, 5 and 10 min), followed by addition of 100 µl appropriate media as previously described and incubated at 37° C. and 5% $CO_2$ condition. The AlamarBlue study was performed at day 2, day 4 and day 6 after cell seeding. At every time point, the media was removed and replaced with the 100 µl new media containing 0.004% w/v resazurin sodium salt (Sigma), and incubated for 2 h. Afterwards, 95 µl was removed from each well and pipetted into a new 96 well plate and read on a BioTek plate reader (Synergy 2, BioTek Instruments) at 530/25 nm for excitation and 600/25 nm for emission, and corrected with the fluorescence of GELGYM discs incubated without cells. Four samples per each group and data points were tested and compared to tissue culture well plates as a control group (corrected with TCP without cells) and reported as mean±standard deviation.

Ex vivo Retention Test: To evaluate the retention of the GELGYM, human cornea from several donors was each sliced into 16 pieces. Afterwards, the GELGYM solution was applied in the intersection of two fragments, and cross-linked for 5 min. Then, those glued fragments were incubated under culture conditions in the appropriate media for 6 months (end of experiment), and the retention rate was extracted from the number of constructs retaining the glue compared to beginning of the experiment.

Transmission electron microscopy (TEM): After 1, 3 and 6 months, the glued fragments from the retention test were removed from media, fixed in 4% paraformaldehyde, and then also fixed with to half strength Karnovsky's fixative (pH 7.4) (Electron Microscopy Sciences), before placing them in fresh Karnovsky's fixative for 4 h. Afterwards, the samples were washed (with three repeats) with 0.1M Cacodylate Buffer (Electron Microscopy Sciences) for 5 min, and then rinsed with PBS. Then, the specimens were post-fixed with 2% osmium tetroxide (Electron Microscopy Sciences) for 1.5 h, and stained with en bloc in 2% aqueous uranyl acetate for 30 min. Afterwards, the samples were dehydrated in ethanol, and embedded in epoxy resin (Tousimis). Ultrathin sections (80 nm) were then cut from each sample-block using a Leica EM UC7 ultramicrotome (Leica Microsystems) with a diamond knife, and mounted on grids. The thin sections on grids were stained with aqueous 2.5% aqueous gadolinium (III) acetate hydrate and Sato's lead citrate stains using a modified Hiraoka grid staining system (Seifert 2017). Sections were imaged by TEM with accelerating voltage at 80 kV (FEI Tecnai G2 Spirit transmission electron microscopy).

Immunohistochemistry (IHC): The expression of specific markers by different cells (HCEp and HCF populated on the glued area from the retention experiment was determined by fluorescence immunohistochemistry on the paraffin embedded tissue sections as previously described. First, paraffin was removed by xylene, and then the samples were rehydrated in water through a graded series of alcohols (100%, 96%, 70%, 50%, and water). Next, tissue sections were incubated in 10 mM sodium citrate buffer, 0.05% w/w tween 20 (pH 6.0) at 60° C. for overnight, and washed with tris-buffered saline (TBS) plus 0.025% w/w Triton X-100, followed by blocking any unspecific binding sites using TBS supplemented with 10% (fatal bovine serum) FBS and 1% bovine serum albumin (BSA). The sections then incubated with the corresponding primary antibodies as listed below overnight at 4° C. in humidifying conditions. (i) mouse monoclonal antibodies against HCEp specific cytokeratin (anti-cytokeratin 3+12, clone AE5; ab68260, dilution 1:50, abcam); (ii) mouse monoclonal antibody against ALDH3A1 (clone 1B6; GTX84889, dilution 1:50, GenTex); (iii) mouse monoclonal antibodies against alpha smooth muscle actin (clone 1A4; ab781, dilution 0.5 ug/ml, abcam). Then, the specimens were incubated with FITC-conjugated anti-mouse antibody (ab6785, dilution 1:100, abcam) as a secondary antibody for 1 h at room temperature. Finally, the slides were mounted in VectaShield mounting media containing DAPI (Vector Laboratories), and imaged by an inverted fluorescent microscope (Zeiss Axio Observer Z1).

Immunocytochemistry (ICC): To evaluate the expression of ZO-1 marker by HCEn cultured on the GELGYM, we used standard ICC assay. Briefly, HCEn (10000 per each well) were seeded on the GELGYM culture discs with varying CT (3, 5, 10 min), followed by addition of 100 µl appropriate media as previously described and incubated at 37° C. and 5% $CO_2$ condition. Afterwards, the discs were removed from media, carefully rinsed with PBS and fixed in 4% paraformaldehyde, followed by dehydration in ethanol solutions with graded concentrations (70%, 96%, 100%) for 30 minutes at each concentration. Then the discs were first immersed (twice for 30 minutes each) in xylene then in liquid paraffin (30 minutes). The paraffin-embedded constructs were sectioned to 6-µm thickness with a microtome. Similar to IHC procedure as explained above, the sections were washed, rehydrated and their unspecific binding was blocked. The sections then, incubated with the rabbit polyclonal antibodies against ZO-1 (ZO-1 Polyclonal Antibody, dilution: 1:100, ThermoFisher Scientific) as a primary antibody overnight at 4° C. in humidifying conditions. Afterwards, the specimens were incubated with Cy5-conjugated anti-Rabbit antibody (Cat. code, dilution 1:200) as a secondary antibody for 1 h at room temperature, mounted in VectaShield mounting media containing DAPI (Vector Laboratories), and imaged by an inverted fluorescent microscope (Zeiss Axio Observer Z1).

Ex Vivo Burst Pressure Test: The pressure of the GELGYM hydrogels [n=6] were acquired by adopted ASTM F2392-04 standard (fresh porcine cornea was used instead of collagen sheet) (see SI section). Fresh porcine eyes were obtained from adult pigs immediately after their death at a local slaughterhouse, and inspected carefully to discard those showing any corneal damage. Selected corneas were removed from porcine eyes with a 16-mm diameter trephine and washed with phosphate buffer saline (PBS). Then, the corneas were full-thickness trephined with a varying size (2-8 mm) Barron trephine, and placed in the artificial corneal chamber (Barron Precision Instruments) equipped with syringe pump (NE-300, ArrEssPro Scientific), loaded with PBS. The syringe was run to fill the artificial chamber with PBS, and then the GELGYM solution (20-50 µl depending on the size of the defect) was applied into the defect using a micropipette and crosslinked by irradiation of LED light for varying CT (3-10 min). In case of larger perforations, first the 20 µl of GELGYM solution was applied into periphery of the either pre-crosslinked GELGYM patch, or corneal graft and the inserted in the perforated hole, and immediately radiated by LED light for 0.5 min to crosslink and seal the perforation. Then, 50 µl of GELGYM solution was carefully applied onto the area and radiated for varying CT to completely seal the wound. The syringe was set to pump the PBS with 0.2 ml/min, into chamber and the burst pressure measured by pressure sensor (PASCO, PS-2017) and recorded by computer via PASCO Capston interface.

Lap Shear Adhesion Test: The adhesion of the GELGYM with various organs of lamb (aorta, muscle, heart, kidney, liver and spleen [n=8] was evaluated according to modified ASTM F2255-05 standard lap shear test. Two poly methyl methacrylate (PMMA) slides (10×40 ×1 mm) were used to hold the tissue and functionalized surface. First, a glass cover slip (10 mm diameter) was functionalized with 3-(Trimethoxysilyl)propyl methacrylate (Sigma) as previously described, then superglued to PMMA slide, and was dried overnight (top slide). Then, using a blade, a fresh organ is dissected into (10×10×5 mm) fragments and superglued in another PMMA slide (bottom one), and air dried for 1 min. Then, the prepolymer solution (50 µl) was added onto the tissue and then other slide was carefully put on the GELGYM solution (FIGS. 11, and 23a-23d). After assembly, the glue between the two slides was radiated with LED light to attach the tissue to the functionalized glass. The two PMMA slides were placed in the mechanical tester, and the shear test was run with the 2 mm/min crosshead speed. The adhesive strength was measured at the point of detaching of glue from the tissue.

In Vivo Biocompatibility:

To assess the effectiveness and biocompatibility of the GELGYM, we performed a deep anterior lamellar keratectomy in the rabbit [n=3]. The corneas were partially trephined (150-200 µm thickness) in the periphery with an 8-mm Barron trephine. Afterwards, the air was injected in the deep central corneal stroma to create a separation of the anterior stroma and the Descemet's membrane ("big bubble technique"), using a bent 30 G needle with the bevel facing down. Then, using a crescent blade, we will dissect and cut the anterior stroma from the Descemet's membrane. The tissue gap was filled with 50 µl of GELGYM and immediately crosslinked for 5 min using LED light. Then, routine examinations were performed at daily bases until one week after surgery, followed by weekly check until the end experiment (1 month). Afterwards, the rabbits were euthanized, and their eyes were carefully removed and placed in 4% paraformaldehyde. Then the corneas were cautiously removed from rabbit eyes with a 16-mm diameter trephine, fixed with 4% paraformaldehyde, and dehydrated in grading concentrations of ethanol (70%, 96%, 100%) for 30 min at each concentration. Then the tissues were first immersed (twice for 30 minutes each) in xylene then in liquid paraffin (30 minutes). The paraffin-embedded constructs were sectioned to 6-µm thickness with a microtome and stained for histology, where the exposed to hematoxylin (Hematoxylin Stain 2, Fisher Chemical) for 2 min and eosin for 1 min (Fisher Chemical).

Example 4: (I) Determination of GELGYM's Ability as an Adhesive Sealant to Close Primary Corneal and Corneoscleral Injuries after Ocular Trauma Glycidyl methacrylate-substituted gelatin (GELGYM) acts as a sealant to close corneal and corneoscleral injuries after ocular trauma, based on strong covalent and non-covalent interaction of glycidyl methacrylate-substituted gelatin with surrounding tissue along with strong entanglement stemming from diffusion of glycidyl methacrylate-substituted gelatin into corneal and/or the scleral extracellular matrix and subsequent polymerization. This leads to strong and water-tight sealing of the perforation, yet accompanied by the cell migration and the regeneration of the damaged area by host corneal cells over time.

I.1: Evaluation of the Sealant Capacity of GELGYM in Central Corneal Injuries:

(A) Generation of glycidyl methacrylate-substituted gelatin: The glycidyl methacrylate-substituted gelatin prepolymer is synthesized from reaction with gelatin solution in PBS with glycidyl methacrylate under sterile conditions. After completion of the reaction, dialysis membrane is used to purify glycidyl methacrylate-substituted gelatin, followed by freeze-drying to obtain foam-like prepolymer product. Afterwards, glycidyl methacrylate-substituted gelatin is mixed with 0.05 mM eosin Y, 0.4% w/v triethanolamine, and 0.4% w/v vinyl caprolactam, and its concentration adjusted to 22.5% w/w. Prior to the application of the prepolymer, it is passed through sterile filters (0.2 micron) for secondary sterilization process.

(B) Performing a central corneal injury in the rabbit: 12 Dutch-Belted rabbits (3 months or older, 1 kg or more, male and female rabbits based on an equal distribution) are used. 12 more female rabbits are included for the burst pressure test (the use of only female rabbits for this experiment is based on the assumption of the worst-case scenario because of the previously described corneal wound healing delay in women versus men). A Castroviejo caliper is used to mark a horizontal 3 mm line that has its center in the apex of the cornea. Afterwards, a 3-mm clear full-thickness corneal incision is performed using a stab blade (15°), avoiding damaging any other structures such as the anterior lens capsule.

(C) Application of glycidyl methacrylate-substituted gelatin to the corneal injury: First, 20 µl of glycidyl methacrylate-substituted gelatin is placed in the injured area with a micropipette in the experimental group (n=6). Then, the engineered visible light (turquoise LED flash light, 500-520 nm and 20 m W/cm$^2$ intensity) is applied for duration of 5 min, while keeping the light 5 mm above the tissue, to optimally polymerize the bioadhesive. A control group is established based on routine treatment, closing the incision with 2 interrupted 10/0 nylon sutures (n=6).

(D) Clinical evaluation of the local safety and efficacy of glycidyl methacrylate-substituted gelatin compared to the control group: The preclinical animal models are followed up during 12 months. During that period, routine examinations are performed at day 0 (immediately before the surgery-baseline-), 7, 14, 28 (1 month) and monthly during the first 6 months. Afterwards, the examinations are performed every 2 months. The exam is based on an evaluation of the anterior and posterior segment of the operated eye using the following instruments and techniques:

(a) Slit lamp biomicroscopy: allows the inventors to evaluate for inflammation or disruption of the anatomy in the anterior segment of the eye. The presence of different complications is recorded following the Sotozono's grading system: corneal complications (superficial punctate keratopathy, epithelial defect, loss of the palisades of Vogt, conjunctivalization, neovascularization, opacification, and keratinization), conjunctival complications (hyperemia and symblepharon formation), and eyelid complications (trichiasis, mucocutaneous junction involvement, meibomian gland involvement and punctal damage). Representative pictures are taken. Moreover, Seidel test is performed to reveal aqueous leak with the use of fluorescein solution. Furthermore, other signs of infection or inflammation that can affect the cornea (i.e. melting, infiltrates, etc.), the sclera (i.e. enogorgement of superficial and/or deep episcleral vessels), the anterior chamber (i.e. Tyndal effect, presence of fibrin, change of depth, etc.), the iris (i.e. atropy, neovascularization, etc.) or the lens (i.e. opacities, deposits on the anterior lens capsule, etc.) are recorded.

(b) Anterior segment optical coherence tomography of the cornea and anterior chamber angle: allows the inventors to objectively quantify any disruption of the anatomy in the anterior segment, such as changes in corneal thickness or presence of gaps in the tissue or the applied glycidyl methacrylate-substituted gelatin, together with the objective measurement of the anterior chamber angle in order to record any possible closure angle. Furthermore, it allows the inventors to observe and quantify the degradation of the bioadhesive, measuring its area and volume.

(c) In vivo confocal microscopy evaluation: allows the inventors to determine clinical and histological changes in the cornea and other structures of the anterior segment after the treatment for the assessment of the control of scarring and pathological healing responses. Several histological features are analyzed using the in vivo confocal microscopy: migration of corneal epithelial cells and fibroblasts into the bioadhesive, infiltration of inflammatory cells, neovascularization, nerve regeneration (sub-basal nerve plexus), and morphological changes in the corneal epithelium, stroma and endothelium. Thus, it helps the inventors to study the interactions of the bioadhesive with corneal and immune cells together with other structures such as nerves or vessels.

(d) Optical coherence tomography of the posterior segment: is carried out in order to reveal any possible adverse effect of the applied treatment to the vitreous, retina, choroid and optic nerve (i.e. signs of inflammation, signs of neuronal or vascular atrophy, etc.).

(e) The intraocular pressure (TOP) of the eye is assessed in order to evaluate possible adverse effects on IOP because of induction of inflammation, toxicity or damage to the angle or the ciliary body. For the evaluation of TOP after the treatment, direct manometry is used immediately before the surgery and then 1 month, 3 months, 6 months, 9 months and 12 months after the surgery. Intracameral IOP measurements are performed in anesthetized rabbits using an electromechanical pressure sensor (PASCO scientific company, PS-2017) attached to a 30-gauge needle. Measurements are performed by inserting the needle in the anterior chamber of the eye through a clear corneal puncture next to the corneoscleral limbus.

(E) Histological evaluation of the cell biocompatibility and biointegration of glycidyl methacrylate-substituted gelatin compared to the control group: To confirm results, histological evaluation of the corneoscleral area, together with transmission electron microscopy (TEM) and protein evaluation based on fluorescence immunohistochemistry, is performed after euthanizing the rabbits 12 months after treatment, which allows the inventors to assess the degree of scarring and pathological healing responses. TEM reveals any presence of the biomaterial implanted together with its integration and interaction with the extracellular matrix and the host corneal cells. Corneal epithelial differentiation is analyzed by expression of CK3 and CK12 (specific corneal epithelial markers), in conjunction with galectin 7 (stratified panepithelial marker), ZO1 (marker of tight junctions in corneal stratified epithelium), and CK5/14 (stratified squamous epithelial tissue marker). Fibroblast differentiation is assessed through ALDH3A1 (keratocyte marker), alpha-SMA (myofibroblast marker, associated to fibrosis), collagen I and keratocan (corneal stromal markers), and collagen III (fibrotic marker)(this facilitates the evaluation of the control of scarring and pathological healing response associated to corneal fibroblasts). Corneal endothelium differentiation is analyzed by expression of Na+K+/ATPase and ZO-1. The immune response is characterized through CD45 (panleukocyte marker), CD4 (Th lymphocyte), CD8 (Tc lymphocyte), CD68 (macrophage), anti-ly6G clone 1A8 (neutrophil), CCR3 (eosinophil), and CD11b (macrophage, monocyte, granulocyte, and dendritic cell) markers.

(F) Direct evaluation of the sealant capacity of glycidyl methacrylate-substituted gelatin compared to the control group: To quantify the degree of adhesion of glycidyl methacrylate-substituted gelatin to the corneal tissue in vivo, a burst pressure test is immediately performed after euthanizing the rabbits at 6 and 12 months (n=3 per group and per time point). For that purpose, the rabbit corneal is trephined with a scleral rim diameter of 16 mm to fit perfectly in a Barron artificial anterior chamber (Katena, K20-2125) with one port connected to an electromechanical pressure sensor (PASCO scientific company, PS-2017) and the second port to a syringe filled with PBS placed in a pump that maintains a constant flow of 0.1 ml/min. The maximum pressure tolerated by the system before the rupture of the cornea is recorded. The sutures in the control group are removed immediately before starting the burst pressure test, once the cornea is placed in the chamber. Moreover, a histological evaluation similar to I.1.E is performed to the remnant ocular tissue after the burst pressure test.

(G) Statistical analysis and sample size calculation: Independent t-test analysis with Bonferroni adjustment is performed to compare the experimental group versus the control group. Power analysis for an independent sample t-test was conducted in UCSF Biostatistics Power and Sample Size Calculator to determine a sufficient sample size using an alpha of 0.05, a power of 0.80, two tails and a normal distribution. The estimated difference between means was 25%, assuming an estimated standard deviation of 15%, based on our preliminary data. There is an equal allocation of samples into each group. Based on the aforementioned assumptions, the desired sample size is 6. Specifically, for I.1.F, taking into account that the estimated difference between means was 50%, assuming an estimated standard deviation of 20%, the desired sample size is 3.

I.2: Evaluation of the Sealant Capacity of GELGYM in Paracentral and Peripheral Corneoscleral Injuries:

(A) Performing a paracentral and peripheral corneoscleral injury in the rabbit: 12 Dutch-Belted rabbits (3 months or older, 1 kg or more, male and female rabbits based on an equal distribution) are used. A Castroviejo caliper is used to mark a temporal (to avoid the nictitating membrane of the rabbit eye) horizontal 3 mm line from the limbus to the center of the cornea. Then, a 2 mm line is marked on the sclera following the previous drawn line (always on top of the pars plana area to diminish the probability of damaging the retina while we perform the incision). Afterwards, a 5 mm corneoscleral full-thickness incision is performed using a stab blade (15°), from sclera to cornea, avoiding damaging the anterior lens capsule, the iris or the choroid.

(B) Application of glycidyl methacrylate-substituted gelatin to the corneal injury: First, 30 µl of glycidyl methacrylate-substituted gelatin is placed in the injured area with a micropipette in the experimental group (n=6). Then, engineered visible light is applied for the duration of 5 min to polymerize the bioadhesive as described in I.1.B. A control group is established closing the corneal laceration with interrupted 10/0 nylon sutures and the scleral incision with 8/0 silk sutures (n=6). Any iris or choroid prolapse is reposited with a blunt spatula to avoid wound entrapment.

(C) Clinical and histological evaluation of glycidyl methacrylate-substituted gelatin compared to the control group and statistical analysis and sample size calculation is performed as described in I.1.

Example 5: (II) Determination of the Ability of GELGYM to Act as a Corneal Substitute to Perform Sutureless Keratoplasties, without the Need of Donor Corneas Glycidyl methacrylate-substituted gelatin acts as a corneal substitute, based on its optical and mechanical properties, similar to the human cornea, together with its optimal biointegration and cell biocompatibility shown in the in vitro experiments already performed. Moreover, its adhesiveness to the corneal tissue facilitates the sutureless implantation of this bioengineered construct avoiding the complications associated with corneal sutures.

II.1: Evaluation of the Ability of a GELGYM-Based Construct to Substitute for Human Donor Cornea in a Sutureless Deep Anterior Lamellar Keratoplasty.

(A) Performing a deep anterior lamellar keratectomy in the rabbit: 12 Dutch-Belted rabbits (3 months or older, 1 kg or more, male and female rabbits based on an equal distribution) are used. The cornea is partially trephined (150-200 micron thickness) in the periphery with a 6-mm Barron trephine. Afterwards, air is injected in the deep central corneal stroma to create a separation of the anterior stroma and the Descemet's membrane ("big bubble technique"), using a bent 30 G needle with the bevel facing down. Then, using a crescent blade, the anterior stroma from the Descemet's membrane is dissected and cut.

(B) Application of glycidyl methacrylate-substituted gelatin to the corneal injury: The tissue gap created by performing a deep anterior keratectomy is filled with GELGYM. First, 50 µl of glycidyl methacrylate-substituted gelatin is placed in the keratectomized area with a micropipette in the experimental group (n=6). Then, the engineered visible light is applied for the duration of 5 min to polymerize the bioadhesive as previously described in I.1.B. A control group is established based on routine treatment, performing a deep anterior lamellar keratoplasty using a corneal graft (n=6). For that purpose, a rabbit donor cornea is trephined with a 6.5-mm corneal trephine. The corneal endothelium is mechanically removed from the graft, and the donor graft sutured in place to the peripheral host cornea using interrupted 10/0 nylon sutures.

(C) Clinical and histological evaluation of glycidyl methacrylate-substituted gelatin compared to the control group and statistical analysis and sample size calculation is performed as described in I.1.

(D) Clinical evaluation of corneal re-innervation by corneal esthesiometry: corneal sensation is assessed in the center of the cornea using a handheld esthesiometer (i.e. Cochet-Bonnet) in order to evaluate the functional re-innervation of the treated area. This assessment is performed immediately before the surgery and then 1 month, 3 months, 6 months, 9 months and 12 months after the surgery.

II.2: Evaluation of the Ability of a GELGYM to Act as a Corneal Substitute in a Penetrating Keratoplasty.

(A) Performing full-thickness keratectomy in the rabbit: 18 Dutch-Belted rabbits (3 months or older, 1 kg or more, male and female rabbits based on an equal distribution) are used. 12 more female rabbits are included for the burst pressure test. The cornea is full-thickness trephined with a 6-mm Barron trephine.

(B) Application of glycidyl methacrylate-substituted gelatin to the corneal injury: Two different approaches are assessed: sutureless grafting of a donor cornea using glycidyl methacrylate-substituted gelatin as adhesive to graft the donor cornea to the host; and implantation of a solid glycidyl methacrylate-substituted gelatin patch that substitutes for the donor cornea, using glycidyl methacrylate-substituted gelatin as adhesive to graft the glycidyl methacrylate-substituted gelatin patch to the host (n=6 per experimental group).

(a) In the first experimental group, a rabbit donor cornea is trephined with a 6.5-mm corneal trephine. Then, the periphery of the donor cornea is covered with 30 µl glycidyl methacrylate-substituted gelatin using a micropipette. Afterwards, the graft is placed in the corneal host bed already trephined. Once the graft is in place, it is radiated with the engineered visible light for the duration of 30 sec to seal the junction between the donor and the host. Then, another 30 µl of glycidyl methacrylate-substituted gelatin is applied on top of the host-donor junction, followed by 5 min visible light exposure to polymerize the adhesive and bind it to the surrounding tissue.

(b) In the second experimental group, a solid glycidyl methacrylate-substituted gelatin patch is generated as corneal substitute. First, 60 µl of glycidyl methacrylate-substituted gelatin is transferred to a silicon-made mold with the diameter of 6 mm, and thickness of 1 mm, that is followed by 5 min of visible light exposure to harden the polymer. Then, it is grafted using the engineered visible light on a similar way to the donor cornea in the previous experimental group described in II.2.B.b.

(c) A control group for both experimental groups is established based on routine treatment, performing a penetrating keratoplasty using a corneal graft (n=6). For that purpose, a rabbit donor cornea is trephined with a 6.5-mm corneal trephine. Afterwards, the donor cornea is sutured in place with the peripheral host cornea using interrupted 10/0 nylon sutures.

(C) Clinical and histological evaluation of glycidyl methacrylate-substituted gelatin compared to the control group and statistical analysis and sample size calculation is performed as described in I.1. Moreover, a clinical evaluation of the corneal re-innervation by corneal esthesiometry is carried out as described in II.1.D. Furthermore, specifically for the first experimental group (sutureless grafting of a donor cornea using glycidyl methacrylate-substituted gelatin), a direct evaluation of the sealant capacity of glycidyl methacrylate-substituted gelatin compared to the control group by burst pressure test is performed as described in I.1.F.

Example 6: (III) to Determine the Local and Systemic Biosafety of GELGYM after its Implantation Glycidyl methacrylate-substituted gelatin is locally and systemically safe, without causing any adverse event. Glycidyl methacrylate-substituted gelatin is composed of gelatin and glycidyl methacrylate. Its base material is gelatin, which is derived from collagen. Gelatin degradation leads to amino acid synthons that are not toxic and can be consumed by the cells, as observed in our studies. The highest degree of glycidyl methacrylate-substituted gelatin functionalization has 6.7% w/w of glycidyl methacrylate functional group. Radical crosslinking reaction gives dimethacrylate units which bridge the gelatin chains, creating a 3D network of hydrogel. As chemical bond between gelatin and glycidyl methacrylate, and also between glycerol and methacrylate, are esteric bonds that are susceptible to biodegradation over time. In our experimental study, we use less than 100 µL of glycidyl methacrylate-substituted gelatin with the concentration of 22.5% and as the only 3.5% and 3.2% of glycidyl methacrylate-substituted gelatin composed of glycerol and methacrylic acid, having maximum 0.78 and 0.72 mg of those components respectively in our study. Since the degradation of glycidyl methacrylate-substituted gelatin spans in a period of more than 6 months, as suggested by our in vitro and ex vivo data, therefore, with the tear flow of 6-7 µL/min and the aqueous humor flow of 1.5-3 µL/min, the concentration of these component is almost 4.31 µM (0.43 and 0.39 ppm, respectively) which is well below the minimum toxicity level of 100 µM reported for acrylate monomers that are the most reactive form of this class chemicals. Moreover, glycerol is a precursor for synthesis of triacylglycerols and of phospholipids, and with that has no toxicity on that concentration. Therefore, no toxic effect is associated to the degradation of glycidyl methacrylate-substituted gelatin after applying in vivo. Eosin Y crosslinking system composed of eosin Y, triethanolamine and n-vinylcaprolactam is a Food and Drug Administration (FDA)-approved photo induced crosslinking process that can be excited by visible light (450-550 nm) and was used in photocrosslinkable lung sealant FocalSeal® (Genzyme Biosurgical, Cambridge, MA). Therefore, no toxic effect is associated with the application of such visible light crosslinking system.

III.1: Evaluation of the Ocular Biosafety of GELGYM.

(A) Clinical evaluation: The data is obtained from the clinical evaluation performed in I and II.

(B) Histological evaluation: A histological evaluation of the operated eye is performed based on a hematoxylin and eosin staining of the rest of the ocular tissues including lids, conjunctiva, iris, ciliary body, lens, choroid and retina. The data from the cornea and the sclera is obtained from the histological evaluation performed in I and II. Signs of inflammation or tumorigenesis are recorded. The non-operated eye is also processed and analyzed.

III.2: Evaluation of the Systemic Biosafety of GELGYM.

(A) Clinical evaluation: Clinical examinations are carried out and recorded once weekly. Body weights are measured prior to implantation and weekly thereafter. Any abnormal behavior or sign of the rabbit is recorded as a possible indication of discomfort or adverse effect after applying the treatment, such as inactivity, lethargic, abnormal discharge, dermatitis, hunched posture, dehydration, piloerection, diarrhea, urine abnormalities, etc. Moreover, a blood test is performed immediately after the surgery, after 7 days and after 1, 3, 6 and 12 months after applying the treatment to the rabbit in order to evaluate any systemic inflammatory effect of the treatment. The blood test is based on a complete blood count and a basic metabolic panel, including the C-reactive protein test. Whole blood is collected into EDTA-coated tubes for hematology and into commercial serum separation gel tubes for the metabolic panel.

(B) Histological evaluation (necropsy): A systemic histological evaluation of multiple panel organs is performed at 12 months after euthanizing the rabbits, analyzing brain, heart, lungs, liver, and kidneys. A macroscopic examination is performed to assess any evident tissue reactions to glycidyl methacrylate-substituted gelatin, including inflammatory reactions and carcinogenesis. The local draining lymph nodes of the cornea (cervical lymph nodes) is assessed macroscopically and histologically. Tissues are weighed and preserved in 10% neutral buffered formalin until testing and pathology evaluated. Tissues are trimmed and embedded in paraffin. Several sections approximately 5 microns thick are prepared from each site. Slides are stained with hematoxylin and eosin. The histological response parameters that are assessed and recorded are based on the international standards ISO 10993-6 (2007) and include (but are not limited to) the presence and extent of fibrosis/fibrous capsule; the extent of inflammation based on the number and types of inflammatory cells present; degeneration as determined by changes in tissue morphology and differences in tinctorial staining; presence, extent, and type of necrosis; tissue alterations such as fragmentation and/or presence of debris, fatty infiltration and granuloma formation; presence and form of glycidyl methacrylate-substituted gelatin remnants, material fragmentation, and debris; and the nature and extent of tissue ingrowth, including signs of carcinogenesis. The scaling of the lesions is based on the semiquantitative criteria presented by Shackelford et al., in which grade 1 corresponds to lesion barely noticeable and/or up to 10% of the tissue is affected; grade 2: the lesion is noticeable, up to 20% of the tissue is affected; grade 3: the lesion is a prominent feature of the tissue, up to 40% of the tissue is affected; grade 4: the lesion is an overwhelming feature of the tissue, more than 41% of the tissue is affected.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

REFERENCES

1. Lee K Y, Mooney D J. Hydrogels for tissue engineering. *Chem Rev* 2001, 101(7): 1869-1879.
2. Leijten J, Seo J, Yu K, Trujillo-de Santiago G, Tamayol A, Ruiz-Esparza G U, et al. Spatially and temporally controlled hydrogels for tissue engineering. *Mat Sci Eng R* 2017, 119: 1-35.
3. Galler K M, Aulisa L, Regan K R, D'Souza R N, Hartgerink J D. Self-Assembling Multidomain Peptide Hydrogels: Designed Susceptibility to Enzymatic Cleavage Allows Enhanced Cell Migration and Spreading. *J Am Chem Soc* 2010, 132(9): 3217-3223.
4. Cushing M C, Anseth K S. Hydrogel Cell Cultures. *Science* 2007, 316(5828): 1133-1134.
5. Jeon S J, Hauser A W, Hayward R C. Shape-Morphing Materials from Stimuli-Responsive Hydrogel Hybrids. *Acc Chem Res* 2017, 50(2): 161-169.
6. Woo L J, Yeon K S, Soo K S, Moo L Y, Hyun L K, Jeong K S. Synthesis and characteristics of interpenetrating polymer network hydrogel composed of chitosan and poly(acrylic acid). *Journal of Applied Polymer Science* 1999, 73(1): 113-120.
7. Mandal B B, Kapoor S, Kundu S C. Silk fibroin/polyacrylamide Semi-interpenetrating network hydrogels for controlled drug release. *Biomaterials* 2009, 30(14): 2826-2836.
8. Myung D, Waters D, Wiseman M, Duhamel P E, Noolandi J, Ta C N, et al. Progress in the development of interpenetrating polymer network hydrogels. *Polym Adv Technol* 2008, 19(6): 647-657.
9. Huang T, Xu H G, Jiao K X, Zhu L P, Brown H R, Wang H L. A novel hydrogel with high mechanical strength: A macromolecular microsphere composite hydrogel. *Adv Mater* 2007, 19(12): 1622-+.
10. Shi F K, Wang X P, Guo R H, Zhong M, Xie X M. Highly stretchable and super tough nanocomposite physical hydrogels facilitated by the coupling of intermolecular hydrogen bonds and analogous chemical crosslinking of nanoparticles. *J Mater Chem B* 2015, 3(7): 1187-1192.
11. Sun J Y, Zhao X H, Illeperuma W R K, Chaudhuri O, Oh K H, Mooney D J, et al. Highly stretchable and tough hydrogels. *Nature* 2012, 489(7414): 133-136.
12. Sakai T, Matsunaga T, Yamamoto Y, Ito C, Yoshida R, Suzuki S, et al. Design and fabrication of a high-strength hydrogel with ideally homogeneous network structure from tetrahedron-like macromonomers. *Macromolecules* 2008, 41(14): 5379-5384.
13. Mayumi K, Ito K. Structure and dynamics of polyrotaxane and slide-ring materials (vol 51, pg 959, 2010). *Polymer* 2010, 51(20): 4461-4461.
14. Tuncaboylu D C, Sari M, Oppermann W, Okay O. Tough and Self-Healing Hydrogels Formed via Hydrophobic Interactions. *Macromolecules* 2011, 44(12): 4997-5005.
15. Appel E A, Tibbitt M W, Webber M J, Mattix B A, Veiseh O, Langer R. Self-assembled hydrogels utilizing polymer-nanoparticle interactions. *Nat Commun* 2015, 6.
16. Sharma B, Fermanian S, Gibson M, Unterman S, Herzka D A, Cascio B, et al. Human cartilage repair with a photoreactive adhesive-hydrogel composite. *Sci Transl Med* 2013, 5(167): 167ra166.
17. Prausnitz M R, Langer R. Transdermal drug delivery. *Nat Biotechnol* 2008, 26(11): 1261-1268.
18. Cynthia G, Kristie C, K. RE, Ara N, W. GM. A Dendritic Thioester Hydrogel Based on Thiol-Thioester Exchange as a Dissolvable Sealant System for Wound Closure. *Angewandte Chemie International Edition* 2013, 52(52): 14070-14074.
19. Feiner R, Engel L, Fleischer S, Malki M, Gal I, Shapira A, et al. Engineered hybrid cardiac patches with multifunctional electronics for online monitoring and regulation of tissue function. *Nat Mater* 2016, 15(6): 679-685.
20. Lang N, Pereira M J, Lee Y, Friehs I, Vasilyev N V, Feins E N, et al. A blood-resistant surgical glue for minimally invasive repair of vessels and heart defects. *Sci Transl Med* 2014, 6(218): 218ra216.
21. Li J, Celiz A D, Yang J, Yang Q, Wamala I, Whyte W, et al. Tough adhesives for diverse wet surfaces. *Science* 2017, 357(6349): 378-381.
22. Kretlow J D, Klouda L, Mikos A G. Injectable matrices and scaffolds for drug delivery in tissue engineering. *Adv Drug Deliv Rev* 2007, 59(4-5): 263-273.
23. Park H, Temenoff J S, Holland T A, Tabata Y, Mikos A G. Delivery of TGF-beta1 and chondrocytes via injectable, biodegradable hydrogels for cartilage tissue engineering applications. *Biomaterials* 2005, 26(34): 7095-7103.
24. Lai J Y, Li Y T. Functional Assessment of Cross-Linked Porous Gelatin Hydrogels for Bioengineered Cell Sheet Carriers. *Biomacromolecules* 2010, 11(5): 1387-1397.
25. Mimura T, Amano S, Yokoo S, Uchida S, Yamagami S, Usui T, et al. Tissue engineering of corneal stroma with rabbit fibroblast precursors and gelatin hydrogels. *Mol Vis* 2008, 14: 1819-1828.
26. Lai J Y, Li Y T, Cho C H, Yu T C. Nanoscale modification of porous gelatin scaffolds with chondroitin sulfate for corneal stromal tissue engineering. *Int J Nanomed* 2012, 7: 1101-1114.
27. Haugh M G, Jaasma M J, O'Brien F J. The effect of dehydrothermal treatment on the mechanical and structural properties of collagen-GAG scaffolds. *J Biomed Mater Res A* 2009, 89(2): 363-369.
28. Zhao X, Lang Q, Yildirimer L, Lin Z Y, Cui W, Annabi N, et al. Photocrosslinkable Gelatin Hydrogel for Epidermal Tissue Engineering. *Adv Healthc Mater* 2016, 5(1): 108-118.
29. Ni Annaidh A, Bruyere K, Destrade M, Gilchrist M D, Ottenio M. Characterization of the anisotropic mechanical properties of excised human skin. *J Mech Behav Biomed Mater* 2012, 5(1): 139-148.
30. ASTM D638-14, Standard Test Method for Tensile Properties of Plastics. *ASTM International*. West Conshohocken, Pa.; 2014.
31. ASTM D695-15, Standard Test Method for Compressive Properties of Rigid Plastics. *ASTM International*. West Conshohocken, PA; 2015.
32. Sperling L H. *Introduction to Physical Polymer Science*. Wiley, 2015.
33. Benton J A, DeForest C A, Vivekanandan V, Anseth K S. Photocrosslinking of Gelatin Macromers to Synthesize Porous Hydrogels That Promote Valvular Interstitial Cell Function. *Tissue Eng Pt A* 2009, 15(11): 3221-3230.
34. Pascolini D, Mariotti S P. Global estimates of visual impairment: 2010. *Br J Ophthalmol* 2012, 96(5): 614-618.
35. Grinstaff M W. Designing hydrogel adhesives for corneal wound repair. *Biomaterials* 2007, 28(35): 5205-5214.
36. Garzon I, Martin-Piedra M A, Alfonso-Rodriguez C, Gonzalez-Andrades M, Carriel V, Martinez-Gomez C, et al. Generation of a biomimetic human artificial cornea model using Wharton's jelly mesenchymal stem cells. *Invest Ophthalmol Vis Sci* 2014, 55(7): 4073-4083.
37. Gonzalez-Andrades M, de la Cruz Cardona J, Ionescu A M, Campos A, Del Mar Perez M, Alaminos M. Generation of bioengineered corneas with decellularized xenografts and human keratocytes. *Invest Ophthalmol Vis Sci* 2011, 52(1): 215-222.
38. Alaminos M, Gonzalez-Andrades M, Munoz-Avila J I, Garzon I, Sanchez-Quevedo M C, Campos A. Volumetric and ionic regulation during the in vitro development of a corneal endothelial barrier. *Exp Eye Res* 2008, 86(5): 758-769.
39. Bhatia S S. Ocular surface sealants and adhesives. *Ocul Surf* 2006, 4(3): 146-154.
40. Jhanji V, Young A L, Mehta J S, Sharma N, Agarwal T, Vajpayee R B. Management of Corneal Perforation. *Surv Ophthalmol*, 56(6): 522-538.
41. Food and Drug Administration. ReSure® Sealant—P130004. 2014.
42. Rana M, Savant V. A brief review of techniques used to seal corneal perforation using cyanoacrylate tissue adhesive. *Cont Lens Anterior Eye* 2013, 36(4): 156-158.

43. Pardo L, Osman R, Weinstein H, Rabinowitz J R. Mechanisms of nucleophilic addition to activated double bonds: 1,2- and 1,4-Michael addition of ammonia. *J Am Chem Soc* 1993, 115(18): 8263-8269.
44. Vakalopoulos K A, Wu Z Q, Kroese L, Kleinrensink G J, Jeekel J, Vendamme R, et al. Mechanical Strength and Rheological Properties of Tissue Adhesives With Regard to Colorectal Anastomosis An Ex Vivo Study. *Ann Surg* 2015, 261(2): 323-331.
45. Ravi M, Paramesh V, Kaviya S R, Anuradha E, Solomon F D. 3D cell culture systems: advantages and applications. *J Cell Physiol* 2015, 230(1): 16-26.
46. Myung D, Derr K, Huie P, Noolandi J, Ta K P, Ta C N. Glucose permeability of human, bovine, and porcine corneas in vitro. *Ophthalmic Res* 2006, 38(3): 158-163.
47. Islam M M, Ravichandran R, Olsen D, Ljunggren M K, Fagerholm P, Lee C J, et al. Self-assembled collagen-like-peptide implants as alternatives to human donor corneal transplantation. *RSC Advances* 2016, 6(61): 55745-55749.
48. Garoff H, Ansorge W. Improvements of DNA sequencing gels. *Anal Biochem* 1981, 115(2): 450-457.

What is claimed is:

1. A method for treating a corneal injury or a corneal defect, comprising:
   a) applying a glycidyl methacrylate-substituted gelatin and a visible light-activated photoinitiator to the corneal injury or the corneal defect; and
   b) applying visible light to activate the visible light-activated photoinitiator and cross-linking the glycidyl methacrylate-substituted gelatin to form a cross-linked glycidyl methacrylate-substituted gelatin,
   wherein the glycidyl methacrylate-substituted gelatin has a degree of functionalization of gelatin with glycidyl methacrylate between 50% and 180% with respect to the amine groups of gelatin.

2. The method of claim 1, wherein the glycidyl methacrylate-substituted gelatin and the visible light-activated photoinitiator are formulated in same formulation.

3. The method of claim 1, wherein the glycidyl methacrylate-substituted gelatin and the visible light-activated photoinitiator are formulated in separate formulations.

4. The method of claim 3, wherein the glycidyl methacrylate-substituted gelatin and the visible light-activated photoinitiator are applied at the same time.

5. The method of claim 3, wherein the visible light-activated photoinitiator is applied prior to or after applying the glycidyl methacrylate-substituted gelatin.

6. The method of claim 1, wherein the glycidyl methacrylate-substituted gelatin has a glycidyl methacrylate to amine ratio of between about 0.2 and about 35.

7. The method of claim 1, wherein the glycidyl methacrylate-substituted gelatin is applied in a composition having a glycidyl methacrylate-substituted gelatin concentration between about 5% and about 25% weight per volume (w/v).

8. The method of claim 1, wherein the visible light-activated photoinitiator is a mixture of two or more different photoinitiators.

9. The method of claim 1, wherein the visible light is applied for a period between about 30 seconds to about 15 minutes.

10. The method of claim 1, wherein the cross-linked glycidyl methacrylate-substituted gelatin has a tensile strength of about 0.05 to about 2.5 MPa.

11. The method of claim 1, wherein the cross-linked glycidyl methacrylate-substituted gelatin has a compressive modulus of about 0.01 to about 0.75 MPa.

12. The method of claim 1, wherein the cross-linked glycidyl methacrylate-substituted gelatin has a swelling ratio of less than about 20%.

13. The method of claim 1, wherein the cross-linked glycidyl methacrylate-substituted gelatin has a swelling ratio of at least about 5%.

14. The method of claim 1, wherein the cross-linked glycidyl methacrylate-substituted gelatin is permeable to gas or small molecules.

15. The method of claim 1, wherein the cross-linked glycidyl methacrylate-substituted gelatin is substantially transparent.

16. The method of claim 1, further comprising administering a therapeutic agent to the corneal injury or the corneal defect.

17. The method of claim 1, wherein the method does not comprise a step of suturing.

18. A method for treating a soft tissue injury or wound, comprising:
   applying a cross-linked glycidyl methacrylate-substituted gelatin to a corneal injury or a corneal defect.

\* \* \* \* \*